(12) United States Patent
Salant et al.

(10) Patent No.: US 8,507,215 B2
(45) Date of Patent: Aug. 13, 2013

(54) DIAGNOSTICS FOR MEMBRANOUS NEPHROPATHY

(75) Inventors: David J Salant, Newton, MA (US);
Laurence H. Beck, Kingston, MA (US);
Gerard Lambeau, Grasse (FR)

(73) Assignees: Boston Medical Center Corporation, Boston, MA (US); Le Centre National de la Recherche Scientifique, Paris (FI)

( * ) Notice: Subject to any disclaimer, the term of this patent is extended or adjusted under 35 U.S.C. 154(b) by 0 days.

(21) Appl. No.: 13/006,864

(22) Filed: Jan. 14, 2011

(65) Prior Publication Data

US 2011/0177534 A1    Jul. 21, 2011

Related U.S. Application Data

(63) Continuation of application No. PCT/US2009/051110, filed on Jul. 20, 2009.

(60) Provisional application No. 61/081,786, filed on Jul. 18, 2008.

(51) Int. Cl.
*G01N 33/00* (2006.01)
*G01N 33/53* (2006.01)

(52) U.S. Cl.
CPC ..................................... *G01N 33/53* (2013.01)
USPC ............ 435/7.92; 435/7.1; 436/501; 436/518

(58) Field of Classification Search
None
See application file for complete search history.

(56) References Cited

U.S. PATENT DOCUMENTS

| 5,654,158 A | 8/1997 | McDonald | |
|---|---|---|---|
| 2008/0166741 A1* | 7/2008 | Tseng et al. | 435/7.92 |

FOREIGN PATENT DOCUMENTS

WO    00/37944    6/2000

OTHER PUBLICATIONS

Beck, et al., "M-Type Phospholipase A2 Receptor as Target Antigen in Idiopathic Membranous Nephropathy", New England J. of Med., 2009, vol. 361, No. 1, pp. 11-21.
Glassock, Richard J., "Human Idiopathic Membranous Nephropathy—A Mystery Solved", New England J. of Med., 2009, vol. 361, No. 1, pp. 81-83.
Ronco, et al, "Target antigens and nephritogenic antibodies in membranous nephropathy: of rats and men", Semin. Immunopathol., 2007, vol. 29, No. 4, pp. 445-458.

* cited by examiner

*Primary Examiner* — Gary W Counts
(74) *Attorney, Agent, or Firm* — Ronald I. Eisenstein; Tari W. Mills; Nixon Peabody LLP

(57) ABSTRACT

The invention provides immunoassays for detecting serum auto-antibodies reactive against a phospholipase A2 receptor (PLA2R) and uses thereof for diagnosis and prognosis evaluation of idiopathic membranous nephropathy (MN).

20 Claims, 16 Drawing Sheets

*Fig. 1A*
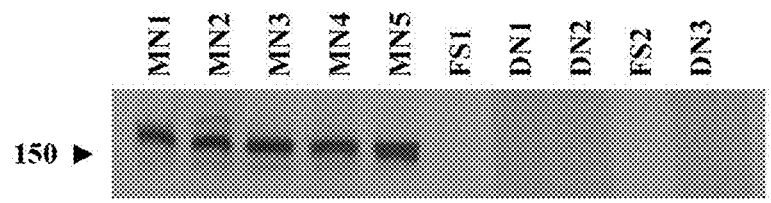
*Fig. 1B*
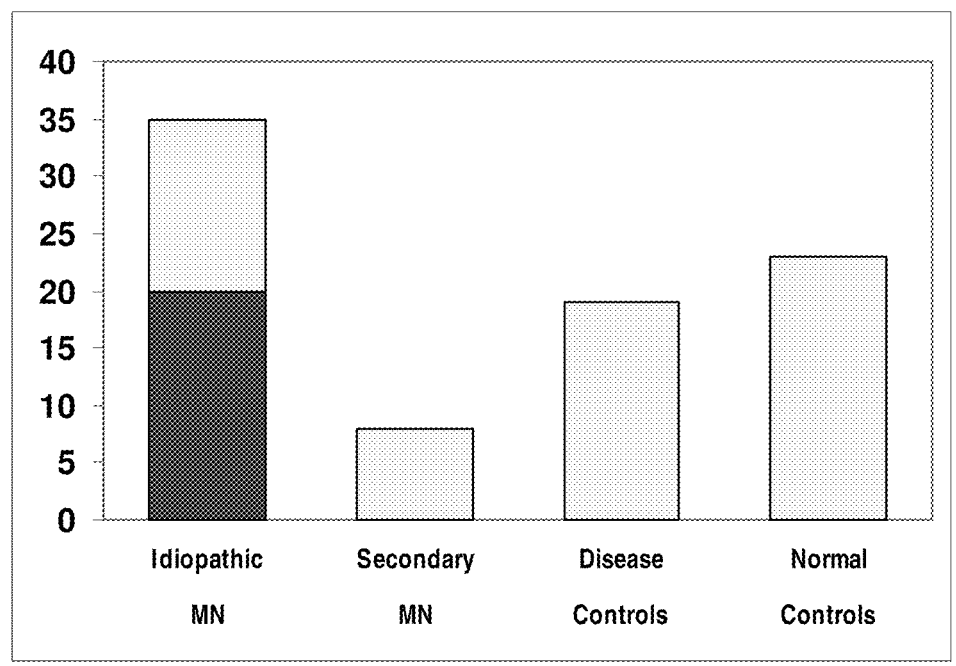

*Fig. 6B*
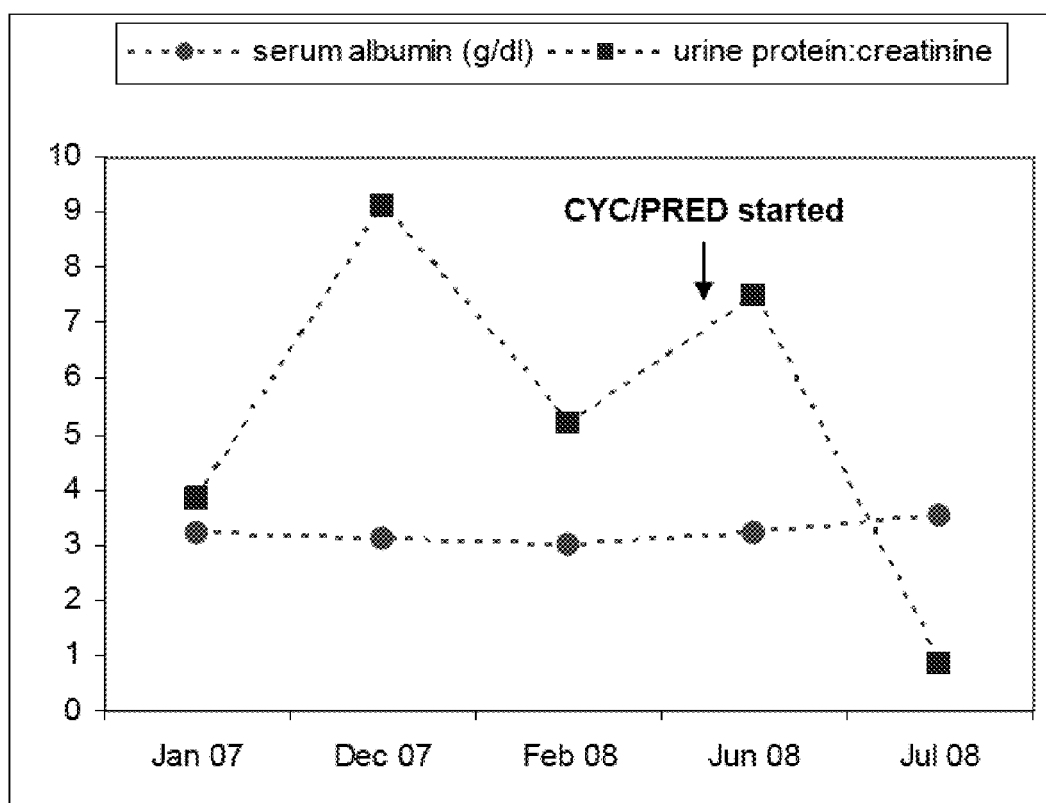
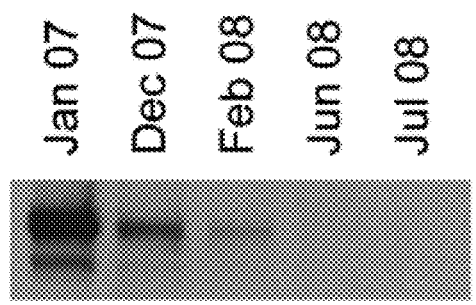

Different principles for antibody assays by the RS-ELISA and the indirect ELISA. Ab, antibody; Ag, antigen.

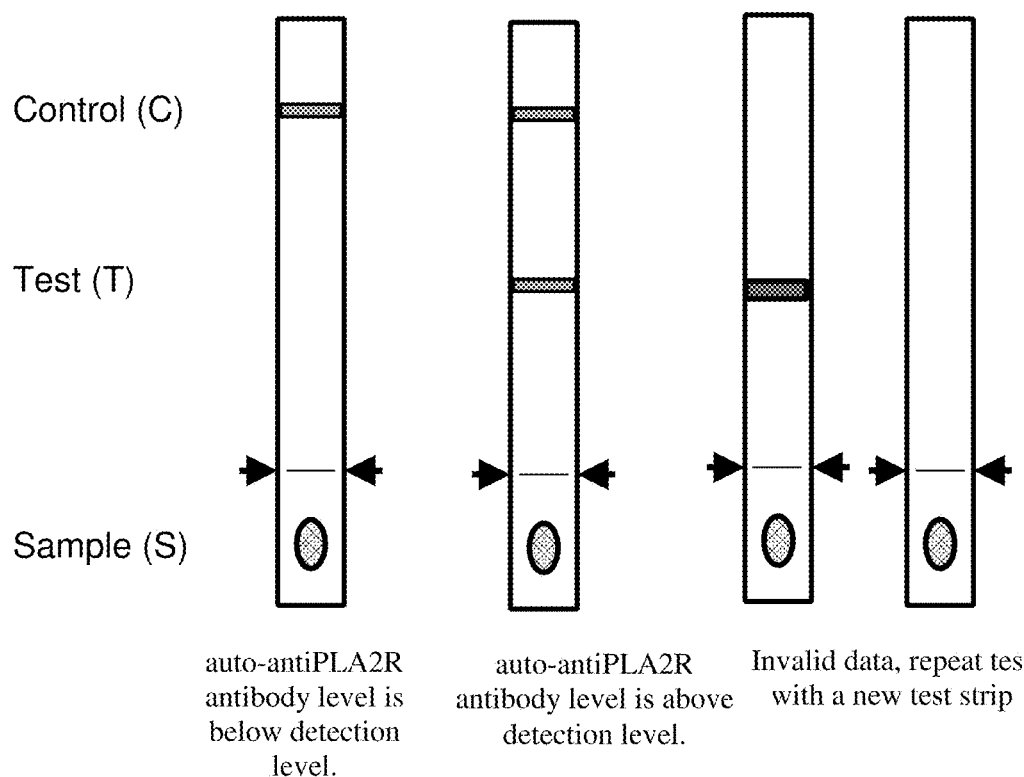

DIAGNOSTICS FOR MEMBRANOUS NEPHROPATHY

CROSS REFERENCE TO RELATED APPLICATION

This application is a continuation application of the International Application No. PCT/US2009/051110 filed on Jul. 20, 2009, which designates the United States, which claims of priority benefit under 35 U.S.C. §119(e) of the U.S. Provisional Application No. 61/081,786 filed Jul. 18, 2008, the contents of which are incorporated herein by reference in their entirety.

GOVERNMENT SUPPORT

This invention was made with Government support under contract No. DK067658 and DK30932 awarded by the National Institute of Health. The Government has certain rights in the invention.

BACKGROUND OF INVENTION

The nephrotic syndrome, characterized by edema and large amounts of protein in the urine, is a relatively common disorder of the kidney that has many potential causes, including membranous nephropathy (MN), focal and segmental glomerulosclerosis, minimal change disease, diabetic nephropathy, membranoproliferative glomerulonephritis, as well as other causes. Although there are non-specific treatments that ameliorate some of the signs and symptoms of the nephrotic condition, specific knowledge of the underlying disease is usually necessary to guide definitive treatment. When a patient with the nephrotic syndrome is initially evaluated as an outpatient or in the hospital, a panel of blood tests is usually ordered by the physician to look for potential causes that are detectable by serology (for example, the presence of anti-nuclear antibodies (ANA) and/or anti-double stranded DNA antibodies in the context of typical findings in the urinary sediment would suggest lupus nephritis). There is currently no serologic test to identify MN, and diagnosis relies exclusively on kidney biopsy, an invasive procedure requiring overnight hospitalization in many institutions and one that can be complicated by major internal bleeding. MN can be caused by a number of secondary factors, such as systemic lupus erythematosus, hepatitis B, or syphilis, and blood tests are routinely sent to look for these causes (ANA, anti-hepatitis B antigens, rapid plasma reagin (RPR), respectively). However, in the United States, MN is more often primary, or idiopathic, in origin and as mentioned above, no blood test for this form currently exists. Therefore, there is a need to identify the underlying cause of MN and develop a simple, non-invasive test to diagnose MN and follow the response to treatment.

SUMMARY OF THE INVENTION

Embodiments of the invention are based on the discovery that the underlying cause of idiopathic membranous nephropathy (MN) is the presence of auto-antibodies against the M-type phospholipase A2 receptor (PLA2R) that is expressed in the kidney glomeruli. The auto-antibodies are predominantly of the IgG4 subclass. In addition, anti-PLA2R auto-antibodies of the subclass IgG1, IgG2, and IgG3 were also present. The sera of individuals having idiopathic MN have detectable amounts of such auto-antibodies. Knowing that the presence of auto-antibodies is associated with MN and that PLA2R is the target of these auto-antibodies has enabled the development of a simple serological immunoassay for diagnosing idiopathic MN. This detection of anti-PLA2R auto-antibodies provides a fast, accurate, cost-effective, safe and non-invasive method of diagnosing idiopathic MN, compared to the current method of a kidney tissue biopsy.

Accordingly, in an embodiment, provided herein is a method of diagnosing MN in a subject, the method comprising detecting the presence of antibodies that are reactive to a PLA2R, wherein the antibodies are found in a sample from a subject. The antibodies can be detected by an immunoassay wherein an antibody-protein complex is formed. The antibodies are found in the sample of the subject, e.g. serum. The subject is a human and the MN is idiopathic. Prior to the diagnosis method, a kidney biopsy is not performed. Healthy individuals have minimal or undetectable anti-PLA2R auto-antibodies by conventional ELISA or Western blots. Individuals with idiopathic MN have significant amount of detectable anti-PLA2R auto-antibodies, at least 10% more anti-PLA2R auto-antibodies detected over that from a healthy non-MN individual or the level obtained for a population of healthy non-MN individuals by conventional ELISA or Western blots as described herein. Moreover the levels of auto-antibodies correspond with the clinical features of the disease condition e.g. proteinuria and nephrotic syndrome. Patients in remission after effective treatment have minimal or undetectable anti-PLA2R auto-antibodies by conventional ELISA or Western blots. As an examplary, by undetectable amount of anti-PLA2R auto-antibodies, it means that no visible band is observed in a Western Blot analysis performed as described in Example 1, wherein human serum is diluted 1:100 and used in blot assays described herein. In one embodiment, the amount of anti-PLA2R auto-antibodies in a healthy non-MN individual or the average amount in a population of healthy non-MN individuals as determined by conventional ELISA or Western blot set forth in Example 1 can be considered as the background, reference or the control level. The collected samples of serum from the healthy non-MN individuals are diluted 1:100 and used in Western blot assays. The intensity of the visible band is quantified by densitometry. The densitometry intensity can be calibrated with a range of known titer of anti-PLA2R antibodies reacting with a fixed amount of antigen PLA2R. For example, the range of known antibody titer can be 0 µg/ml, 0.5 µg/ml, 1.0 µg/ml, 1.5 µg/ml, 2.0 µg/ml, 2.5 µg/ml, 3.0 µg/ml, 5 µg/ml, 7.5 µg/ml, 10 µg/ml, and 15 µg/ml and the fixed amount of PLA2R can be 0.5 µg on a blot. By comparing the densitometry intensity of a human sample with the calibration curve, it is possible to estimate the titer of the anti-PLA2R in nthe sample. For the data collected for a population of individuals, the average value and one order of standard deviation is computed. Ideally, a population has about 25 healthy non-MN individuals, preferably more. The statistics, the average value and one order of standard deviation can be uploaded to the computer system and data storage media. Patients having at least 10% more than this average amount of anti-PLA2R auto-antibodies is likely to have MN, especially if the patient is also presents the clinical significant features of the disease, e.g. proteinuria and nephrotic syndrome.

In one embodiment, the auto-antibodies in the sample are reactive against the PLA2R that has been extracted from mammalian tissues or recombinant mammalian PLA2R, e.g. the human or pig PLA2R. The sample from the subject can be a blood sample. In other embodiments, the sample is a serum or plasma sample.

In one embodiment, the auto-antibodies are detected by a serological immunoassay, such as an enzyme-linked immunosorbant assay or a nephelometric immunoassay.

In an embodiment, provided herein is a method of prognosis evaluation in a subject being treated for membranous nephropathy, the method comprising: (a) determining at a first time point a level of antibodies that are reactive to a PLA2R, wherein the antibodies are found in a sample from a subject; (b) determining at a second time point a level of antibodies that are reactive to a PLA2R, wherein the second time point is after the first time point; and (c) comparing the levels of antibodies of the two time points, wherein a decrease in the level of antibodies in the second time point compared to the first time point indicates that the treatment is effective. The decrease is at least 10%, at least 20%, at least 30%, at least 40%, at least 50%, at least 60%, at least 70%, at least 80%, at least 90%, 100% and all the percentages between 10-100%. The level of the antibodies can be detected by an immunoassay wherein an antibody-protein complex is formed and the complex is detected. The antibodies are found in the sample of the subject, e.g. serum. In an embodiment, the treatment is an immunosuppressive treatment. In one embodiment, the level of antibodies at a later time point, e.g. the second time point, is between 95-100% or more lower compared to the first time point, which is considered below the detection limit of the immunoassay, then the subject is in remission for MN. In one embodiment, below the detection limit of a Western blot is when no visible band is present when the assay is performed according to the method set forth in Example 1.

In an embodiment, provided herein is a method of prognosis evaluation in a subject for membranous nephropathy, the method comprising: (a) determining at a first time point a level of antibodies that are reactive to a PLA2R wherein the antibodies are found in a sample from a subject; and (b) determining at least a second time point a level of antibodies that are reactive to a PLA2R, wherein the second time point is after the first time point; wherein when the in the level of antibodies in the second time point decreases to below the detection limit indicates that there is spontaneous remission. The decrease is at least 10%, at least 20%, at least 30%, at least 40%, at least 50%, at least 60%, at least 70%, at least 80%, at least 90%, 100% and all the percentages between 10-100%. As discussed here, such decreases indicate that the patient is getting better relative to the prior reading. Below the detection limit is when the level of antibodies is reduced to between 95-100% and beyond compared to the first time point. In one embodiment, below the detection limit of a Western blot is when no visible band is observed when the assay is performed according to the method set forth in Example 1.

In one embodiment, when the subject is being treated for MN and the level of antibodies in the second time point is below the detection limit of the immunoassay, then the subject is considered to be in remission for MN.

In an embodiment, provided herein is a method of prognosis evaluation in a subject for membranous nephropathy, the method comprising: (a) determining at a first time point a level of antibodies that are reactive to a PLA2R, wherein the antibodies are found in a sample from a subject; (b) determining at least a second time point a level of antibodies that are reactive to a PLA2R, wherein the second time point is after the first time point; and (c) comparing the levels of antibodies of the first and second time points, wherein an increase in the level of antibodies in the later time point compared to the first time point indicates that there is a relapse of membranous nephropathy. The increase is at least 5%, at least 10%, at least 20%, at least 30%, 50%, at least 100%, at least 200%, at least 300%, at least 500%, at least 1000%, or more and including all the percentages between 10-1000%.

In an embodiment, provided herein is a method of treatment of membranous nephropathy in a subject, the method comprising removing an antibody that is reactive to a PLA2R from a sample in a subject. The antibodies are removed from the blood by immunoabsorption. The sample is returned back into the subject after the removal of the antibodies.

In an embodiment, provided herein is a method of treatment of membranous nephropathy in a subject, the method comprising administering an effective amount of PLA2R or fragments thereof or a vector expressing a PLA2R or fragments thereof.

In one embodiment, provided herein is a composition for the treatment of idiopathic membranous nephropathy, the composition comprising administering a PLA2R or fragments thereof.

In one embodiment, provided herein is a use of an effective amount of PLA2R or fragments thereof or a nucleic acid molecule capable of expressing a PLA2R such as a vector expressing a PLA2R or fragments thereof for the of treatment of membranous nephropathy in a subject.

In another embodiment, provided herein is a use of an effective amount of PLA2R or fragments thereof or a vector expressing a PLA2R or fragments thereof in the manufacture of a medicament for treatment of membranous nephropathy in a subject.

In one embodiment, the fragments suitable for treatment or adsorption are fragments comprising the CTLDs or CRDs 4, 5 6 of PLA2R.

In one embodiment, provided herein is an immunoassay comprising: contacting a sample from a subject with a PLA2R or PLA2R fragment thereof; forming an antibody-protein complex between the antibody present in a sample with the PLA2R or PLA2R fragment thereof; washing to remove any unbound antibody; adding a detection antibody that is labeled and is reactive to the antibody from the sample; washing to remove any unbound labeled detection antibody; and converting the label to a detectable signal, wherein the presence of a detectable signal indicates the likelihood of MN in the subject.

In one embodiment, provided herein is an immunoassay comprising: contacting a sample from a subject with a PLA2R or PLA2R fragment thereof; forming an antibody-protein complex between the antibody present in a sample with the PLA2R or PLA2R fragment thereof; measuring a light scattering intensity resulting from the formation of the antibody-protein complex wherein the light scattering intensity of at least 10% above a control light scattering intensity indicates the likelihood of MN or relapse of MN in the subject. In one embodiment, the control light scattering intensity is that of PLA2R or PLA2R protein fragment in the absence of a sample from the subject. In another embodiment, the control light scattering intensity is that of PLA2R or PLA2R protein fragment in the presence of a sample from a non-MN healthy subject. In another embodiment, the control light scattering intensity is the average light scattering intensity obtained for a population of non-MN healthy subjects. Such subject do not have any clinical features of the disease as described herein. The increase is at least 10%, at least 20%, at least 30%, at least 40%, at least 50%, at least 60%, at least 70%, at least 80%, at least 90%, 100% and all the percentages between 10-100%. In one embodiment, the light scattering intensity is measured in a nephelometer.

In one embodiment, the MN is idiopathic. In other embodiments, the subject is a human, and the sample is a blood sample. In another embodiment, a kidney biopsy is not performed on the subject.

In one embodiment, the PLA2R is a mammalian PLA2R, a human or pig PLA2R protein. In one embodiment, the PLA2R or PLA2R protein fragment thereof is deposited or immobilized on a solid support. In another embodiment, a known amount of a PLA2R or PLA2R protein fragment is deposited or coupled to a solid support. In other embodiments, the support can be in the format of a dipstick, a test strip, a latex bead, a microsphere or a multi-well plate.

In one embodiment, the anti-PLA2R auto-antibodies are of the IgG subclass: IgG1-4. In one embodiment, the detection antibody is labeled by covalently linking to an enzyme, label with a fluorescent compound or metal, or label with a chemiluminescent compound. In another embodiment, the detection antibody is specifically reactive to the subject, for example, if the subject is a human, the detection antibody is specific to human.

In one embodiment, the detectable signal is compared to a set of detectable signals from a titration curve derived from immunoassays of known amounts of PLA2R or fragments in increasing quantity.

In one embodiment, the immunoassay is performed for a plurality of samples from a subject obtained over a period of time. The plurality of samples is obtained every two or three months for at least a two year period. The detectable signal or light scattering intensity of each immunoassay is compared to the detectable signal or light scattering intensity of samples obtained from a prior time point, wherein a reduction of at least 5% of detection signal or light scattering intensity indicates effective treatment of MN in the subject. The decrease is at least 10%, at least 20%, at least 30%, at least 40%, at least 50%, at least 60%, at least 70%, at least 80%, at least 90%, 100% and all the percentages between 10-100%.

In one embodiment, provided herein is a device for identifying the presence or the level of antibodies that are reactive to a PLA2R in a sample from a subject comprising: at least a PLA2R protein or fragments thereof; and at least one solid support wherein the PLA2R protein or fragments thereof is deposited on the support. The PLA2R protein or fragments thereof is deposited on the solid support is immobilized on the support and the solid support is in the format of a dipstick, a test strip, a latex bead, a microsphere or a multi-well plate.

In one embodiment, the device further comprises a second labeled PLA2R protein or fragments thereof which produce a detectable signal. In another embodiment, the device further comprises a detection antibody, wherein the detection antibody is specific for the antibodies that are reactive to a PLA2R in the sample of the subject and the detection antibody produces a detectable signal.

In one embodiment, the devices described herein perform an immunoassay wherein an antibody-protein complex is formed. In one embodiment, the immunoassay is a serological immunoassay. In another embodiment, the immunoassay is a nephrelometric immunoassay In one embodiment, provided herein is the use of the devices described herein for facilitating the diagnosis of MN in a subject, wherein a detectable amount of antibodies that are reactive to a PLA2R indicates likelihood of membranous nephropathy in the subject.

In one embodiment, provided herein are kits comprising devices described herein. In other embodiments, the kits further comprise a detection antibody, wherein the detection antibody is specific for the antibodies that are reactive to a PLA2R in the sample of the subject and produces a detectable signal; a second labeled PLA2R protein or fragments thereof which produces a detectable signal; and/or a nephelometer cuvette.

In one embodiment, provided herein is a system comprising: a measuring module measuring auto-antibody information comprising a detectable signal from an immunoassay indicating the presence or level of antibodies that are reactive to a PLA2R from a sample obtained form a subject; a storage module configured to store data output from the measuring module; a comparison module adapted to compare the data stored on the storage module with reference and/or control data, and to provide a retrieved content, and an output module for displaying the retrieved content for the user, wherein the retrieved content the presence of detectable amount of antibodies reactive against PLA2R indicates that the subject has MN or has a relapse of MN.

In one embodiment, provided herein is a system to facilitate the prognosis evaluation of membranous nephropathy (MN) in a subject, comprising: a determination module configured to receive and output auto-antibody information to a PLA2R from a sample obtained from a subject, wherein the auto-antibodies information measures the level of auto antibodies that are reactive to the PLA2R; a storage module configured to store output information from the determination module; a comparison module adapted to compare the data stored on the storage module with reference data and/or control data, and to provide a comparison content, and an output module for displaying the comparison content for the user, wherein if there is no detectable amount of auto antibodies reactive against PLA2R then the subject is in remission or if there is a reduction of at least 10% to a prior reading, then the treatment for MN is effective in the subject. The reduction is at least 10%, at least 20%, at least 30%, at least 40%, at least 50%, at least 60%, at least 70%, at least 80%, at least 90%, 100% and all the percentages between 10-100%. In one embodiment, the reference or control data comprises previous data from the same subject wherein the previous data had indicated detectable amounts of auto-antibodies, detectable by any conventional ELISA or nephrometric immunoassays described herein and those known in the art. In one embodiment, the reference or control data comprises the average value of anti-PLA2R auto-antibodies and one order of standard deviation obtain from a population of idiopathic MN patients. The collected sera from these idiopathic MN individuals are diluted 1:100 and used in Western blot assays. The intensity of the visible band is quantified by densitometry and the average value and the one order of standard deviation is computed. Ideally, a population has about 25 idiopathic MN individuals, preferably more. The statistics, the average value and one order of standard deviation can be uploaded to the computer system and data storage media.

In one embodiment, provided herein is a computer readable storage medium comprising: a storing data module containing data from a sample obtained from a subject that represents a signal level from an immunoassay for antibodies that are reactive to a PLA2R; a comparison module that compares the data stored on the storing data module with a reference data and/or control data, and to provide a comparison content, and an output module displaying the comparison content for the user, wherein the presence of a detectable amount of antibodies reactive against PLA2R of at least 10% relative to the reference data and/or control data indicates that the subject has MN or has a relapse of MN. The detectable amount is at least 10%, at least 20%, at least 30%, at least 40%, at least 50%, at least 60%, at least 70%, at least 80%, at least 90%, 100%, 200%, 300% or 1000%, including all the percentages between 10-1000%.

In one embodiment, the control data comprises data from a population of non-MN healthy individuals, which is the detection signal obtained using human sera at 1:100 dilution with 1×PBS to immuno-react with 0.5 μg of native PLA2R, wherein horse-radish peroxidase anti-human IgG antibody is the labeled deception antibody and the detection signal is chemiluminescence.

BRIEF DESCRIPTION OF THE DRAWINGS

FIG. 1A shows the sera from patients with idiopathic membranous nephropathy (MN) specifically recognize a 200 kDa glomerular antigen by western blot. Panel (top) shows human glomerular proteins blotted with five different sera from patients with idiopathic MN (lanes MN1-5) or with five sera from patients with other proteinuric conditions (DN, diabetic nephropathy; FS, focal and segmental glomerulosclerosis).

FIG. 1B shows a graphical representation of the specificity of the reactivity of various sera with the 200 kDa antigen. 57% of sera from patients with idiopathic MN react with the glomerular antigen, whereas there are no reactive sera from 8 patients with secondary MN, 19 disease controls (other nephrotic conditions or autoimmune diseases), or 23 normal controls.

FIG. 6B shows that sera reactivity to PLA2R corresponds to disease activity in patient B with idiopathic MN. The graph shows the correlation of decline in protein in urine and the disappearance of anti-PLA2 antibodies prior to and after treatment commencement in the Western Blot.

FIG. 9 shows a schematic diagram showing the interpretation of the results obtained using the test strip shown in FIG. 8.

DETAILED DESCRIPTION OF THE INVENTION

Figure 1C:
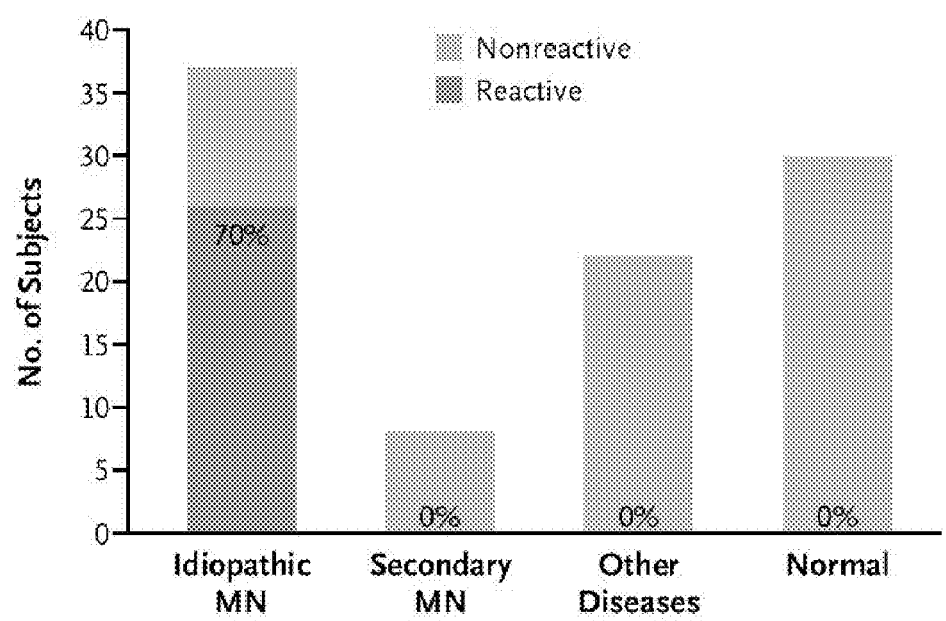
FIG. 1C shows a graphical representation of the specificity of the reactivity of various sera with the 200 kDa (185 kDa) antigen. 72-82% of sera from patients with idiopathic MN from different regions react with the glomerular antigen, whereas there are no reactive sera from 12 patients with secondary MN, 25 disease controls (other nephrotic conditions or autoimmune diseases), or 32 normal controls.

Unless otherwise explained, all technical and scientific terms used herein have the same meaning as commonly understood by one of ordinary skill in the art to which this disclosure belongs. Definitions of common terms in renal diseases, nephrology and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987), Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss, 5th edition (2005), Animal Cell Culture Methods (Methods in Cell Biology, Vol 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

DEFINITIONS OF TERMS

The term "fragment" refers to any subject polypeptide having an amino acid residue sequence shorter than that of a polypeptide whose amino acid residue sequence is described herein. A fragment of PLA2R is a shortened or truncated PLA2R protein. The polypeptide can have N-terminus or C-terminus truncations and/or also internal deletions. Examples of fragments are fragments comprising the CTLDs or CRDs 4, 5 6 of PLA2R. In one embodiment, fragment includes the external domain of PLA2R, which is the amino acid residues 1-1392 of the human PLA2R (SEQ. ID. NO. 2). Shorter portions of 1-1392 are considered fragments.

As used herein, the term "pharmaceutical composition" refers to the active agent in combination with a pharmaceutically acceptable carrier of chemicals and compounds commonly used in the pharmaceutical industry. The term "pharmaceutically acceptable carriers" excludes tissue culture medium.

As used herein, the term "therapeutically effective amount" refers to that amount of active agent that can reduce the amount of soluble auto-antibodies available for binding to PLA2R.

As used herein, the term "treat' or treatment" refers to reducing or alleviating at least one adverse effect or symptom associated with medical conditions that are associated with membranous nephropathy. These include reducing the amount of auto-antibodies against PLA2R protein, reducing, inhibiting or stopping the production of auto-antibodies against PLA2R, suppression of the immune system, and reducing the inflammation and degradation/damage associated with the activities of the auto-antibodies when they are bound to the kidney glomeruli.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human.

As used herein, the term "comprising" means that other elements can also be present in addition to the defined elements presented. The use of "comprising" indicates inclusion rather than limitation.

As used herein, the term "idiopathic MN" is currently used to describe MN that is not caused by any known secondary etiology such as hepatitis B or lupus prior to the present discovery. On the basis of the present discovery, "idiopathic MN" refers to PLA2R-associated MN or any other future designation for what is now called idiopathic MN and is associated with anti-PLA2R antibodies.

The term C-type lectin ("CTLD") or carbohydrate-recognition domain ("CRD") with respect to the domains in PLA2R are used interchangeably.

Embodiments of the invention are based on the discovery that sera of patients with MN contain antibodies that are reactive against the M-type PLA2R that is found in the glomerulus. Idiopathic membranous nephropathy (MN) is considered to be an autoimmune disease targeting the glomerulus, yet the major target antigen has remained elusive. The inventors screened sera from patients with MN for reactivity against human glomerular proteins by western blot (WB) and found a commonly-detected 200 kDa glycoprotein. The inventors then proceeded through partial purification and mass spectrometric analyses to identify this 200 kDa glycoprotein. It is the M-type PLA2R. Soluble and membrane bound isoforms of PLA2R1 (180 kDa) are found. In vivo, PLA2R is expressed in kidneys. This native PLA2R from the glomeruli extract has been further characterized and now is determined to be approximately 185 kDa on a protein gel. Upon deglycosylation in the method described herein, it is approximately 145 kDa.

The inventors found that about 70-82% of patients with MN had antibodies that are reactive with a recombinant PLA2R (rPLA2R) by WB, and the human sera are able to immunoprecipitate (IP) the native protein from extracts of normal human glomeruli. Control sera from normal volunteers and nephrotic controls, as well as sera from MN patients previously non-reactive by WB, do not identify rPLA2R or IP the native protein. The majority of the reactive immunoglobulin in patients' sera is IgG4, the subclass that predominates in glomerular deposits in idiopathic MN. The inventors show that PLA2R is present in podocytes, as detected by immunofluorescence on cyrosections of human kidney. Moreover, both PLA2R and IgG4 co-localize on biopsy specimens from patients with MN in a fine granular pattern typical of the subepithelial deposits characteristic of the disease. While not wishing to be bound by theory, the auto-antibodies in the patients' sera against PLA2R bind to the PLA2R in the kidney glomerulus, causing structural damage to the kidneys and impair kidney function. While not wishing to be bound by theory, the binding of the auto-antibodies to PLA2R cause sublethal injury to the podocytes and induces massive proteinuria. With the major target of idiopathic MN antibodies now being identified as PLA2R, this would allow for earlier and less invasive detection of the disease with an immunoassay designed to measure circulating autoantibodies, and also lead to a means for monitoring response to treatment. In addition, PLA2R auto-antibodies of the IgG1, IgG2, and IgG3 subclasses were also detected. The inventors also found that the auto-antibodies are reactive against mammalian PLA2R, such as the human, rabbit, and pig PLA2R.

The nephrotic syndrome, characterized by edema and large amounts of protein in the urine, is a relatively common disorder of the kidney that has many potential causes, including membranous nephropathy (MN), focal and segmental glomerulosclerosis, minimal change disease, diabetic nephropathy, membranoproliferative glomerulonephritis, as well as other causes. Although there are non-specific treatments that ameliorate some of the signs and symptoms of the nephrotic condition, specific knowledge of the underlying disease is usually necessary to guide definitive treatment. When a patient with the nephrotic syndrome is initially evaluated as an outpatient or in the hospital, a panel of blood tests is usually ordered by the physician to look for potential causes that are detectable by serology (for example, the presence of anti-nuclear antibodies (ANA) and/or anti-double stranded DNA antibodies in the context of typical findings in the urinary sediment would suggest lupus nephritis). There is currently no serologic test to identify MN, and diagnosis relies exclusively on kidney biopsy, an invasive procedure requiring overnight hospitalization in many institutions and one that can be complicated by major internal bleeding. MN can be caused by a number of secondary factors, such as systemic lupus erythematosus, hepatitis B, or syphilis, and blood tests are routinely sent to look for these causes (ANA, anti-hepatitis B antigens, rapid plasma reagin (RPR), respectively). However, in the United States, MN is more often primary, or idiopathic, in origin and as mentioned above, no blood test for this form currently exists, since the antigen targeted in this autoimmune disease had not been identified until this point.

Membranous nephropathy, a frequent cause of adult nephrotic syndrome, is widely felt to be an autoimmune disease despite ignorance of the long-sought target antigen. Much of the support for an autoimmune basis for MN comes from decades of research on the rat model of Heymann nephritis (HN), which is virtually identical at the pathological level to the human disease. In HN, the target antigen is megalin, a molecule in the LDL receptor family that is responsible for semi-selective uptake of proteins in the kidney. It is present, in rats but not in humans, on the podocyte, and circulating antibodies have been shown to bind the protein in situ, leading to shedding of the antibody-antigen complexes into the glomerular basement membrane, leading to the subepithelial deposits characteristic of both HN and MN.

Since the sera from control healthy individuals and non-MN nephropathy patients do not contain or have very very low amount or undetectable amount of auto-antibodies that react with PLA2R unlike the sera of MN patients, the detection of the presence of PLA2R antibodies can be used as a diagnostic tool for MN. A simple blood sample can be used to test for and detect antibodies reactive against PLA2R. Such a method would be highly favorable over the current diagnostic method of a kidney tissue biopsy which is an invasive technique. Accordingly, in one embodiment, provided herein is a method of diagnosing membranous nephropathy in a subject, the method comprising detecting the presence of antibodies that are reactive to a phospholipase A2 receptor, wherein the antibodies are found in a sample from a subject. The antibodies can be detected by an immunoassay wherein an antibody-protein complex is formed. The immunoassay can be a serological immunoassay or a nephelometric immunoassay. The subject is a mammal, such as a dog, a cat, or a human. Healthy subjects who do not have MN or do not have any symptoms related to MN, e.g. protein in the urine, have undetectable auto-antibodies to phospholipase A2 receptor (PLA2R). When antibodies that are reactive to PLA2R are detected in a subject suspected of having MN, e.g. having protein in the urine, the presence of the anti-PLA2R antibodies indicates the likelihood of the subject having MN. As an examplary, by undetectable amount of anti-PLA2R auto-antibodies, it means that no visible band is observed in the Western Blot analysis performed as described in Example 1, wherein human serum is diluted 1:100 and used in blot assays described herein. By very very low amount of anti-PLA2Rauto-antibodies, the low amount is the average amount found in a population of non-MN healthy subjects. The terms "subjects", "individuals" or "patients" are used interchangeably. The amount of anti-PLA2R auto-antibodies in a healthy non-MN individual or a population of healthy non-MN individuals as determined by conventional ELISA or Western blot set forth in Example 1 can be considered as the background, reference or the control level. The collected sera from the healthy non-MN individuals are diluted 1:100 and used in Western blot assays. The intensity of the visible band is quantified by densitometry and the average value and the one order of standard deviation is computed. Ideally, a population has about 25 healthy non-MN individuals, preferably more. The statistics, the average value and one order of standard deviation can be uploaded to the computer system and data storage media. Patients having at least 10% more than this average amount of anti-PLA2R auto-antibodies is likely to have MN, especially if the patient is also presents the clinical features of the disease, e.g. proteinuria and nephrotic syndrome.

In one embodiment, provided herein is an immunoassay comprising: contacting a sample from a subject with a PLA2R or PLA2R fragment thereof; forming an antibody-protein complex between the antibody present in a sample with the PLA2R or PLA2R fragment thereof; washing to remove any unbound antibody; adding a detection antibody that is labeled and is reactive to the antibody from the sample; washing to remove any unbound labeled detection antibody; and converting the label to a detectable signal, wherein the presence of a detectable signal indicates the likelihood of MN in the subject.

In some embodiments, the detection antibody is labeled by covalently linking to an enzyme, label with a fluorescent compound or metal, label with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid.

In one embodiment, the detection antibody is specifically reactive only to the specie of the subject. For example, if the human, then the detection antibody is an anti-human antibody. If the subject is a horse, then the detection antibody is an anti-horse antibody. If the subject is a dog, then the detection antibody is an anti-dog antibody.

In one embodiment, the detectable signal is compared to a set of detectable signals from a titration curve derived from immunoassays of known amounts of PLA2R or fragments in increasing quantity.

In another embodiment, provided herein is an immunoassay comprising: contacting a sample from a subject with a PLA2R or PLA2R fragment thereof; forming an antibody-protein complex between the antibody present in a sample with the PLA2R or PLA2R fragment thereof; measuring a light scattering intensity resulting from the formation of the antibody-protein complex wherein the light scattering intensity of at least 10% above a control light scattering intensity indicates the likelihood of MN or relapse of MN in the subject. The control light scattering intensity is that of PLA2R or PLA2R protein fragment in the absence of sample. In another embodiment, the control light scattering intensity is that of PLA2R or PLA2R protein fragment in the presence of a sample from a non-MN healthy subject. In another embodiment, the control light scattering intensity is the average light scattering intensity obtained for a population of non-MN healthy subjects. In one embodiment, the light scattering intensity is measured in a nephelometer. The increase is at least 20% at least 30%, at least 50%, at least 100%, at least 200%, at least 300%, at least 500%, at least 1000%, or more and including all the percentages between 10-1000%.

In one embodiment, the MN in the subject is idiopathic and a kidney biopsy is not performed on the subject. In one embodiment, the subject is a human and the sample from the subject is a blood sample, e.g. serum or plasma.

In one embodiment, the PLA2R is a mammalian PLA2R, such as human or pig PLA2R.

In one embodiment, the anti-PLA2R antibodies are of the IgG subclass: IgG1-4.

In one embodiment, the immunoassay is a serological immunoassay.

In some embodiments, the PLA2R or PLA2R protein fragment thereof is deposited on a solid support or it can be coupled to immobilize the protein on the support. The support can be is in the format of a dipstick, a test strip, a latex bead, a microsphere or a multi-well plate. In one embodiment, a known amount of a PLA2R or PLA2R protein fragment is deposited or coupled to a solid support. The range of protein is between 0.1 ng-1 mg.

In one embodiment, the immunoassay described herein is performed for a plurality of samples from a subject obtained over a period of time. In one embodiment, the pluralities of samples are obtained every two or three months for at least a two year period. For example, in a blood sample is collected from a patient diagnosed with MN every three months to monitor the progress of the condition and the effectiveness of the immunosuppressive treatment. The result of immunoassay of each blood sample is recorded and the date of sample noted. The result of immunoassay of each blood sample is compared to that obtained for a previous blood sample taken three months earlier. It can also be compared to the results obtained during initial diagnosis before the start of immunosuppressive treatment.

In one embodiment, the detectable signal or light scattering intensity of each immunoassay is compared to the detectable signal or light scattering intensity of a sample obtained from a prior time point, wherein a reduction of at least 5%, at least 10% or more of detectable signal or light scattering intensity indicates effective treatment of MN in the subject, including a reduction of at least 20%, at least 30%, at least 40%, at least 50%, at least 60%, at least 70%, at least 80%, at least 90%, 100% and all the percentages between 10-100%. The prior time point can be the immediate consecutive prior time point or an earlier time point, e.g. six months earlier or that obtained during initial diagnosis before the start of immunosuppressive treatment.

In one embodiment, provided herein is a method of prognosis evaluation in a subject being treated for membranous nephropathy, the method comprising: (a) determining at a first time point in a sample from a subject a level of antibodies that are reactive to a PLA2R; (b) determining at a second time point in a sample from the same subject a level of antibodies that are reactive to a PLA2R, wherein the second time point is after the first time point; and (c) comparing the levels of antibodies obtained for the two time points, wherein a decrease in the level of antibodies in the second time point compared to the first time point indicates that the treatment is effective. The level of the antibodies can be detected by an immunoassay wherein an antibody-protein complex is formed. The subject has initially been diagnosed with MN and has a detectable amount of auto-antibodies against PLA2R. Upon treatment, for example, with immunosuppressive therapy, over time, there is a decrease in the amount of detectable auto-antibodies against PLA2R. In an ideal case, the amount of auto-antibodies should fall below the detectable level of the detection methods described herein and the subject is deemed to be in remission for the disorder. A decrease in the level of antibodies in the second time point compared to the first time point is at least 5%, at least 10%, at least 20%, at least 30%, at least 40%, at least 50%, at least 60%, at least 70%, at least 80%, at least 90%, 100% and all the percentages between 10-100% drop in the titer of auto-antibodies against PLA2R in the serum of second time point compared to the first time point. Below the detection limit is when the level of antibodies is reduced to between 95-100% or more compared to the first time point when the subject was initially diagnosed with MN and no treatment has be implemented. The assay used is identical for all the samples collected different time points from the subject. Decreasing titer of auto antibodies indicate that the treatment is effective in the subject.

In other embodiments, there is no decrease in the level of antibodies in the second time point compared to the first time point. Instead, there can be an increase or a stable level of antibodies.

In one embodiment, there is an increase in antibody level in the second time point compared to the first time point and the first time point has no detectable auto-antibodies. This indicates that the patient has relapsed and the MN has recurred.

In one embodiment, there is an increase in antibody level in the second time point compared to the first time point and the first time point has detectable auto-antibodies. This indicates worsening of the disease and/or lack of efficacious treatment. The increase is at least 30%, at least 50% at least 100%, at least 200%, at least 300%, at least 500%, at least 1000%, or more and including all the percentages between 10-1000%.

In one embodiment, the stable level of antibody, wherein the auto-antibodies detectable at the second and first time points are comparably similar within statistical analysis variances, about 1%, 2%, 3%, 4%, 5% and all the percentages between 1%-5% deviation from the level of auto-antibodies from the first time point. The stable level of antibody indicates stable disease, wherein the treatment has been of insufficient duration (i.e., that it should be continued if clinically indicated) or is ineffective.

As used herein, the term "auto-antibodies" and "antibodies" against PLA2R are used interchangeably.

In other embodiments, the immunoassays comprise beads coated with native or recombinant PLA2R protein as described in Binder S R., Lupus. 2006, 15:412-21. Commonly used are polystyrene beads that are dyed to establish a unique identity. Detection is performed by flow cytometry. Autoantibody detection using multiplex technologies. Other types of bead-based immunoassays are well known in the art, e.g. laser bead immunoassays and related magnetic bead assays (Fritzler, Marvin J; Fritzler, Mark L, Expert Opinion on Medical Diagnostics, 2009, pp. 3: 81-89).

In another embodiment, provided herein is a method of prognosis evaluation in a subject for membranous nephropathy, the method comprising: (a) determining at a first time point in a sample from a subject a level of antibodies that are reactive to a PLA2R; and (b) determining at a subsequent time point, i.e. at a second time point in a sample from the same subject a level of antibodies that is reactive to a PLA2R, wherein the second time point is after the first time point; wherein no detectable auto-antibodies against PLA2R at the second time point compared to the first time point indicates that the subject is in remission for MN. The level of the antibodies can be detected by an immunoassay wherein an antibody-protein complex is formed. The detection limit is when the level of antibodies is reduced to between 95-100% and beyond more compared to that of the first time point.

In a further embodiment, provided herein is a method of prognosis evaluation in a subject for membranous nephropathy, the method comprising: (a) determining at a first time point in a sample from a subject a level of antibodies that are reactive to a PLA2R; (b) determining at a subsequent time point, i.e. at a second time point in a sample from the same subject a level of antibodies that is reactive to a PLA2R, wherein the second time point is after the first time point; and (c) comparing the levels of antibodies of the two time points, wherein an increase of at least 5% in the level of antibodies at the second time point compared to the first time point indicates that there is relapse of MN. The level of the antibodies can be detected by an immunoassay wherein an antibody-protein complex is formed. The increase is at least 10%, at least 20%, at least 30%, at least 50%, at least 100%, at least 200%, at least 300%, at least 500%, at least 1000%, or more and including all the percentages between 10-1000%.

In one embodiment, the subject has been successfully been treated for MN, has no detectable auto-antibodies against PLA2R in blood circulation and is currently not on under any treatment for MN. In this subject, the first time point has no detectable auto-antibodies. The subject had previously been diagnosed with MN and has a detectable amount of auto-antibodies against PLA2R. Upon treatment, for example, with immunosuppressive therapy, over time, the amount of auto-antibodies against PLA2R drops to below the detectable level of the detection methods described herein and the subject is in remission for MN. The re-emergence of a detectable amount of auto-antibodies against PLA2R, and the gradual increase of the auto-antibodies over time indicates that MN has recurred in the subject.

In another embodiment, the subject is currently being treated for MN and has detectable auto-antibodies against PLA2R in blood circulation. An increase in the level of antibodies at the second time point compared to the first time point indicates that the disease condition is deteriorating and the treatment at the current regime is not effective in slowing/stopping the disease.

In another embodiment, the subject is currently being treated for MN, has detectable auto-antibodies against PLA2R in blood circulation and the level of auto-antibodies in the first and second time points are comparably similar within statistical analysis variances. This indicate that the subject has a steady level of auto-antibodies during treatment, indicating that the treatment has been of insufficient duration (i.e., that it should be continued if clinically indicated) or is ineffective.

In one embodiment, the MN is idiopathic. The subject who is being suspected of having MN has tested negative for the usual causes of MN, for example, systemic lupus erythematosus, hepatitis B, and syphilis. A skilled clinician would have, by the process of elimination, ruled out all possible causes for MN. What is left is the tentative diagnosis of MN from an obscure or unknown cause, such as possibly autoimmune auto-antibodies against PLA2R. The non-invasive diagnostic method described herein can then be applied to such a subject for confirmation.

In one embodiment, the method of diagnosing MN described herein is applied to a patient who presents symptoms of MN without having undergone the routine screening to rule out all possible causes for MN. The methods described herein can be part of the routine set of tests performed on a patient who presents symptoms of MN such as proteinuria for diagnostic purposes. The test can be an immunoassay wherein an antibody-protein complex is formed, e.g. serological immunological assays. Such patients have not been biopsied for the confirmatory diagnosis of MN. Similarly, methods described herein can be part of the routine set of serological immunological tests performed for a patient who already is known to have MN by biopsy or by serological testing, is being treated for MN. The methods are useful for the monitoring of immunosuppressive therapies efficacy and prognostic evaluation in the patient.

In one embodiment, the subject is a mammal. In another embodiment, the subject is a human. It is envisioned that the methods described herein are applicable to any mammal that has kidneys, expresses PLA2R and has an immune system that comprises antibodies.

In one embodiment, the subject who is being suspected of having MN has not undergone a kidney biopsy for a confirmatory diagnosis of MN.

The inventors have found that the antibodies in the sera of MN patients were immunologically reactive against mammalian PLA2R such as the human, rabbit and PLA2R. Therefore, encompassed herein, the methods described herein comprise detecting antibodies that are reactive against the human phospholipase A2 receptor or pig PLA2R. As used herein, the term "reactive against", "react to" or "reactive with" refers to the antibodies recognizing the human or pig PLA2R and binding to the PLA2R. The recognition and binding are the standard antibody-antigen interactions that are well characterized by biochemistry and immunology.

In one embodiment, the sample from the subject is a blood sample. In other embodiments, the sample is whole blood, serum, or plasma.

In one embodiment, the antibodies are of the IgG4 subclass. In other embodiments, the PLA2R auto-antibodies are of the subclass IgG3 and IgG1. In yet other embodiments, PLA2R auto-antibodies are of the IgG subclasses: IgG1-4.

In one embodiment, the treatment for MN is an immunosuppressive therapy, for example, cyclosporin, tacrolimus, azathioprine, infliximab, omalizumab, daclizumab, adalimumab, eculizumab, efalizumab, natalizumab, omalizumab and rapamycin. In a further embodiment, the immunosuppressive treatment for MN additionally includes but is not limited to cyclophosphamide, chlorambucil, and rituximab.

In some embodiments, for the methods described herein, the detection of auto-antibodies against PLA2R is performed by a serological immunoassay such as an enzyme-linked immunosorbent assays (ELISAs). ELISAs and other immunoassays known in the art are generally created using standard protocols, with the major variation being the target, or capture, antigen. For the methods described herein, the antigen is human PLA2R, pig PLA2R, or fragments thereof. Recombinant full-length PLA2R expressed in a mammalian or insect cell line can be purified and used as the capture antigen. The protein can be expressed with an N- or C-terminal FLAG tag to facilitate purification from other cell-line derived proteins. ELISA plates will be coated with PLA2R or a fragment at a constant concentration. The plate can be blocked with bovine casein or serum albumin or other blocking agents to prevent nonspecific binding of the samples. Human serum to be tested can be added to the wells at standard dilutions (1:40, 1:80, 1:160, etc.) followed by routine washes. Bound IgG can be detected with a secondary anti-human IgG antibody linked to horseradish peroxidase. After a series of washes, colorimetric substrate can be added to all wells and developed. The ELISA plate can be read on a micro titer plate reader. Using MN serum samples that are known to be positive or negative, as well as serum from normal human volunteers, it is possible to establish appropriate cut-off titers to define what will constitute a positive test result. Healthy subjects who do not have MN or do not have any symptoms related to MN, e.g. protein in the urine, have undetectable auto-antibodies to PLA2R. When antibodies that are reactive to PLA2R are detected in a subject suspected of having MN, e.g. having protein in the urine, the presence of the anti-PLA2R antibodies indicates the likelihood of the subject having MN.

In one embodiment, an ELISA can provide a simple serological assay for immunologically-active MN, i.e. active MN with auto-antibodies against PLA2R. The simple serological assay can be ordered with other widely used diagnostic or otherwise informative blood tests in patients with heavy proteinuria, such as anti-nuclear antibodies, anti-hepatitis-B and -C antibodies, and complement C3 and C4 levels. In the cases of patients who test positive in this assay, biopsy of the kidney may not be necessary to guide treatment, unless other atypical features are present that might warrant a biopsy. In those patients who test negative and still have unexplained proteinuria, however, a renal biopsy is still indicated. An immunoassay as described can be considerably cheaper than renal biopsy, which often requires an overnight admission to the hospital. It is also much more convenient for both the patient and physician.

It is a known fact that proteinuria can persist (transiently or permanently) in MN patients even after the immunological disease is over, due to structural changes in the glomerulus. Reliance on levels of protein excretion alone can lead to the treatment of patients with toxic immunosuppressive drugs much longer than necessary. Thus, monitoring for disappearance of auto antibodies with the described ELISA will help define a transition point in the treatment of membranous nephropathy when immunosuppressive therapy should be stopped but anti-proteinuric therapy (e.g., angiotensin-converting enzyme inhibitors) should be continued.

In one embodiment, provided herein is a method of treatment of membranous nephropathy in a subject, the method comprising administering an effective amount of PLA2R or fragments thereof or a vector expressing a PLA2R or fragments thereof. By providing soluble PLA2R or fragments thereof, the soluble protein can function as decoy antigens and sequester the auto-antibodies away from the PLA2R in the renal glomeruli, thereby reducing the potential damage to the kidney. The PLA2R can be the human or pig PLA2R. In one embodiment, the fragments suitable for treatment or adsorption of the auto-antibodies to PLA2R from the serum are fragments comprising the CTLDs or CRDs 4, 5 6 of PLA2R. In another embodiment, the fragments comprise the extracellular domain of human or pig PLA2R. In one embodiment, the fragment is SEQ. ID. NO. 5 or smaller portions of SEQ. ID. NO. 5, such as at least 10%, at least 20%, at least 30%, at least 40%, at least 50%, at least 60%, at least 70%, at least 80%, at least 90%, at least 95 including all the percentages between 10-95%. Also comtempted are peptides between 10-50 amino acid residues derived on the sequence of SEQ. ID. NO. 5 that can be used in the treatment of MN. In one embodiment, a cocktail of several peptides is used for treatment. Envisioned peptides can be fused with other proteins for longer serum half-life, tandemly linked peptides or circular peptides.

In one embodiment, the membranous nephropathy is idiopathic. The subject has tested positive for antibodies reactive against a PLA2R. In one embodiment, the auto-antibodies are reactive to the human PLA2R or pig PLA2R.

In another embodiment, provided herein is a method of treatment of membranous nephropathy in a subject, the method comprising removing an antibody that is reactive to a PLA2R from a sample in a subject. The antibodies are removed from the blood by immunoabsorption with PLA2R or fragments thereof as the antigen, and the sample is returned back into the subject after the removal of the antibodies. The fragments suitable adsorption are fragments comprising the CTLDs or CRDs 4, 5 6 of PLA2R. For the human PLA2R receptor 1 isoform 1 precursor (GENBANK™ Accession No. NP_031392.3, SEQ. ID. NO. 2), a suitable fragment can be amino acid residues 650 to 1100 which consist of the CRDs 4, 5 6 of PLA2R.

In one embodiment, provided herein is a use of an effective amount of PLA2R or fragments thereof or a vector expressing a PLA2R or fragments thereof for the of treatment of membranous nephropathy in a subject.

In one embodiment, provided herein is a use of an effective amount of PLA2R or fragments thereof or a vector expressing a PLA2R or fragments thereof in the manufacture of a medicament for treatment of membranous nephropathy in a subject.

In one embodiment, the sample is blood. In other embodiments, the sample is serum or plasma. In one embodiment, the subject is a human and the membranous nephropathy is idiopathic. The auto-antibodies are reactive to the human PLA2R or the pig PLA2R receptor. In one embodiment, the antibodies are of the IgG4 subclass. In other embodiments, the PLA2R auto-antibodies are of the subclass IgG3, IgG2, and IgG1. In yet other embodiments, PLA2R auto-antibodies are of the IgG subclasses: IgG1-4. The immunoabsorption of auto-antibodies against PLA2R helps reduce the amount of circulating auto-antibodies and thereby reducing the potential damage to the kidney. This treatment can be applied initially after immunological confirmation of the presence of the auto-antibodies reactive against PLA2R and before the start of any immunosuppressive therapy. This is especially useful during this early period before the immunosuppressive therapy can have an effect on the immune system and production of auto-antibody in the subject.

In one embodiment, immunoabsorption of auto-antibodies against PLA2R can occur by passing the blood, serum or plasma over immobilized PLA2R. Recombinant human or pig PLA2R or fragments can be immobilized on inert and sterile matrices that are known in the art, such as sepharose. The auto-antibodies against PLA2R will bind to the immobilized PLA2R or fragments and remind bound to the matrix indirectly. The blood, serum or plasma is then collected. This resultant blood, serum or plasma should have no detectable or reduced auto-antibodies against PLA2R. The immunoabsorption procedure should be conducted under sterile conditions. The collect blood, serum or plasma that is now depleted of auto-antibodies against PLA2R can now be transfused back into the patient.

Devices, Kits, Computer System and Computer Data Storage

In one embodiment, provided herein are devices for identifying the presence or the level of antibodies that are reactive to a PLA2R in a sample from a subject comprising: at least a PLA2R protein or fragments thereof; and at least one solid support wherein the PLA2R protein or fragments thereof is deposited on the support. In one embodiment, the PLA2R protein or fragments thereof that is deposited on the solid support is immobilized on the support. In one embodiment, the PLA2R protein is a human or pig PLA2R protein. In one embodiment, the solid support is in the format of a dipstick, a test strip, a latex bead, a microsphere or a multi-well plate.

In one embodiment, the subject is a human and a kidney biopsy is not performed in the subject. In one embodiment, the sample from the subject is a blood sample.

In other embodiments, the devices or kits described herein can further comprise a second labeled PLA2R protein or a fragment thereof which produces a detectable signal; a detection antibody, wherein the detection antibody is specific for the antibodies that are reactive to a PLA2R in the sample of the subject and the detection antibody produces a detectable signal; or a nephelometer cuvette.

In one embodiment, the device performs an immunoassay wherein an antibody-protein complex is formed, such as a serological immunoassay or a nephelometric immunoassay In some aspects, the devices described herein facilitate the diagnosis of membranous nephropathy in a subject, wherein a detectable amount of antibodies that are reactive to a PLA2R indicates likelihood of membranous nephropathy in the subject.

In one embodiment, provided herein are kits that comprise devices described herein and a detection antibody, wherein the detection antibody is specific for the antibodies that are reactive to a PLA2R in the sample of the subject and produces a detectable signal. In one embodiment, the kit can include a second labeled PLA2R protein or a fragment thereof which produces a detectable signal. In further embodiments, the kit includes a nephelometer cuvette.

Any solid support can be used, including but not limited to, nitrocellulose membrane, nylon membrane, solid organic polymers, such as polystyrene, or laminated dipsticks such as described in U.S. Pat. No. 5,550,375. The use of "dip sticks" or test strips and other solid supports have been described in the art in the context of an immunoassay for a number of antigens. Three U.S. patents (U.S. Pat. No. 4,444,880, issued to H. Tom; U.S. Pat. No. 4,305,924, issued to R. N. Piasio; and U.S. Pat. No. 4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. The "dip stick" technology can be easily adapted for the present invention by one skilled in the art. In the invention described herein, the antigen PLA2R is deposited on the support and the auto-antibody is to be detected.

Examples of kits include but are not limited to ELISA assay kits, and kits comprising test strips and dipsticks. In an ELISA kit, an excess amount of PLA2R antigen, in, is immobilized on a solid support. A sample containing an unknown amount of auto-antibodies to PLA2R is added to the immobilized PLA2R, resulting in the formation of a complex consisting of the protein and the antibody. The complex is detected by a labeled second antibody that is also specific for the auto-antibody. The amount of label detected is a measure of the amount of auto antibody present in the sample (see example 3).

In some embodiments of the kits described herein, the kit comprises a test strip or a dipstick.

In some embodiments of the kits described herein, the labeled antibodies are detectably labeled by enzyme labeling, fluorescent labeling, biotin labeling or radioisotope labeling. Other labels include but are not limited to colloidal gold and latex beads. The latex beads can also be colored. Method of labeling antibodies are known in the art, for example, as described in "Colloidal Gold. Principles. Methods and Applications", Hayat M A (ed.) (1989-91). Vols 1-3, Academic press, London; in "Techniques in Immunocytochemistry", Bullock G R and Petrusz P (eds) (1982-90) Vols 1, 2, 3, and 4, Academic Press, London; in "Principles of Biological Microtechnique", Baker J R (1970), Methuen, London; Lillie R D (1965), Histopathologic Technique and practical Histochemistry, 3rd ed, McGraw Hill, New York; Berryman M A, et al (1992), J. Histochem Cytochem 40, 6, 845-857, all of which are incorporated hereby reference in their entirety.

In a typical colloidal gold labeling technique, the unique red color of the accumulated gold label, when observed by lateral or transverse flow along a membrane on which an antigen is captured by an immobilized antibody, or by observation of the red color intensity in solution, provides an extremely sensitive method for detecting sub nanogram quantities of proteins in solution. A colloidal gold conjugate consists of a suspension of gold particles coated with a selected protein or macromolecule (such as an antibody or antibody-based moiety). The gold particles may be manufactured to any chosen size from 1-250 nm. This gold probe detection system, when incubated with a specific target, such as in a tissue section, will reveal the target through the visibility of the gold particles themselves. For detection by eye, gold particles will also reveal immobilized antigen on a solid phase such as a blotting membrane through the accumulated red color of the gold sol. Silver enhancement of this gold precipitate also gives further sensitivity of detection. Suppliers of colloidal gold reagents for labeling are available from SPI-MARK™. Polystyrene latex Bead size 200 nm colored latex bead coated with antibody SIGMA ALDRICH®, Molecular Probes, Bangs Laboratory Inc., and AGILENT® Technologies.

In other embodiments of the kits described herein, at least one of the labeled antibodies comprises an enzyme-labeled antibody. The anti-PLA2R that is bound and captured by the immobilized PLA2R on the solid support (e.g. microtiter plate wells) is identified by adding a chromogenic substrate for the enzyme conjugated to the anti-antibody, e.g. anti-human IgG, and color production detected by an optical device such as an ELISA plate reader.

Other detection systems can also be used, for example, a biotin-streptavidin system. Quantification is determined using a streptavidin-peroxidase conjugate and a chromagenic substrate. Such streptavidin peroxidase detection kits are commercially available, e.g. from DAKO; Carpinteria, Calif.

Detection antibodies and PLA2R can alternatively be labeled with any of a number of fluorescent compounds such as fluorescein isothiocyanate, europium, lucifer yellow, rhodamine B isothiocyanate (Wood, P. In: Principles and Practice of Immunoassay, Stockton Press, New York, pages 365-392 (1991)) for use in immunoassays. In conjunction with the known techniques for separation of antibody-antigen complexes, these fluorophores can be used to quantify the level of auto antibodies. The same applies to chemiluminescent immunoassay in which case antibody or PLA2R can be labeled with isoluminol or acridinium esters (Krodel, E. et al., In: Bioluminescence and Chemiluminescence: Current Status, John Wiley and Sons Inc. New York, pp 107-110 (1991); Weeks, I. et al., Clin. Chem., 29:1480-1483 (1983)). Radio-immunoassay (Kashyap, M. L. et al., J. Clin. Invest., 60:171-180 (1977)) is another technique in which detection antibody can be used after labeling with a radioactive isotope such as $^{125}$I. Some of these immunoassays can be easily automated by the use of appropriate instruments such as the IMX™ (Abbott, Irving, Tex.) for a fluorescent immunoassay and Ciba Corning ACS 180™ (Ciba Corning, Medfield, Mass.) for a chemiluminescent immunoassay.

In some embodiments, the kits described herein further comprise standards of known amounts of the PLA2R or fragments thereof.

In some embodiments, the kits described herein further comprise reference values of the levels of anti-PLA2R antibodies. The reference values are average levels of anti-PLA2R antibodies in samples from a population of non-MN healthy humans. Reference values can be provided as numerical values, or as standards of known amounts or titer of anti-PLA2R antibodies presented in pg/ml-μg/ml.

In some embodiments, the kits described herein further comprise at least one sample collection container for sample collection. Collection devices and container include but are not limited to syringes, lancets, BD VACUTAINER® blood collection tubes.

In some embodiments, the kits described herein further comprise instructions for using the kit and interpretation of results. For example, a chart showing FIG. 9 interpretation of results.

Figure 11:
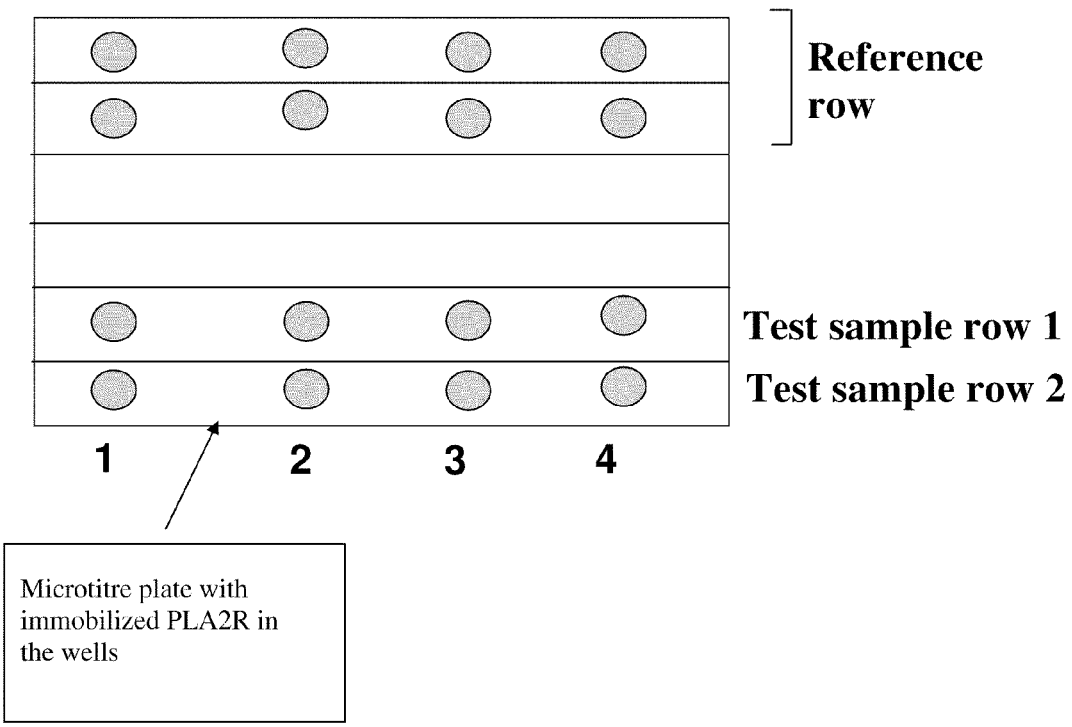
FIG. 11 shows a schematic diagram of a modified ELISA plate assay utilizing fixed amounts of standard PLA2R protein.
Figure 12:
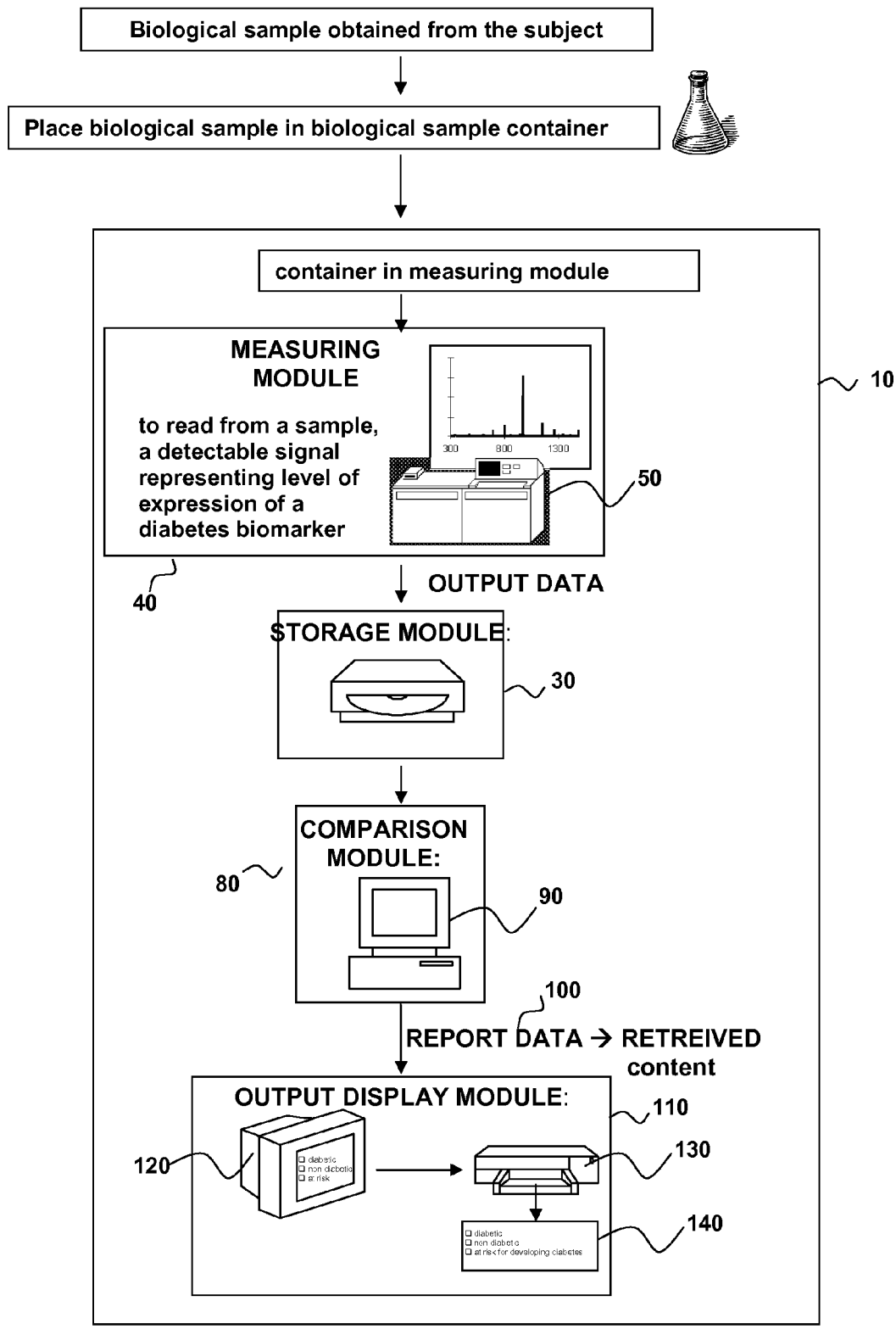
FIG. 12 is a block diagram showing an exemplary system for MN diagnosis.
Figure 13:
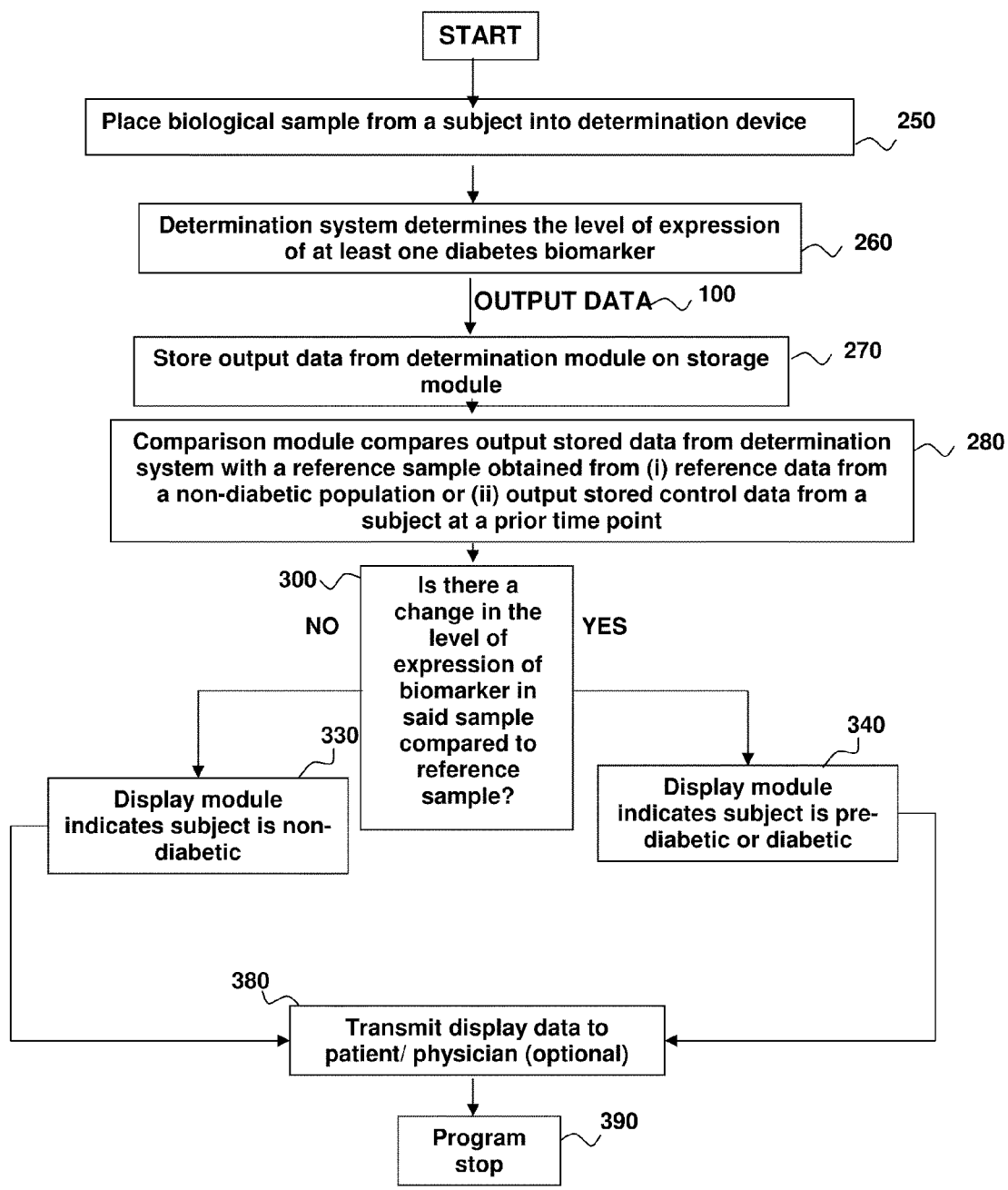
FIG. 13 is an exemplary set of instructions on a computer readable storage medium for use with the systems described herein.

As an exemplary, a typical ELISA-based kit assay would involved dispensing a sample containing the serum into microtiter plate wells, preferably in duplicates or triplicates (as in FIG. 11). The wells are coated with immobilized PLA2R. In addition, a fixed amount of the standard anti-IgG provided with the kit is also dispensed into reference wells in the microtiter plate, also preferably in duplicates or triplicates, according the kit's instruction. That fixed amount of the standard anti-IgG corresponding to at least two fold of the reference value of the anti-PLA2R auto-antibodies normally present in healthy subjects. A second fixed amount of the standard anti-IgG corresponding to two fold lower than of the reference value of the anti-PLA2R auto-antibodies can be added to another set of reference wells. Subsequently, the labeled detection antibody specific for that anti-PLA2R auto-antibodies is added to both sample and reference wells, e.g. an anti-IgG antibody. This is a "sandwich" ELISA assay, where the anti-PLA2R auto-antibodies is sandwich between PLA2R and an anti-IgG antibody. Since the amount of label detected is a measure of the amount of anti-PLA2R auto-antibodies present in the wells, the amounts of label detected in the various wells provides means for comparing the level of the anti-PLA2R auto-antibodies in the sample with the reference value of the anti-PLA2R auto-antibodies normally present in healthy subject. For example, if the label is colored latex beads, greater color intensity in the sample wells compared to the reference wells indicates that the level of anti-PLA2R auto-antibodies in the sample is higher than two fold of the reference value of the anti-PLA2R auto-antibodies normally present in healthy subject. On the other hand, if the color intensity in the sample wells is lower compared to the reference well, that indicate that the level of the anti-PLA2R auto-antibodies in the sample is at least two fold lower than of the reference value of the auto-antiPLA2R antibody normally present in healthy subject.

Embodiments of the invention also provide for systems (and computer readable media for causing computer systems) to perform a method for diagnosing MN in a subject, assessing a subject's risk of developing MN, or monitoring treatment efficacy of a subject with MN.

In one embodiment, provided herein is a system comprising: a measuring module measuring auto-antibody information comprising a detectable signal from an immunoassay indicating the presence or level of antibodies that are reactive to a PLA2R from a sample obtained form a subject; a storage module configured to store data output from the measuring module; a comparison module adapted to compare the data stored on the storage module with reference and/or control data, and to provide a retrieved content, and an output module for displaying the retrieved content for the user, wherein the retrieved content the presence of detectable amount of antibodies reactive against PLA2R indicates that the subject has MN or has a relapse of MN.

In one embodiment, provided herein is a system to facilitate the prognosis evaluation of membranous nephropathy (MN) in a subject, comprising: a determination module configured to receive and output auto-antibody information to a PLA2R from a sample obtained from a subject, wherein the auto-antibodies information measures the level of auto anti-bodies that are reactive to the PLA2R; a storage module configured to store output information from the determination module; a comparison module adapted to compare the data stored on the storage module with reference and/or control data, and to provide a comparison content, and an output module for displaying the comparison content for the user, wherein if there is no detectable amount of auto antibodies reactive against PLA2R then the subject is in remission or if there is a reduction of at least 10% to a prior reading, then the treatment for MN is effective in the subject.

In some embodiments, the control data comprises previous data from the same subject wherein the previous data had indicated detectable amounts of auto-antibodies.

In one embodiment, provided herein is a computer readable storage medium comprising: a storing data module containing data from a sample obtained from a subject that represents a signal level from an immunoassay for antibodies that are reactive to a PLA2R; a comparison module that compares the data stored on the storing data module with a reference data and/or control data, and to provide a comparison content, and an output module displaying the comparison content for the user, wherein the presence of a detectable amount of antibodies reactive against PLA2R of at least 10% relative to the reference data and/or control data indicates that the subject has MN or has a relapse of MN.

In one embodiment, the control data comprises data from a population of non-MN healthy individuals which is the detection signal obtained using human sera from non-MN healthy individuals at 1:100 dilution with 1×PBS to immuno-react with 0.5 μg of native PLA2R, wherein horse-radish peroxidase anti-human IgG antibody is the labeled detection antibody and the detection signal is chemiluminescence.

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media #30 can be any available tangible media that can be accessed by a computer. Computer readable storage media includes volatile and non-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a measuring module #40, a storage module #30, a comparison module #80, and a output module #110. The functional modules can be executed on one, or multiple, computers, or by using one, or multiple, computer networks. The measuring module has computer executable instructions to provide e.g., expression information in computer readable form.

The measuring module #40, can comprise any system for detecting a signal representing expression level of anti-PLA2R auto-antibodies. Such systems can include DNA microarrays, RNA expression arrays, any ELISA detection system and/or any Western blotting detection system.

The information determined in the determination system can be read by the storage module #30. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon expression level or protein level information. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In one embodiment the reference data stored in the storage module to be read by the comparison module is e.g., expression data obtained from a population of non-MN subjects, a population of MN subjects or expression data obtained from the same subject at a prior time point using the measuring module #40.

The "comparison module" #80 can use a variety of available software programs and formats for the comparison operative to compare expression data determined in the measuring module to reference samples and/or stored reference data. In one embodiment, the comparison module is configured to use pattern recognition techniques to compare information from one or more entries to one or more reference data patterns. The comparison module may be configured using existing commercially-available or freely-available software for comparing patterns, and may be optimized for particular data comparisons that are conducted. The comparison module provides computer readable information related to normalized expression level of auto-antibodies, presence/absence of MN in an individual, efficacy of treatment in an individual, and/or method for treating an individual.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content-based in part on the comparison result that may be stored and output as requested by a user using an output module #110.

The content based on the comparison result, may be an expression value compared to a reference showing the presence/absence of MN in an individual or an assessed risk of a subject to develop MN.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The present invention therefore provides for systems (and computer readable media for causing computer systems) to perform methods for diagnosing MN or assessing treatment prognosis of MN in an individual.

Systems and computer readable media described herein are merely illustrative embodiments of the invention for detecting anti-PLA2R autoantibodies in an individual, and are not intended to limit the scope of the invention. Variations of the systems and computer readable media described herein are possible and are intended to fall within the scope of the invention.

The modules of the machine, or those used in the computer readable medium, may assume numerous configurations. For example, function may be provided on a single machine or distributed over multiple machines.

Sample Collection and Preparation

Collections of samples can be performed by methods well known to those skilled in the art.

For example, the patient's blood can be drawn by trained medical personnel directly into anti-coagulants such as citrate and EDTA. The whole blood can be separated into the plasma portion, the cells, and platelets portion by refrigerated centrifugation at 3500×G for 2 minutes. After centrifugation, the supernatant is the plasma.

Alternately, the serum can be collected from the whole blood. Collect the blood in a hard plastic or glass tube; blood will not clot in soft plastic. Draw 15 mL of whole blood for 6 mL of serum. The whole blood is allowed to stand at room temperature for 30 minutes to 2 hours until a clot has formed. Carefully separate clot from the sides of the container using a glass rod or wooden applicator stick and leave overnight at 4° C. After which, decant serum, centrifuge, and/or using a Pasteur pipette, remove serum into a clean tube. Clarify the serum by centrifugation at 2000-3000 rpm for 10 minutes. The serum is stored at −20° or −80° C. before analysis for auto-antibodies against PLA2R is performed. Detailed description of obtaining serum using collection tubes can be found in U.S. Pat. No. 3,837,376 and is hereby incorporated by reference in it entirety. Blood collection tubes can also be purchased from BD Diagnostic Systems, Greiner Bio-One, and Kendall Company.

Detection of PLA2R Antibodies

The detection of auto-antibodies against human or pig PLA2R in blood, serum or plasma can be detected by any method known in the art. Preferably by ELISA, wherein the detection method is an immunochemical method involving the binding of the auto-antibodies with a PLA2R protein or fragments thereof. Formation of the antibody-protein complex is then detected by a variety of methods known in the art.

Figure 7:
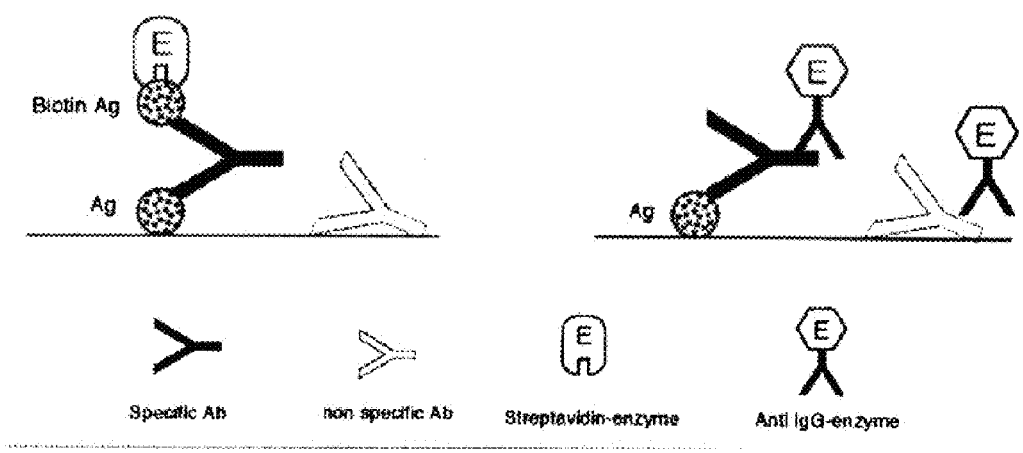
FIG. 7 shows schematic diagrams showing the reverse-sandwich ELISA (RS-ELISA) and indirect ELISA.

Enzyme-linked immunosorbent assay, also called ELISA, enzyme immunoassay or EIA, is a biochemical technique used mainly in immunology to detect the presence of an antibody or an antigen in a sample. The ELISA has been used as a diagnostic tool in medicine and plant pathology, as well as a quality control check in various industries. For the methods described herein, in the ELISA a known amount of antigen (PLA2R or fragments thereof) is affixed to a surface, and then the sample, e.g. blood, serum or plasma, suspected of containing auto-antibodies to PLA2R, is washed over the surface so that the auto-antibodies can bind to the immobilized antigen. The surface is washed to remove any unbound protein and a detection antibody is applied to the surface. The detection antibody is specific to antibodies from the subject. For example, if the subject is a human, the detection antibody should be an anti-human IgG antibody. If the subject is a dog, the detection antibody then should an anti-dog IgG antibody. This detection antibody is linked to an enzyme, and in the final step a substance is added that the enzyme can convert to some detectable signal. For example, in the case of fluorescence ELISA, when light is shone upon the sample, any antigen/antibody complexes will fluoresce so that the amount of antibodies in the sample can be measured. This is the indirect enzyme-linked immunosorbent assay. A schematic diagram of the indirect ELISA is shown in FIG. 7.

The following is a general standard protocol for setting up and performing an indirect enzyme-linked immunosorbent assay. Using 96-well microliter plates (Falcon Pro-Bindassay plate 3915; Becton Dickinson, Paramus, N.J.), test wells are coated with antigen (PLA2R or fragments thereof) by incubation with 100 µl of purified PLA2R (3 µg/ml in PBS) per well overnight at room temperature, with PBS substituted for the antigen in control wells. After the plates have been washed three times with PBS-TWEEN-20®, 250 µl of 2% BSA in PBS is added to each well, and the plates are incubated for 1 h at room temperature. The plates are washed three times with PBS-TWEEN-20® and incubated for 1 h at room temperature with test sera and control sera (one high-positive serum specimen, two negative serum specimens, and one weak-positive serum specimen) diluted 1:100 in PBS-TWEEN-20®-BSA; each serum specimen is tested in triplicate in antigen-coated wells as well as in antigen control wells. The plate is then assayed (with appropriate controls) for the presence of human auto-antibodies IgG against PLA2R by incubation for 1 h at room temperature with 100 µl of goat anti-human IgG conjugated with horseradish peroxidase (Bio-Rad, Richmond, Calif.) per well diluted 1:2,000 in PBS-TWEEN-20®-BSA. After three washes in PBS-TWEEN-20®, the substrate solution (o-phenylenediamine dihydrochloride; Sigma) is added to each well. The plates are then incubated for 30 min at room temperature in darkness, and the reaction is terminated by the addition of 2N sulfuric acid. The optical density values at 490 nm ($OD_{490}$) are measured in a micro plate ELISA reader. For each serum specimen, mean $OD_{490}$ readings are calculated for the test wells and for the antigen control wells, the latter being subtracted from the former to obtain the net ELISA value.

Performing an ELISA involves at least one antibody with specificity for a particular antigen. A known amount of antigen (PLA2R) is immobilized on a solid support (usually a polystyrene micro titer plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody which is linked to an enzyme through bio-conjugation. Between each step the plate is typically washed with a mild detergent solution to remove any proteins or antibodies that are not specifically bound. After the final wash step the plate is developed by adding an enzymatic substrate to produce a visible signal, which indicates the quantity of antigen in the sample. Older ELISAs utilize chromogenic substrates, though newer assays employ fluorogenic substrates with much higher sensitivity.

In another embodiment, a competitive ELISA is used. Purified anti-PLA2R antibodies that are not derived from the subject are coated on the solid phase of multi-wells. Serum sample recombined PLA2R, (the antigen) or fragments thereof and horseradish peroxidase labeled with anti-PLA2R antibodies (conjugated) are added to coated wells, and form competitive combination. After incubation, if the auto-antibody level against PLA2R content is high in the sample, a complex of PLA2R-auto-antibodies-anti-PLA2R labeled with HRP will form. Wash wells will remove the complex, and incubate with TMB (3,3',5,5'-tetramethylbenzidene) color development substrate for localization of horseradish peroxidase-conjugated antibodies in the wells. Subsequently there will be no color change or little color change. If there are no auto-antibodies against PLAR2 in the serum sample, there will be much color change. Such a competitive ELSA test is specific, sensitive, reproducible and easy to operate.

In one embodiment, the reverse-sandwich (RS) ELISA is used (Miyazawa H., et. al, J Allergy Clin Immunol. 1988; 82:407-413), wherein the antibody of interest, in the methods described herein, the auto-antibodies against PLA2R, is sandwiched by antigens (PLA2R): one antigen is affixed to a surface and the second antigen is soluble and tagged. This method is also known as the double-antigen sandwich method. A schematic diagram of the RS ELISA is shown in FIG. 7.

The following is a general standard protocol for setting up and performing a RS-ELISA. A 0.1-ml quantity of PLA2R (0.3 µg/ml) or PLA2R (0.9 µg/ml) plus bovine serum albumin (BSA; 25 µg/ml) in 0.5 M NaCl—0.1% $NaN_3$—0.05 M sodium carbonate (pH 9.6) is added to wells of Maxisorp microplates (Nalge Nunc, Copenhagen, Denmark). The plates are incubated overnight at 4° C. for antigen immobilization. After the wells are washed test sera diluted 1:4, 1:40, and 1:400 with FBS-PBST (10% [vol/vol] fetal bovine serum [FBS], 0.1% $NaN_3$—phosphate-buffered saline [PBS]—0.05% TWEEN-20® [PBST]) are added, and the plates are incubated for 60 min at room temperature. Seven threefold serial dilutions of the reference serum are used. After another wash, biotinylated PLA2R or PLA2R (0.05 µg/ml) in FBS-PBST is then added to the wells, and the reaction is allowed to take place for 60 min at room temperature. The wells are washed again, streptavidin-conjugated β-d-galactosidase (GIBCO BRL, Life Technologies Inc., Rockville, Md.; diluted 1:50,000 in PBST containing 1% BSA) is added, and the plates are incubated for 60 min at room temperature. After another wash, 0.2 mM 4-methylumbelliferyl-β-d-galactoside (Sigma Chemical Co., St. Louis, Mo.) in 0.1 M NaCl—1 mM $MgCl_2$—0.1% BSA—0.1% $NaN_3$—0.01 M sodium phosphate (pH 7.0) is added. The wells are sealed with tape, and the plates are immersed in 37° C. water for 60 min. Finally, 0.1 ml of 0.1 M glycine-NaOH (pH 10.2) is added to each well to stop the enzyme reaction. The fluorescence units (FU) in each well is measured with a Fluoroskan II apparatus (Flow Laboratories, Rockville, Md.). The antibody concentrations of the test sera are calculated from the titration curve of the reference serum with known antibody units per milliliter.

In one preferred embodiment, the detection antibody is detectably labeled by linking the antibody to an enzyme. The enzyme, in turn, when exposed to its substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In other embodiments, the detection antibody is label with a fluorescent compound. When the fluorescently labeled antibody is exposed to light of the proper wavelength, its presence can then be detected due to fluorescence. Among the most commonly used fluorescent labeling compounds are CY dyes, fluorescein isothiocyanate, rhodamine, phycoerytherin, phycocyanin, allophycocyanin, o-phthaldehyde and fluorescamine.

A detection antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

A detection antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

There are other different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem. 22:895-904.

Other techniques can be used to detect PLA2R auto-antibodies in a sample. One such technique is Western blotting (Towbin et al., Proc. Nat. Acad. Sci. 76:4350 (1979)), another is an adaptation of the Western blot, the dot blots. In the Western blots, the PLA2R protein or fragments thereof can be dissociated with detergents and heat, and run on an SDS-PAGE gel before being transferred to a solid support, such as a nitrocellulose filter. The filter is washed with a sample suspected of containing auto-antibodies against PLA2R. The filter is then washed to remove unbound proteins and proteins with non-specific binding. Detectably labeled enzyme-linked secondary antibodies can then be used to detect and assess the amount of auto-antibodies in the sample tested. The intensity of the signal from the detectable label corresponds to the amount of enzyme present, and therefore the amount of auto-antibodies against PLA2R. Levels can be quantified, for example by densitometry.

Another immunological assay is nephelometric immunoassays. Nephelometric immunoassays are known to one skilled in the art and can be performed to the methods as described in U.S. Pat. Nos. 4,730,922, 4,268,171, 4,401,387, 4,408,880, 4,889,815, 4,690,906, 4,784,947, and 516,223, and all of which are hereby incorporated by reference in their entirety.

As positive control of antibodies against PLA2R, a known quantity of anti-PLA2R antibodies can be used. The anti-PLA2R antibodies can be obtained from commercial source such as INVITROGEN Inc., MILLIPORE, SIGMA-ALDRICH, R&D Systems, ABCAM and the World's Antibody Gateway (free search engine of over 150 antibody companies) and GeneTexto name a few. The antibodies can be polyclonal or monoclonal antibodies. Alternatively, antibodies can be raised against the human PLA2R protein (GENBANK™ Accession No. NP_001007268; SEQ. ID. NO. 1 and NP_031392.3, SEQ. ID. NO. 2) or fragments thereof by one of skill in the art. Methods for the production of antibodies are disclosed in PCT publication WO 97/40072 or U.S. Application. No. 2002/0182702, which are herein incorporated by reference. The processes of immunization to elicit antibody production in a mammal, the generation of hybridomas to produce monoclonal antibodies, and the purification of antibodies may be performed by described in "Current Protocols in Immunology" (CPI) (John Wiley and Sons, Inc.) and Antibodies: A Laboratory Manual (Ed Harlow and David Lane editors, Cold Spring Harbor Laboratory Press 1988) which are both incorporated by reference herein in their entireties.

The detection of auto-antibodies against PLA2R is considered positive when the immunoassay signal is at least 10% over that of the control immunoassay signal in the absence of an antibody against the PLA2R or fragments thereof or in the presence of a non-related, non-PLA2R binding antibody. In another embodiment, the control immunoassay signal is that obtained with the serum of non-MN healthy subject, these subjects do not have the clinical features of the disease. In another embodiment, the control immunoassay signal is the average value obtained for a population of non-MN healthy subjects. A population is at least 25 non-MN healthy subjects, preferably more. The increase is at least 5%, at least 10%, at least 20%, at least 30%, at least 50%, at least 100%, at least 200%, at least 300%, at least 500%, at least 1000%, or more and including all the percentages between 10-1000%.

In one embodiment, detection of auto-antibodies comprises identifying and detecting elevated amount of the mRNA that codes for the antibodies. There are many methods of detecting, identifying and determining mRNA that are well known in the art, e.g. Northern blots and RT-PCR. In one embodiment, the mRNA of can be determined by quantitative real-time PCR. Real time PCR is an amplification technique that can be used to determine levels of mRNA expression. (See, e.g., Gibson et al., Genome Research 6:995-1001, 1996; Heid et al., Genome Research 6:986-994, 1996). Real-time PCR evaluates the level of PCR product accumulation during amplification. This technique permits quantitative evaluation of mRNA levels in multiple samples. For mRNA levels, mRNA is extracted from a biological sample, e.g. a blood sample, and cDNA is prepared using standard techniques. Real-time PCR can be performed, for example, using a Perkin Elmer/Applied Biosystems (Foster City, Calif.) 7700 Prism instrument. Matching primers and fluorescent probes can be designed for genes of interest using, for example, the primer express program provided by Perkin Elmer/Applied Biosystems (Foster City, Calif.). Optimal concentrations of primers and probes can be initially determined by those of ordinary skill in the art, and control (for example, beta-actin) primers and probes can be obtained commercially from, for example, Perkin Elmer/Applied Biosystems (Foster City, Calif.). To quantify the amount of the specific nucleic acid of interest in a sample, a standard curve is generated using a control. Standard curves can be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes.

Methods of real-time quantitative PCR using TaqMan probes are well known in the art. Detailed protocols for real-time quantitative PCR are provided, for example, for RNA in: Gibson et al., 1996, Genome Res., 10:995-1001; and for DNA in: Heid et al., 1996, Genome Res., 10:986-994.

The TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification (see, for example, at the Perkin Elmer World Wide Web).

In another embodiment, the detection of RNA transcripts can be achieved by Northern blotting, wherein a preparation of RNA is run on a denaturing agarose gel, and transferred to a suitable support, such as activated cellulose, nitrocellulose or glass or nylon membranes. Labeled (e.g., radiolabeled) cDNA or RNA is then hybridized to the preparation, washed and analyzed by methods such as autoradiography.

In another embodiment, the detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap lipase chain reaction (RT-AGLCR) as described by R. L. Marshall, et al., PCR Methods and Applications 4: 80-84 (1994). One suitable method for detecting enzyme mRNA transcripts is described in reference Pabic et. al. Hepatology, 37(5): 1056-1066, 2003, which is herein incorporated by reference in its entirety.

In other embodiments, the detection of RNA transcripts can be achieved with other known amplification methods which include but are not limited to the so-called "NASBA" or "3SR" technique described in PNAS USA 87: 1874-1878 (1990) and also described in Nature 350: 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

Encompassed in the method described herein is employing in situ hybridization visualization for the detection of auto-antibodies to PLA2R RNA transcripts in blood samples. In in situ hybridization, a radioactively labeled antisense RNA probe is hybridized with a thin smear of platelets, after which the smear of platelets is washed, cleaved with RNase, and exposed to a sensitive emulsion for autoradiography. The samples can be stained with haematoxylin to demonstrate the histological composition of the sample, and dark field imaging with a suitable light filter shows the developed emulsion. Non-radioactive labels such as digoxigenin can also be used.

Alternatively, mRNA expression can be detected on a DNA array, chip or a microarray. Oligonucleotides corresponding to auto-antibodies to PLA2R RNA transcripts are immobilized on a chip which is then hybridized with labeled nucleic acids of a sample of platelets obtained from a patient. Positive hybridization signal is obtained with a sample containing auto-antibodies to PLA2R RNA transcripts. Methods of preparing DNA arrays and their use are well known in the art. (See, for example U.S. Pat. Nos. 6,618,6796; 6,379,897; 6,664,377; 6,451,536; 548,257; U.S. 20030157485 and Schena et al. 1995 Science 20:467-470; Gerhold et al. 1999 Trends in Biochem. Sci. 24, 168-173; and Lennon et al. 2000 Drug discovery Today 5: 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the blood sample to be tested, reverse transcribed, and fluorescent-labeled cDNA probes are generated. The microarrays capable of hybridizing to cDNA are then probed with the labeled cDNA probes, the slides scanned and fluorescence intensity measured. This intensity correlates with the hybridization intensity and expression levels. The cDNAs correspond to the auto-antibodies to PLA2R RNA transcripts, particularly in the variable region of the antibody.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided, for example, in Innis et al. (1990) PCR Protocols, A Guide to Methods and Applications, Academic Press, Inc. N.Y.

Recombinant PLA2R protein and PLA2R Expression Vectors

Recombinant PLA2R protein and fragments thereof can also be synthesized and purified by molecular methods that are well known in the art. For example, recombinant proteins can be expressed in bacteria, mammal, insect, yeast, or plant cells.

Conventional polymerase chain reaction (PCR) cloning techniques can be used to clone a nucleic acid encoding a PLA2R, using the mRNA of the PLA2R as the template for PCR Cloning. In some embodiments, the mRNA templates of the human PLA2R are Genbank Accession Nos. NM_001007267, SEQ. ID. NO. 3 and NM_007366.3, SEQ. ID. NO. 4. Ideally, restriction enzyme digestion recognition sites should be designed at the ends of the sense and anti-sense strand of the PCR primers to facilitate ligation of the amplified nucleic acid into a cloning vector or other vectors. Alternatively, a 3'-A overhang can be include for the purpose of TA-cloning that is well known in the art. Such coding nucleic acids with 3'A overhangs can be easily ligated into the Invitrogen topoisomerase-assisted TA vectors such as pCR®-TOPO, pCR®-Blunt II-TOPO, pENTR/D-TOPO®, and pENTR/SD/D-TOPO®. The coding nucleic acid can be cloned into a general purpose cloning vector such as pUC19, pBR322, pBLUESCRIPT vectors (STRATAGENE Inc.) or pCR TOPO® from Invitrogen Inc. The resultant recombinant vector carrying the nucleic acid encoding a PLA2R can then subcloned into protein expression vectors or viral vectors for the synthesis of PLA2R fusion protein in a variety of protein expression systems using host cells selected from the group consisting of mammalian cell lines, insect cell lines, yeast, bacteria, and plant cells. Protease cleavage sites can also be designed and included within the nucleic acid to facilitate the liberation of PLA2R from a larger fusion protein, e.g. His-PLA2R or thioredoxin-PLA2R. Examples of protease cleavage sites include but are not limited to those of enterokinase, chymotrypsin, and thrombin.

PCR amplified coding nucleic acids can be cloned into a vector using the TOPO® cloning method in Invitrogen topoisomerase-assisted TA vectors such as pCR®-TOPO, pCR® Blunt II-TOPO, pENTR/D-TOPO®, and pENTR/SD/D-TOPO®. Both pENTR/D-TOPO®, and pENTR/SD/D-TOPO® are directional TOPO entry vectors which allow the cloning of the DNA sequence in the 5'→3' orientation into a GATEWAY® expression vector. Directional cloning in the 5'→3' orientation facilitate the unidirectional insertion of the DNA sequence into a protein expression vector such that the promoter is upstream of the 5' ATG start codon of the nucleic acid, thus enabling promoter-driven protein expression. The recombinant vector carrying a PLA2R coding nucleic acid can be transfected into and propagated in a general cloning *E. coli* cells such as XL1Blue, SURE (STRATAGENE) and TOP-10 cells (INVITROGEN).

Different expression vectors are available for the expression and purification of a recombinant protein produced from a heterologous protein expression system can be made. Heterologous protein expression systems that use host cells selected from, e.g., mammalian, insect, yeast, bacterial, or plant cells are well known to one skilled in the art. The expression vector should have the necessary 5' upstream and 3' downstream regulatory elements such as promoter sequences, ribosome recognition and binding TATA box, and 3' UTR AAUAAA (SEQ. ID. NO. 6) transcription termination sequence for efficient gene transcription and translation in its respective host cell. The expression vector may have additional sequence such as 6X-histidine (SEQ. ID. NO. 7), V5, thioredoxin, glutathione-S-transferase, c-Myc, VSV-G, HSV, FLAG, maltose binding peptide, metal-binding peptide, HA and "secretion" signals (Honeybee melittin, α-factor, PHO, Bip), which are incorporated into the expressed recombinant protein. In addition, there can be enzyme digestion sites incorporated after these sequences to facilitate enzymatic removal of additional sequence after they are not needed. These additional sequences are useful for the detection of recombinant protein expression, for protein purification by affinity chromatography, enhanced solubility of the recombinant protein in the host cytoplasm, for better protein expression especially for small protein fragments and/or for secreting the expressed recombinant protein out into the culture media, into the periplasm of the prokaryote bacteria, or to the spheroplast of yeast cells. The expression of recombinant protein can be constitutive in the host cells or it can be induced, e.g., with copper sulfate, sugars such as galactose, methanol, methylamine, thiamine, tetracycline, infection with baculovirus, and (isopropyl-beta-D-thiogalactopyranoside) IPTG, a stable synthetic analog of lactose.

In some embodiments, recombinant PLA2R can be expressed in a variety of expression host cells e.g., bacteria, such as *E. coli*, yeast, mammalian, insect, and plant cells such as *Chlamydomonas*, or even from cell-free expression systems. From a cloning vector, the nucleic acid can be subcloned into a recombinant expression vector that is appropriate for the expression of the protein in mammalian, insect, yeast, bacterial, or plant cells or a cell-free expression system such as a rabbit reticulocyte expression system. Subcloning can be achieved by PCR cloning, restriction digestion followed by ligation, or recombination reaction such as those of the lambda phage-based site-specific recombination using the Gateway® LR and BP CLONASE™ enzyme mixtures. Subcloning should be unidirectional such that the 5' ATG start codon of the nucleic acid is downstream of the promoter in the expression vector. Alternatively, when the coding nucleic acid is cloned into pENTR/D-TOPO®, pENTR/SD/D-TOPO® (directional entry vectors), or any of the Invitrogen's Gateway® Technology pENTR (entry) vectors, the coding nucleic acid can be transferred into the various GATEWAY® expression vectors (destination) for protein expression in mammalian cells, *E. coli*, insects and yeast respectively in one single recombination reaction. Some of the GATEWAY® destination vectors are designed for the constructions of baculovirus, adenovirus, adeno-associated virus (AAV), retrovirus, and lentiviruses, which upon infecting their respective host cell, permit heterologous expression of the recombinant protein in the host cells. Transferring a gene into a destination vector is accomplished in just two steps according to manufacturer's instructions. There are GATEWAY® expression vectors for protein expression in *E. coli*, insect cells, mammalian cells, and yeast. Following transformation and selection in *E. coli*, the expression vector is ready to be used for expression in the appropriate host.

Examples of other expression vectors and host cells are the pET vectors (NOVAGEN), pGEX vectors (Amersham Pharmacia), and pMAL vectors (New England labs. Inc.) for protein expression in *E. coli* host cells such as BL21, BL21 (DE3) and AD494(DE3)pLysS, Rosetta (DE3), and Origami (DE3) (NOVAGEN); the strong CMV promoter-based pcDNA3.1 (INVITROGEN) and pCIneo vectors (Promega) for expression in mammalian cell lines such as CHO, COS, HEK-293, Jurkat, and MCF-7; replication incompetent adenoviral vector vectors pADENO X, pAd5F35, pLP-ADENO-X-CMV (CLONTECH), pAd/CMV/V5-DEST, pAd-DEST vector (INVITROGEN) for adenovirus-mediated gene transfer and expression in mammalian cells; pLNCX2, pLXSN, and pLAPSN retrovirus vectors for use with the RETRO-X™ system from Clontech for retroviral-mediated gene transfer and expression in mammalian cells; pLenti4/V5-DEST™, pLenti6/V5-DEST™, and pLenti6.2/V5-GW/lacZ (INVITROGEN) for lentivirus-mediated gene transfer and expression in mammalian cells; adenovirus-associated virus expression vectors such as pAAV-MCS, pAAV-IRES-hrGFP, and pAAV-RC vector (Stratagene) for adeno-associated virus-mediated gene transfer and expression in mammalian cells; BACpak6 baculovirus (CLONTECH) and pFASTBAC™ HT (INVITROGEN) for the expression in *Spodopera frugiperda* 9 (Sf9) and Sf11 insect cell lines; pMT/BiP/V5-His (INVITROGEN) for the expression in *Drosophila Schneider* S2 cells; *Pichia* expression vectors pPICZα, pPICZ, pFLDα and pFLD (Invitrogen) for expression in *Pichia pastoris* and vectors pMETα and pMET for expression in *P. methanolica*; pYES2/GS and pYD1 (INVITROGEN) vectors for expression in yeast *Saccharomyces cerevisiae*. Recent advances in the large scale expression heterologous proteins in *Chlamydomonas reinhardtii* are described by Griesbeck C. et. al. 2006 Mol. Biotechnol. 34:213-33 and Fuhrmann M. 2004, Methods Mol. Med. 94:191-5. Foreign heterologous coding sequences are inserted into the genome of the nucleus, chloroplast and mitochodria by homologous recombination. The chloroplast expression vector p64 carrying the versatile chloroplast selectable marker aminoglycoside adenyl transferase (aadA), which confers resistance to spectinomycin or streptomycin, can be used to express foreign protein in the chloroplast. The biolistic gene gun method can be used to introduce the vector in the algae. Upon its entry into chloroplasts, the foreign DNA is released from the gene gun particles and integrates into the chloroplast genome through homologous recombination.

Recombinant protein expression in the different host cells can be constitutive or inducible with inducers such as copper sulfate, sugars such as galactose, methanol, methylamine, thiamine, tetracycline, or IPTG. After the protein is expressed in the host cells, the host cells are lysed to liberate the expressed protein for purification. Methods of lysing the various host cells are featured in "Sample Preparation-Tools for Protein Research" EMD Bioscience and in the Current Protocols in Protein Sciences (CPPS). A preferred purification method is affinity chromatography such as ion-metal affinity chromatograph using nickel, cobalt, or zinc affinity resins for histidine-tagged recombinant protein. Methods of purifying histidine-tagged recombinant proteins are described by CLONTECH using their TALON® cobalt resin and by NOVAGEN in their pET system manual, 10th edition. Another preferred purification strategy is by immuno-affinity chromatography, for example, anti-myc antibody conjugated resin can be used to the affinity purify myc-tagged recombinant peptide. Enzymatic digestion with serine proteases such as thrombin and enterokinase cleave and release the recombinant protein from the histidine or myc tag, releasing the recombinant protein from the affinity resin while the histidine-tags and myc-tags are left attached to the affinity resin.

Cell-free expression systems are also contemplated. Cell-free expression systems offer several advantages over traditional cell-based expression methods, including the easy modification of reaction conditions to favor protein folding, decreased sensitivity to product toxicity and suitability for high-throughput strategies such as rapid expression screening or large amount protein production because of reduced reaction volumes and process time. The cell-free expression system can use plasmid or linear DNA. Moreover, improvements in translation efficiency have resulted in yields that exceed a milligram of protein per milliliter of reaction mix. An example of a cell-free translation system capable of producing proteins in high yield is described by Spirin A S. et. al., Science 242:1162 (1988). The method uses a continuous flow design of the feeding buffer which contains amino acids, adenosine triphosphate (ATP), and guanosine triphosphate (GTP) throughout the reaction mixture and a continuous removal of the translated polypeptide product. The system uses *E. coli* lysate to provide the cell-free continuous feeding buffer. This continuous flow system is compatible with both prokaryotic and eukaryotic expression vectors. As an example, large scale cell-free production of the integral membrane protein EmrE multidrug transporter is described by Chang G. el. al., Science 310:1950-3 (2005).

Other commercially available cell-free expression systems include the EXPRESSWAY™ Cell-Free Expression Systems (Invitrogen) which utilize an *E. coli*-based in-vitro system for efficient, coupled transcription and translation reactions to produce up to milligram quantities of active recombinant protein in a tube reaction format; the Rapid Translation System (RTS) (Roche Applied Science) which also uses an *E. coli*-based in-vitro system; and the TNT Coupled Reticulocyte Lysate Systems (Promega) which uses a rabbit reticulocyte-based in-vitro system.

Encompassed in the methods described herein is a mammalian PLA2R that is purified from a mammal, e.g. a pig or a rabbit. In one embodiment, the native (non-recombinant) mammalian PLA2R is purified from the kidneys ex vivo. Methods of native protein purification are well known to one skilled in the art.

Therapeutic/Prophylactic Compositions and Administration

In one embodiment, the invention provides a pharmaceutical composition comprising a PLA2R or fragment thereof and a pharmaceutically acceptable vehicle. The pharmaceutical composition can be a combination of full-length PLA2R and fragments of various sizes, and a pharmaceutically acceptable vehicle. Examples of fragments are fragments comprising the CTLDs or CRDs 4, 5 6 of PLA2R or other fragments of the extracellular domain of PLA2R. The pharmaceutical composition is used for the treatment of MN that is characterized by the presence of auto-antibodies against PLA2R.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). In one embodiment, other ingredients can be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lignocamne to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, to name a few.

Various delivery systems are known in the art and can be used to administer a PLA2R protein or fragments thereof, e.g., encapsulation in liposomes, microparticles, and microcapsules (see, e.g., Wu and Wu, J. Biol. Chem., 262:4429-4432 (1987)). The composition can be delivered in a vesicle, in particular a liposome (see, Langer, Science, 249:1527-1533 (1990); Treat et al., in Liposomes in the Therapy of Infectious Disease and Cancer, Lopez-Berestein and Fidler, eds. (Liss, New York 1989), pp. 353-365; Lopez-Berestein, ibid., pp. 317-327; see, generally, ibid.). Methods of introduction include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (e.g., oral mucosa, rectal and intestinal mucosa, etc.) and can be administered together with other biologically active agents. Administration can be systemic or local. In addition, it can be desirable to introduce the pharmaceutical compositions of the invention into the central nervous system by any suitable route, including intraventricular and intrathecal injection; intraventricular injection can be facilitated by an intraventricular catheter, for example, attached to a reservoir, such as an Omcana reservoir. Pulmonary administration can also be employed, e.g., by use of an inhaler or nebulizer, and formulation with an aerosolizing agent.

In one embodiment, the pharmaceutical formulation to be used for therapeutic administration must be sterile. Sterility is readily accomplished by filtration through sterile filtration membranes (e.g., 0.2 micron membranes). The pH of the pharmaceutical formulation typically should be about from 6 to 8.

In one embodiment, the composition can be delivered in a controlled release system. In one embodiment, a pump can be used (see Langer, supra; Sefton, CRC Crit. Ref. Biomed. Eng., 14:201 (1987); Buchwald et al., Surgery, 88:507 (1980); Saudek et al., N. Engl. J. Med., 321:574 (1989)). In another embodiment, polymeric materials can be used (see, Medical Applications of Controlled Release, Langer and Wise, eds. (CRC Press, Boca Raton, Fla. 1974); Controlled Drug Bioavailability, Drug Product Design and Performance, Smolen and Ball, eds. (Wiley, New York 1984); Ranger and Peppas, Macromol. Sci. Rev. Macromol. Chem., 23:61 (1983); see also Levy et al., Science, 228:190 (1985); During et al., Ann. Neurol., 25:35 1 (1989); Howard et al., J. Neurosurg., 7 1:105 (1989)). Other controlled release systems are discussed in the review by Langer (Science, 249:1527-1533 (1990)). For examples of sustained release compositions, see U.S. Pat. No. 3,773,919, EP 58,481A, U.S. Pat. No. 3,887, 699, EP 158,277A, Canadian Patent No. 1176565, U. Sidman et al., Biopolymers 22:547 (1983) and R. Langer et al., Chem. Tech. 12:98 (1982).

The precise dose to be employed in the formulation will also depend on the route of administration, and the severity of MN and the titer of auto-antibodies against PLA2R in the serum, and should be decided according to the judgment of the practitioner and each patient's circumstances. Effective doses can be extrapolated from dose-response curves derived from in vitro or animal model test systems.

The dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. For gene therapy, viral vector should be in the range of $1\times10^6$ to $10^{14}$ viral vector particles per application per patient.

In addition, in vitro or in vivo assays can optionally be employed to help identify optimal dosage ranges. The precise dose to be employed will also depend on the route of administration, and the seriousness of the condition being treated and should be decided according to the judgment of the practitioner and each subject's circumstances in view of, e.g., published clinical studies. Suitable effective dosage amounts, however, range from about 10 micrograms to about 5 grams about every 4 hour, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, or about 5.0 g, every 4 hours. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The effective dosage amounts described herein refer to total amounts administered. The compositions comprising PLA2R protein, fragments thereof, or expression vectors and/or viral vectors are suitably administered to the patient at one time or over a series of treatments. For purposes herein, a "therapeutically effective amount" of a composition comprising PLA2R protein, fragments thereof, or expression vectors and/or viral vectors is an amount that is effective to reduce the amount of auto-antibodies against PLA2R in a sample from a subject. The amount reduction is at least 10% reduction in the auto-antibodies compared to the amount of auto-antibodies present in the serum prior to the start of a treatment.

In an embodiment, the composition comprising a PLA2R or fragments thereof is administered in combination with immunosuppressive therapies including, but not limited to, azathioprine, infliximab, omalizumab, daclizumab, adalimumab, eculizumab, efalizumab, natalizumab, and omalizumab. In another embodiment, the composition comprising a PLA2R or fragments thereof is administered in combination with immunosuppressive therapies and cyclophosphamide, chlorambucil, and/or rituximab.

Gene Therapy

In one embodiment, the PLA2R protein or fragments thereof is administered to an individual by any one of several gene therapy techniques known to those of skill in the art. In general, gene therapy can be accomplished by either direct transformation of target cells within the mammalian subject (in vivo gene therapy) or transformation of cells in vitro and subsequent implantation of the transformed cells into the mammalian subject (ex vivo gene therapy). A viral vector carries a nucleic acid encoding PLA2R protein or fragments thereof under a tissue specific regulatory element is administered to an individual. The tissue specific regulatory element allows the expression of the PLA2R protein or fragments thereof in the target cells, for example, the muscles.

The principles of gene therapy are disclosed by Oldham, R. K. (In: Principles of Biotherapy, Raven Press, N.Y., 1987), and similar texts. Disclosures of the methods and uses for gene therapy are provided by Boggs, S. S. (Int. J. Cell Clon. 8:80-96 (1990)); Karson, E. M. (Biol. Reprod. 42:39-49 (1990)); Ledley, F. D., In: Biotechnology, A Comprehensive Treatise, volume 7B, Gene Technology, VCH Publishers, Inc. NY, pp 399-458 (1989)), all of which references are incorporated herein by reference.

The nucleic acid encoding PLA2R protein or fragments thereof can be introduced into the somatic cells of an animal (particularly mammals including humans) in gene therapy. Most preferably, viral or retroviral vectors are employed for as the transfer vehicle this purpose. The gene therapy virus can be in the form of an adenovirus, adeno-associated virus or lentivirus.

Retroviral vectors are a common mode of delivery and in this context are retroviruses from which all viral genes have been removed or altered so that no viral proteins are made in cells infected with the vector. Viral replication functions are provided by the use of retrovirus "packaging" cells that produce all of the viral proteins but that do not produce infectious virus.

Introduction of the retroviral vector DNA into packaging cells results in production of virions that carry vector RNA and can infect target cells, but such that no further virus spread occurs after infection. To distinguish this process from a natural virus infection where the virus continues to replicate and spread, the term transduction rather than infection is often used.

In one embodiment, the method of treating MN described herein provides a recombinant lentivirus for the delivery and expression of a PLA2R protein or fragments thereof in either dividing and non-dividing mammalian cells. The HIV-1 based lentivirus can effectively transduce a broader host range than the Moloney Leukemia Virus (MoMLV)-base retroviral systems. Preparation of the recombinant lentivirus can be achieved using the pLenti4/V5-DEST™, pLenti6/V5-DEST™ or pLenti vectors together with ViraPower™ Lentiviral Expression systems from Invitrogen.

Examples of use of lentiviral vectors for gene therapy for inherited disorders and various types of cancer, and these references are hereby incorporated by reference (Klein, C. and Baum, C. (2004). Hematol. J., 5, 103-111; Zufferey, R et. al. (1997). Nat. Biotechnol., 15, 871-875; Morizono, K. et. al. (2005). Nat. Med., 11, 346-352; Di Domenico, C. et. al. (2005), Hum. Gene Ther., 16, 81-90; Kim, E. Y., et. al., (2004). Biochem. Biophys. Res. Comm., 318, 381-390).

Non-retroviral vectors also have been used in genetic therapy. One such alternative is the adenovirus (Rosenfeld, M. A., et al., Cell 68:143155 (1992); Jaffe, H. A. et al., Nature Genetics 1:372-378 (1992); Lemarchand, P. et al., Proc. Natl. Acad. Sci. USA 89:6482-6486 (1992)). Major advantages of adenovirus vectors are their potential to carry large segments of DNA (36 Kb genome), a very high titre ($10^{11}$/ml), ability to infect non-replicating cells, and suitability for infecting tissues in situ, especially in the lung. The most striking use of this vector so far is to deliver a human cystic fibrosis transmembrane conductance regulator (CFTR) gene by intratracheal instillation to airway epithelium in cotton rats (Rosenfeld, M. A., et al., Cell 63:143-155 (1992)). Similarly, herpes viruses may also prove valuable for human gene therapy (Wolfe, J. H. et al., Nature Genetics 1:379-384 (1992)). Of course, any other suitable viral vector may be used for genetic therapy with the present invention.

U.S. Pat. No. 6,531,456 provides methods for the successful transfer of a gene into a solid tumor cell using recombinant AAV virions. Generally, the method described in U.S. Pat. No. 6,531,456 allows for the direct, in vivo injection of recombinant AAV virions into tumor cell masses, e.g., by intra-tumoral injection. The invention also provides for the simultaneous delivery of a second gene using the recombinant AAV virions, wherein the second gene is capable of providing an ancillary therapeutic effect when expressed within the transduced cell. U.S. Pat. No. 6,531,456 is hereby incorporated by reference in its entirety.

The viron used for gene therapy can be any viron known in the art including but not limited to those derived from adenovirus, adeno-associated virus (AAV), retrovirus, and lentivirus. Recombinant viruses provide a versatile system for gene expression studies and therapeutic applications.

The recombinant AAV virions described above, including the DNA of interest, can be produced using standard methodology, known to those of skill in the art. The methods generally involve the steps of (1) introducing an AAV vector into a host cell; (2) introducing an AAV helper construct into the host cell, where the helper construct includes AAV coding regions capable of being expressed in the host cell to complement AAV helper functions missing from the AAV vector; (3) introducing one or more helper viruses and/or accessory function vectors into the host cell, wherein the helper virus and/or accessory function vectors provide accessory functions capable of supporting efficient recombinant AAV ("rAAV") virion production in the host cell; and (4) culturing the host cell to produce rAAV virions. The AAV vector, AAV helper construct and the helper virus or accessory function vector(s) can be introduced into the host cell either simultaneously or serially, using standard transfection techniques. Using rAAV vectors, genes can be delivered into a wide range of host cells including many different human and non-human cell lines or tissues. Because AAV is non-pathogenic and does not illicit an immune response, a multitude of pre-clinical studies have reported excellent safety profiles. rAAVs are capable of transducing a broad range of cell types and transduction is not dependent on active host cell division. High titers, >$10^8$ viral particle/ml, are easily obtained in the supernatant and $10^{11}$-$10^{12}$ viralparticle/ml with further concentration. The transgene is integrated into the host genome so expression is long term and stable.

A simplified system for generating recombinant adenoviruses is presented by He T C. et. al. Proc. Natl. Acad. Sci. USA 95:2509-2514, 1998. The gene of interest is first cloned into a shuttle vector, e.g. pAdTrack-CMV. The resultant plasmid is linearized by digesting with restriction endonuclease Pme I, and subsequently cotransformed into E. coli. BJ5183 cells with an adenoviral backbone plasmid, e.g. pAdEasy-1 of Stratagene's AdEasy™ Adenoviral Vector System. Recombinant adenovirus vectors are selected for kanamycin resistance, and recombination confirmed by restriction endonuclease analyses. Finally, the linearized recombinant plasmid is transfected into adenovirus packaging cell lines, for example HEK 293 cells (E1-transformed human embryonic kidney cells) or 911 (E1-transformed human embryonic retinal cells) (Human Gene Therapy 7:215-222, 1996). Recombinant adenovirus are generated within the HEK 293 cells.

The use of alternative AAV serotypes other than AAV-2 (Davidson et al (2000), Proc. Natl. Acad. Sci. USA 97(7) 3428-32; Passini et al (2003), J. Virol. 77(12):7034-40) has demonstrated different cell tropisms and increased transduction capabilities. With respect to brain cancers, the development of novel injection techniques into the brain, specifically convection enhanced delivery (CED; Bobo et al (1994), Proc. Natl. Acad. Sci. USA 91(6):2076-80; Nguyen et al (2001), Neuroreport 12(9):1961-4), has significantly enhanced the ability to transduce large areas of the brain with an AAV vector.

Large scale preparation of AAV vectors is made by a three-plasmid cotransfection of a packaging cell line: AAV vector carrying a DNA coding sequence for an antisense oligonucleotide to hnRNPLL or an siRNA hnRNPLL nucleic acid molecule, AAV RC vector containing AAV rep and cap genes, and adenovirus helper plasmid pDF6, into 50×150 mm plates of subconfluent 293 cells. Cells are harvested three days after transfection, and viruses are released by three freeze-thaw cycles or by sonication.

AAV vectors are then purified by two different methods depending on the serotype of the vector. AAV2 vector is purified by the single-step gravity-flow column purification method based on its affinity for heparin (Auricchio, A., et. al., 2001, Human Gene therapy 12; 71-6; Summerford, C. and R. Samulski, 1998, J. Virol. 72:1438-45; Summerford, C. and R.

Samulski, 1999, Nat. Med. 5: 587-88). AAV2/1 and AAV2/5 vectors are currently purified by three sequential CsCl gradients.

Pharmaceutical compositions used in the methods described herein can be delivered systemically via in vivo gene therapy. A variety of methods have been developed to accomplish in vivo transformation including mechanical means (e.g, direct injection of nucleic acid into target cells or particle bombardment), recombinant viruses, liposomes, and receptor-mediated endocytosis (RME) (for reviews, see Chang et al. 1994 Gastroenterol. 106:1076-84; Morsy et al. 1993 JAMA 270:2338-45; and Ledley 1992 J. Pediatr. Gastroenterol. Nutr. 14:328-37).

Another gene transfer method for use in humans is the transfer of plasmid DNA in liposomes directly to human cells in situ (Nabel, E. G., et al., Science 249:1285-1288 (1990)). Plasmid DNA should be easy to certify for use in human gene therapy because, unlike retroviral vectors, it can be purified to homogeneity. In addition to liposome-mediated DNA transfer, several other physical DNA transfer methods, such as those targeting the DNA to receptors on cells by conjugating the plasmid DNA to proteins, have shown promise in human gene therapy (Wu, G. Y., et al., J. Biol. Chem. 266:14338-14342 (1991); Curiel, D. T., et al., Proc. Natl. Acad. Sci. USA, 88:8850-8854 (1991)).

For gene therapy viruses, the dosage ranges from $10^6$ to $10^{14}$ particles per application. Alternatively the biolistic gene gun method of delivery may be used. The gene gun is a device for injecting cells with genetic information, originally designed for plant transformation. The payload is an elemental particle of a heavy metal coated with plasmid DNA. This technique is often simply referred to as biolistics. Another instrument that uses biolistics technology is the PDS-1000/He particle delivery system. The proteins, expression vector, and/or gene therapy virus can be coated on minute gold particles, and these coated particles are "shot" into biological tissues such as hemangiomas and melanoma under high pressure. An example of the gene gun-based method is described for DNA based vaccination of cattle by Loehr B. I. et. al. J. Virol. 2000, 74:6077-86.

The present invention may be defined by any of the following alphabetized paragraphs:

[A] A method of diagnosing membranous nephropathy (MN) in a subject, the method comprising detecting the presence of antibodies that are reactive to a phospholipase A2 receptor (PLA2R), wherein the antibodies are found in a sample from a subject.

[B] The method of paragraph [A], wherein the MN is idiopathic.

[C] The method of paragraph [A], wherein the subject is a human.

[D] The method of any of paragraphs [A]-[C], wherein a kidney biopsy is not performed.

[E] The method of paragraph [A], wherein the PLA2R is a mammalian PLA2R.

[F] The method of paragraph [A], wherein the sample is a blood sample.

[G] The method of paragraph [A], wherein the antibodies are of the IgG subclass: IgG1-4.

[H] The method of any of paragraphs [A]-[G], wherein the detecting is performed by a serological immunoassay.

[I] A method of prognosis evaluation in a subject being treated for MN, the method comprising:
  a. determining at a first time point a level of antibodies that are reactive to a PLA2R, wherein the antibodies are found in a sample from a subject;
  b. determining at a second time point a level of antibodies that are reactive to a PLA2R, wherein the second time point is after the first time point; and
  c. comparing the levels of antibodies of the two time points, wherein a decrease in the level of antibodies in the second time point compared to the first time point indicates that the treatment is effective.

[J] A method of prognosis evaluation in a subject for MN, the method comprising:
  a. determining at a first time point a level of antibodies that are reactive to a PLA2R, wherein the antibodies are found in a sample from a subject; and
  b. determining at a second time point a level of antibodies that is reactive to a PLA2R, wherein the second time point are after the first time point;
  wherein when the level of antibodies in the second time point decreases to below a detection limit indicates that there is remission.

[K] A method of prognosis evaluation in a subject for MN, the method comprising:
  a. determining at a first time point a level of antibodies that are reactive to a PLA2R, wherein the antibodies are found in a sample from a subject;
  b. determining at a second time point a level of antibodies that are reactive to a PLA2R, wherein the second time point is after the first time point;
  c. comparing the levels of antibodies of the two time points, wherein an increase in the level of antibodies in the second time point compared to the first time point indicates that there is relapse of membranous nephropathy.

[L] The method of paragraphs [I], [J] or [K], wherein the MN is idiopathic.

[M] The method of paragraphs [I], [J] or [K], wherein the subject is a human.

[N] The method of paragraphs [I], [J] or [K], wherein a kidney biopsy is not performed.

[O] The method of paragraph [I], [J] or [K], wherein the PLA2R is a mammalian PLA2R.

[P] The method of paragraph [I], [J] or [K], wherein the sample is a blood sample.

[Q] The method of paragraph [I], [J] or [K], wherein the antibodies are of the IgG subclass: IgG1-4.

[R] The method of any of paragraphs [L]-[Q], wherein the detecting is performed by a serological immunoassay.

[S] The method of paragraph [I], wherein the treatment is an immunosuppressive treatment.

[T] A method of treatment of MN in a subject, the method comprising removing an antibody that is reactive to a PLA2R from a sample in a subject ex vivo.

[U] The method of paragraph [T], wherein the subject is a human.

[V] The method of paragraph [T], wherein the MN is idiopathic.

[W] The method of paragraph [T], wherein the phospholipase A2 receptor is a mammalian PLA2R.

[X] The method of paragraph [T], wherein the sample is a blood sample.

[Y] The method of paragraph [T], wherein the antibodies are of the IgG subclass: IgG1-4.

[Z] The method of paragraph [T], wherein the antibodies are removed from the blood by immunoabsorption.

[AA] The method of paragraph [T], wherein the sample is returned back into the subject after the removal of the antibodies.

[BB] A method of treatment of MN in a subject, the method comprising administering an effective amount of PLA2R or fragments thereof or a vector expressing a PLA2R or fragments thereof.

[CC] The method of paragraph [BB], wherein the MN is idiopathic.

[DD] The method of paragraph [BB], wherein the subject has tested positive for antibodies reactive against a PLA2R.

[EE] The method of paragraph [BB], wherein the phospholipase A2 receptor is a mammalian PLA2R.

[FF] A composition for the treatment of idiopathic MN, the composition comprising a PLA2R or fragments thereof.

[GG] A use of an effective amount of PLA2R or fragments thereof or a vector expressing a PLA2R or fragments thereof for the treatment of MN in a subject.

[HH] A use of an effective amount of PLA2R or fragments thereof or a vector expressing a PLA2R or fragments thereof in the manufacture of a medicament for treatment of MN in a subject.

[II] The use of paragraph [GG] or [HH], wherein the MN is idiopathic.

[JJ] The use of paragraph [GG] or [HH], wherein the subject has tested positive for antibodies reactive against a PLA2R

[KK] The use of paragraph [GG] or [HH], wherein the phospholipase A2 receptor is a mammalian PLA2R.

[LL] An immunoassay comprising:
  a. contacting a sample from a subject with a PLA2R or PLA2R fragment thereof;
  b. forming an antibody-protein complex between the antibody present in a sample with the PLA2R or PLA2R fragment thereof;
  c. washing to remove any unbound antibody;
  d. adding a detection antibody that is labeled and is reactive to the antibody from the sample;
  e. washing to remove any unbound labeled detection antibody; and
  f. converting the label to a detectable signal, wherein the presence of a detectable signal indicates the likelihood of MN in the subject.

[MM] The immunoassay of paragraph [LL], wherein the MN is idiopathic.

[NN] The immunoassay of paragraph [LL] or [MM], wherein, the subject is a human.

[OO] The immunoassay of paragraph [LL], [MM] or [NN], wherein the sample is a blood sample.

[PP] The immunoassay of any of paragraph [LL]-[OO], wherein a kidney biopsy is not performed in the subject.

[QQ] The immunoassay of any of paragraph [LL]-[PP], wherein the PLA2R is a mammalian PLA2R.

[RR] The immunoassay of any of paragraph [LL]-[QQ], wherein the antibodies are of the IgG subclass: IgG1-4.

[SS] The immunoassay of any of paragraph [LL]-[RR], wherein the PLA2R or PLA2R protein fragment thereof is deposited or immobilized on a solid support.

[TT] The immunoassay of any of paragraph [LL]-[SS], wherein a known amount of a PLA2R or PLA2R protein fragment is deposited or coupled to a solid support.

[UU] The immunoassay of paragraph [SS] or [TT], wherein the support is in the format of a dipstick, a test strip, a latex bead, a microsphere or a multi-well plate.

[VV] The immunoassay of any of paragraph [LL]-[UU], wherein the detection antibody is labeled by covalently linking to an enzyme, label with a fluorescent compound or metal, or label with a chemiluminescent compound.

[WW] The immunoassay of any of paragraph [LL]-[VV], wherein the detection antibody is specifically reactive to the subject.

[XX] The immunoassay of any of paragraph [LL]-[WW], wherein the detectable signal is compared to a set of detectable signals from a titration curve derived from immunoassays of known amounts of PLA2R or fragments in increasing quantity.

[YY] The immunoassay of any of paragraph [LL]-[XX], wherein the immunoassay is performed for a plurality of samples from a subject obtained over a period of time.

[ZZ] The immunoassay of paragraph [YY], wherein the plurality of samples is obtained every two or three months for at least a two year period.

[AAA] The immunoassay of paragraph [ZZ], wherein the detectable signal of each immunoassay is compared to the detectable signal of a sample obtained from a consecutively prior time point, wherein a reduction of 10% of detectable signal indicates effective treatment of MN in the subject.

[BBB] An immunoassay comprising:
  a. contacting a sample from a subject with a PLA2R or PLA2R fragment thereof;
  b. forming an antibody-protein complex between the antibody present in a sample with the PLA2R or PLA2R fragment thereof;
  c. measuring a light scattering intensity resulting from the formation of the antibody-protein complex wherein the light scattering intensity of at least 10% above a control light scattering intensity indicates the likelihood of MN or relapse of MN in the subject.

[CCC] The immunoassay of paragraph [BBB], wherein the PLA2R or PLA2R protein fragment thereof is immobilized on a solid support.

[DDD] The immunoassay of paragraph [CCC], wherein the solid support is a latex bead or a microsphere.

[EEE] The immunoassay of any of paragraph [BBB]-[DDD], wherein the control light scattering intensity is that of PLA2R or PLA2R protein fragment in the absence of sample.

[FFF] The immunoassay of any of paragraph [BBB]-[EEE], wherein light scattering intensity is measured in a nephelometer.

[GGG] The immunoassay of any of paragraph [BBB]-[FFF], wherein the immunoassay is performed for a plurality of samples from a subject obtained over a period of time.

[HHH] The immunoassay of paragraph [GGG], wherein the plurality of samples are obtained every two or three months for at least a two year period.

[III] The immunoassay of paragraph [HHH], wherein the light scattering intensity of each immunoassay is compared to the light scattering intensity of a sample obtained from a consecutively prior time point, wherein a reduction of 10% of light scattering intensity indicates effective treatment of MN in the subject.

[JJJ] A device for identifying the presence or the level of antibodies that are reactive to a PLA2R in a sample from a subject comprising:
  a. at least a PLA2R protein or fragments thereof; and
  b. at least one solid support wherein the PLA2R protein or fragments thereof is deposited on the support.

[KKK] The device of paragraph [JJJ], wherein at least a PLA2R protein or fragments thereof that is deposited on the solid support is immobilized on the support.

[LLL] The device of paragraph [JJJ], wherein the solid support is in the format of a dipstick, a test strip, a latex bead, a microsphere or a multi-well plate.

[MMM] The device of paragraph [JJJ], wherein the subject is a human.

[NNN] The device of paragraph [JJJ], wherein a kidney biopsy is not performed in the subject.

[OOO] The device of paragraph [JJJ], wherein the sample from the subject is a blood sample.

[PPP] The device of paragraph [JJJ], wherein the PLA2R protein is a human or pig PLA2R protein.

[QQQ] The device of paragraph [JJJ] further comprising a second labeled PLA2R protein or fragments thereof which produces a detectable signal.

[RRR] The device of paragraph [JJJ] further comprising a detection antibody, wherein the detection antibody is specific for the antibodies that are reactive to a PLA2R in the sample of the subject and the detection antibody produces a detectable signal.

[SSS] The device of paragraph [JJJ], wherein the device performs an immunoassay wherein an antibody-protein complex is formed.

[TTT] The device of paragraph [SSS], wherein the immunoassay is a serological immunoassay.

[UUU] The device of paragraph [SSS], wherein the immunoassay is a nephrelometric immunoassay

[VVV] The use of any of the devices of paragraphs [JJJ]-[SSS] for facilitating the diagnosis of membranous nephropathy in a subject, wherein a detectable amount of antibodies that are reactive to a PLA2R indicates likelihood of membranous nephropathy in the subject.

[WWW] A kit comprising a device of paragraph [JJJ] and a detection antibody, wherein the detection antibody is specific for the antibodies that are reactive to a PLA2R in the sample of the subject and produces a detectable signal.

[XXX] A kit comprising a device of paragraph [JJJ] and a second labeled PLA2R protein or fragments thereof that produces a detectable signal.

[YYY] A kit comprising a device of paragraph [JJJ] and a nephelometer cuvette.

[ZZZ] A system comprising:
   a. a measuring module measuring auto-antibody information comprising a detectable signal from an immunoassay indicating the presence or level of antibodies that are reactive to a PLA2R from a sample obtained form a subject;
   b. a storage module configured to store data output from the measuring module;
   c. a comparison module adapted to compare the data stored on the storage module with reference and/or control data, and to provide a retrieved content, and
   d. an output module for displaying the retrieved content for the user, wherein the retrieved content the presence of detectable amount of antibodies reactive against PLA2R indicates that the subject has MN or has a relapse of MN.

[AAAA] The system of paragraph [ZZZ], wherein the control data comprises data from a population of non-MN healthy individuals.

[BBBB] A system to facilitate the prognosis evaluation of MN in a subject, comprising:
   a. a determination module configured to receive and output auto-antibody information to a PLA2R from a sample obtained from a subject, wherein the auto-antibodies information measures the level of auto antibodies that are reactive to the PLA2R;
   b. a storage module configured to store output information from the determination module;
   c. a comparison module adapted to compare the data stored on the storage module with reference and/or control data, and to provide a comparison content, and
   d. an output module for displaying the comparison content for the user, wherein if there is no detectable amount of auto antibodies reactive against PLA2R then the subject is in remission or if there is a reduction of at least 10% to a prior reading, then the treatment for MN is effective in the subject.

[CCCC] The computer system of paragraph [BBBB], wherein the control data comprises previous data from the same subject wherein the previous data had indicated detectable amounts of auto-antibodies.

[DDDD] A computer readable storage medium comprising:
   a. a storing data module containing data from a sample obtained from a subject that represents a signal level from an immunoassay for antibodies that are reactive to a PLA2R;
   b. a comparison module that compares the data stored on the storing data module with a reference data and/or control data, and to provide a comparison content, and
   c. an output module displaying the comparison content for the user, wherein the presence of a detectable amount of antibodies reactive against PLA2R of at least 10% relative to the reference data and/or control data indicates that the subject has MN or has a relapse of MN.

[EEEE] The system of paragraph [DDDD], wherein the control data comprises data from a population of non-MN healthy individuals.

This invention is further illustrated by the following example which should not be construed as limiting. The contents of all references cited throughout this application, as well as the figures and table are incorporated herein by reference.

EXAMPLE

Materials and Methods

Human Sera

With approval from the Institutional Review Board at Boston University, we have collected and stored coded serum samples from patients with membranous nephropathy, other glomerular or autoimmune disorders, and normal volunteers. Those classified as having idiopathic MN have had biopsy-proved MN in the absence of traditional secondary features, such as positive anti-nuclear antibodies (ANA), anti-double-stranded DNA antibodies, or hepatitis B serologies. Further classification into these groups is discussed in the Supplemental Information.

Human Kidney Tissue

We obtained human kidneys that were unsuitable for transplantation and donated for research from the New England Organ Bank. Glomeruli were collected from minced kidney cortex by filtering through metal sieves (ref) and were resuspended and extracted in a detergent-containing RIPA buffer (Boston BioProducts, Boston, Mass.). Contaminating IgG was removed from this preparation via incubation with Immobilized Protein G Plus (Thermo Fisher). We used peptide N-glycosidase F (PNGase F; New England Biolabs) in the absence of reducing agent to remove N-linked sugar residues from the glomerular proteins when indicated. In order to partially purify the glomerular glycoproteins, we passed human glomerular extract over wheat germ agglutinin (WGA) agarose bead column (Vector Laboratories) and eluted the bound glycoproteins with 500 mM N-acetyl glucosamine (GlcNAc). Both native and the 200 kDa PNGase F-deglycosylated antigen were found to bind the column.

Western Blot Protocol

Human glomerular extract or cell-expressed human PLA2R was electrophoresed under non-reducing conditions and transferred to nitrocellulose membranes according to standard protocols. We immunoblotted with human serum as the primary antibody, typically at 1:100 to 1:250, and horseradish peroxidase-conjugated donkey anti-human IgG secondary antibody (Jackson ImmunoResearch) at 1:40,000. The PLA2R antibody used for these experiments is a polyclonal guinea pig antibody raised against the full-length purified rabbit PLA2 receptor. It recognizes the human protein under both reducing and non-reducing gel electrophoresis conditions (Granata, F., et al. 1995, J. Immunol. 174: 464-74; G. Lambeau, personal communication). We purchased sheep antibodies against the four IgG subclasses from The Binding Site and used them at the dilutions recommended by the manufacturer.

Mass Spectrometry Analysis and Data Interpretation

We excised gel regions of interest and performed in-gel trypsin digestion as previously described in Powell, 2003 Mol Cell Biol 23:5376-5387. We analyzed the resulting peptides with a modified version of a previously described method that couples liquid chromatography (LC) with tandem mass spectrometry (MS/MS) (Powell, 2004, Mol Cell Biol 24:7249-7259). We used the acquired MS data to search the NCBI RefSeq Human database using the SEQUEST algorithm and analyzed the data with SequestSorcerer™ (Sage-N Research, San Jose, Calif.). The enrichment or relative abundance of each identified protein was determined by normalizing the number of spectral counts matching to the protein by its predicted molecular weight. This value has been termed a Protein Abundance Factor (PAF) (Powell, 2004, Mol Cell Biol 24:7249-7259).

Immunohistology

We froze fresh sections of human kidney in Optimal Cutting Temperature solution (TissueTek) and cut 4 micron sections with a cryotome. We obtained serial frozen sections from five MN kidney biopsies from Dr. Helmut Rennke (Boston, Mass.). We fixed and permeabilized the sections with methanol:acetone and blocked with 10% bovine serum albumin in TBS. To detect PLA2R, we used guinea-pig anti-rabbit PLA2R at 1:400 and Cy3-conjugated donkey anti-guinea pig IgG (Jackson ImmunoResearch) at 1:500. To demonstrate specificity of the staining, we precleared the polyclonal antibody with a fragment of rabbit PLA2R containing the 4th to 6th lectin-binding domains. This significantly depleted the immunofluorescence signal to PLA2R.

The diagnosis of membranous nephropathy was established by renal biopsy in all cases. Those classified as idiopathic MN had no evidence of secondary features, which include positivity for anti-nuclear antibodies or anti-double stranded DNA, hepatitis B antigenemia, or electron-dense deposits on renal biopsy in locations other than subepithelial. We did not make an attempt to rule-out occult malignancy as a potential cause of secondary MN. The other glomerular disorders were diagnosed by biopsy (2 FSGS; 1 DN; 1 Henoch-Shonlein purpura) or by clinical features. These included longstanding MN with gradually-progressive proteinuria, orthostatic proteinuria evidenced by split urine collections. The patients with additional autoimmune or rheumatologic conditions included systemic lupus erythematosus without significant proteinuria, dermatomyositis, scleroderma/mixed connective tissue overlap disease, and bullous pemphigus.

Given the size similarity to IgG, we initially excluded IgG as the target of what could have been a rheumatoid factor-like activity in the membranous serum. Glomerular extracts were treated with protein G-linked agarose beads to remove contaminating IgG that was invariably present in the glomerular extract. Conversely, MN sera were incubated with heat-aggregated IgG covalently linked to Affi-Gel 10 beads to pre-adsorb out any serum factors that were reactive with IgG. Serum samples treated in his manner demonstrated an identical reactivity with the 200 kDa antigen as did the starting serum (data not shown). Additionally, we were able to show subtle differences in migration between IgG and the MN-Ag on low percentage (6%) agarose gels run for extended periods of time, and did not note a major shift in the size of IgG when treated with PNGase F. Despite our confidence that the target antigen was not an immunoglobulin, the size similarity to human IgG and the necessity of running the gels under non-reducing conditions in order to detected the antigen made immunoprecipitation of the MN-Ag nearly impossible, despite varied approaches. We therefore approached the task of identifying this putative target antigen in membranous nephropathy (MN-Ag) using biochemical purification techniques.

Results

MN Sera React with a 200 KDA Glomerular Protein

Our approach to the identification of the target antigen in human membranous nephropathy was based on the presumption that autoantibodies in the serum of patients with MN would identify candidate bands by standard western blotting of human glomerular proteins. A consistently-identified band was not detected until we fortuitously electrophoresed the proteins under non-reducing conditions, when a prominent, approximately 200 kDa band was detected by several of sera that had previously been negative using the more-standard reducing conditions. Testing of other banked and newly-collected sera from patients with idiopathic MN showed similar reactivity in over 50% of such patients. In FIG. 1A, the five MN sera all recognize a band of approximately 200 kDa, whereas the sera from the nephrotic control patients do not. In the lower panel of FIG. 1A, these five reactive MN sera are used to western blot alternating lanes of native and deglycosylated (PNGase F+) glomerular proteins. All five MN sera react identically with the 200 kDa native antigen and an approximately 150 kDa deglycosylated protein. Strikingly, serum from normal volunteers (n=23), patients with other nephrotic conditions such as diabetic nephropathy FSGS (n=13), or patients with other autoimmune, rheumatologic disorders (n=6) were all non-reactive toward this antigen when assayed under identical conditions. Further analysis of the patients with MN revealed that none of the eight cases of secondary MN (6 lupus-associated and 2 hepatitis B-associated) were reactive for the 200 kDa antigen. Removal of N-linked carbohydrate chains with peptide N-glycosidase (PNGase) F caused a significant shift in mobility of this antigen to approximately 150 kDa, indicating that it is heavily glycosylated. All sera initially reactive with the native 200 kDa band also identified the smaller, deglycosylated band (FIG. 1A).

To verify the specificity of anti-PLA2Rautoantibodies positive reactivity for idiopathic membranous nephropathy, we have increased the number of samples from subjects tested for antibodies to PLA2R by western blotting. We also increased the controls to n=32 and patients with other nephrotic conditions such as diabetic nephropathy FSGS (n=25). In addition to an increase in the number of subjects with idiopathic MN in Boston (MA, USA), we have received and tested samples from the Mayo Clinic in Rochester, (MN, USA), the University of Lund in Sweden, and the University in the Netherlands. We have also increased the number of control samples from patients with secondary MN, other autoimmune and kidney diseases, as disease controls and normal subjects. Approximately 72-82% of patients with idiopathic MN tested positive for anti-PLA2R antibodies whereas none of the normal or disease controls, or patients with secondary forms of MN was positive (FIG. 1C).

Given the evidence of significant glycosylation, we tested the ability of the antigen to bind various lectin columns, and found that it bound to wheat-germ agglutinin (WGA) in both its native and N-deglycosylated form. The binding of both forms may reflect residual N-linked carbohydrates that are inaccessible to PNGaseF under the non-reducing conditions required to maintain antigenicity. Native and deglycosylated human glomerular proteins were eluted from WGA and electrophoresed; the two gel regions corresponding to the 200 and 150 kDa antigen bands on WB were excised, subjected to in-gel tryptic digestion and analyzed by mass spectrometry. Under the assumption that peptide sequences corresponding to the putative target antigen would be identified in both samples, we generated a list of candidate identities for the putative MN antigen (see Table 1). Using available antibodies and/or recombinant proteins, we assessed these candidate antigens and were fortunate to encounter a possible match when antibodies to the M-type phospholipase A2 receptor identified a similarly-sized protein in human glomeruli (FIG. 2A).

Phospholipase A2 Receptor in the Target Antigen in MN

Figure 2A:
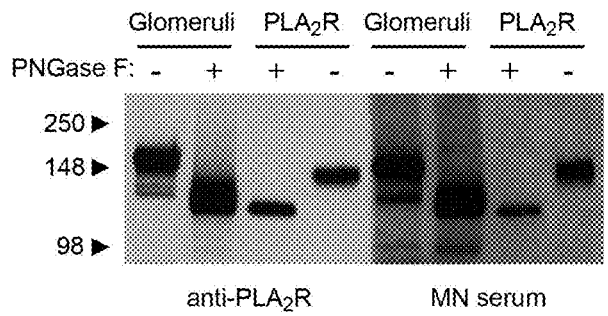
FIG. 2A shows the 200 kDa antigen in human glomeruli is the M-type phospholipase A2 receptor (PLA2R). Human glomerular proteins and recombinant PLA2R treated with or without PNGase F and western blotted with either reactive MN serum or a polyclonal antibody raised against PLA2R are shown.

Both MN serum and the anti-PLA2R recognize identical bands in WB (Western blots) of glomeruli extracts (FIG. 2A). The recombinant protein migrates to a slightly lower position than the native glomerular protein, although deglycosylation with PNGase F causes both to migrate to the same position. Cell-expressed recombinant human PLA2R (rPLA2R) blotted with MN sera yielded a distinct band on WB that was slightly smaller than the corresponding signal from human glomeruli. However, when both samples were deglycosylated, they migrated to the same position (FIG. 2A). This suggests a small difference in overall glycosylation between the native protein and the recombinant form. Importantly, WB of these same samples with a monospecific polyclonal antibody against PLA2R revealed an identical pattern. We have since confirmed that all MN samples that reactive with the 200 kDa glycoprotein from human glomeruli also recognize rPLA2R, confirming that the 200 kDa band from human glomeruli that we had been investigating was indeed PLA2R.

Figure 2B:
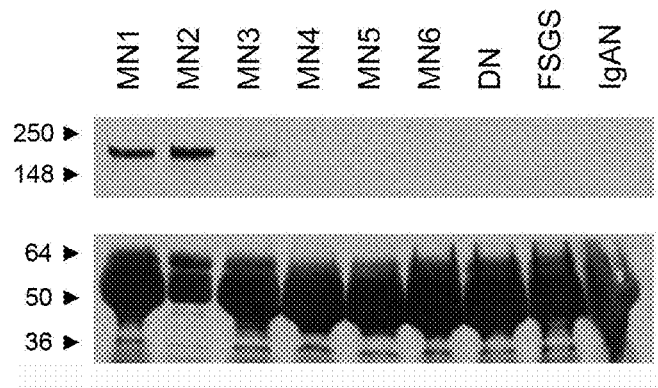
FIG. 2B demonstrates that human MN sera can immunoprecipitate (IP) PLA2R. Three reactive and three non-reactive sera from MN patients, as well as three control sera, were used to IP the target antigen from a mixture of human glomerular proteins. The immunoprecipitates were then western blotted with antibodies to PLA2R (top) as well as to total human IgG (bottom panel).

Human sera that are reactive with the 200 kDa MN-Ag by WB can immunoprecipitate (IP) PLA2R from human glomerular extracts (FIG. 2B). All three reactive MN sera are able to IP PLA2R from both human and pig glomerular protein extracts, whereas the controls do not. Appreciable amounts of starting IgG were present in all cases; the amount is lower in lane 2 as this patient was particularly nephrotic. Two of the three non-reactive sera and all three nephrotic control sera did not IP PLA2R under identical conditions. Interestingly, with one of the sera initially found to be non-reactive by WB, a faint band was detected by IP (not visible in the reproduction). When the serum was re-assayed at a 1:25 dilution, it was found to identify rPLA2R by WB (data not shown). This may suggest that other MN patients initially thought not to have anti-PLA2R autoantibodies may instead have low-level titers not easily detectable by our initial WB assay (screening is typically done at a 1:100 serum dilution).

Figure 2C:
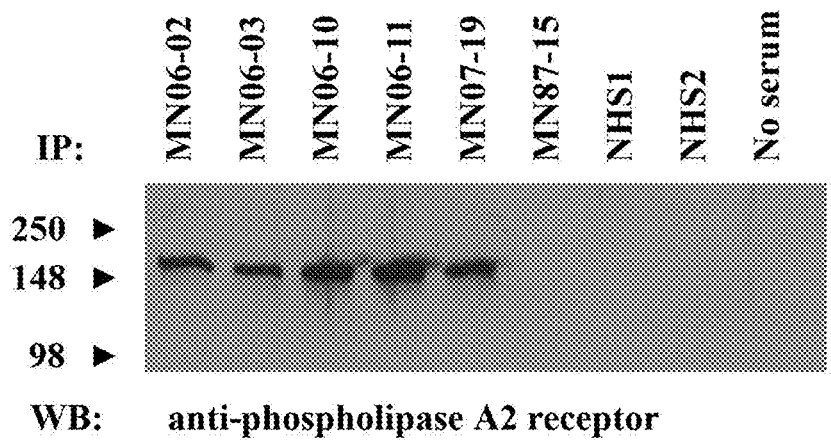
FIG. 2C shows that the glomerular glycoprotein identified by reactive MN sera is the human PLA2R. Whole human serum was used to immunoprecipitate (IP) glomerular proteins, and the IP's were then electrophoresed and Western blotted with an antibody specific to the M-type PLA2R. The first five lanes show IP's with sera that were known to be positive by WB (as in FIG. 1). The 6th lane represents an IP with serum from a patient with MN that was known to be negative. Lanes 7 and 8 show IP's with serum from normal volunteers, and in the final lane, human serum was omitted from the IP to rule out non-specific binding of glomerular proteins to the agarose beads.

In addition, FIG. 2C shows that the glomerular glycoprotein identified by reactive MN sera is the human phospholipase A2 receptor. Whole human serum was used to immunoprecipitate (IP) glomerular proteins, and the IP's were then electrophoresed and Western blotted with an antibody specific to the M-type phospholipase A2 receptor. The first five lanes show IP's with sera that were known to be positive by WB (as in FIG. 1). The 6th lane represents an IP with serum from a patient with MN that was known to be negative. Lanes 7 and 8 show IP's with serum from normal volunteers, and in the final lane, human serum was omitted from the IP to rule out non-specific binding of glomerular proteins to the agarose beads.

Figure 3A:
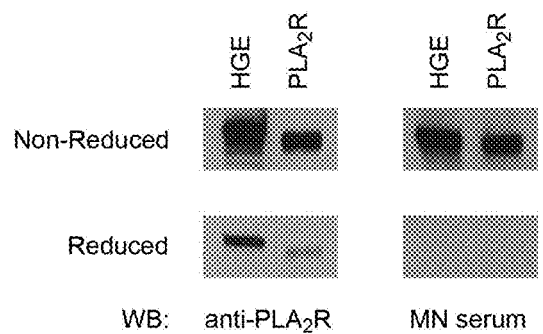
FIG. 3A shows the epitope on PLA2R is reduction sensitive and elicits an IgG4 predominant response.

Recombinant PLA2R shares the reduction-sensitive epitope as does the native glomerular protein (FIG. 3A). In the WB in which equal amounts of human glomerular extract (HGE) were electrophoresed under reducing and non-reducing conditions; recombinant PLA2R was treated similarly. WB was performed with reactive MN serum or a polyclonal anti-PLA2R antibody and detected with appropriate secondary antibodies. The reactivity towards the native or recombinant PLA2R is in the non-reduced state, for both MN serum and the polyclonal anti-PLA2R were noted. However, while anti-PLA2R recognizes the antigen in reduced form, MN serum fails to detect the reduced native or recombinant protein. Both the monospecific anti-PLA2R antiserum and MN sera strongly detect recombinant and native glomerular PLA2R by WB under non-reducing conditions. Whereas the polyclonal antibody still detects both forms (albeit less robustly) when run under reducing conditions, MN sera fail to react with either form.

Figure 3B:
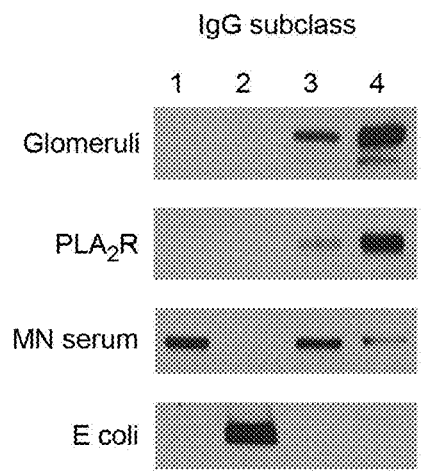
FIGS. 3B and 3C shows that the IgG subclass specificity of the auto-antibodies reactive to PLA2R.
Figure 3C:
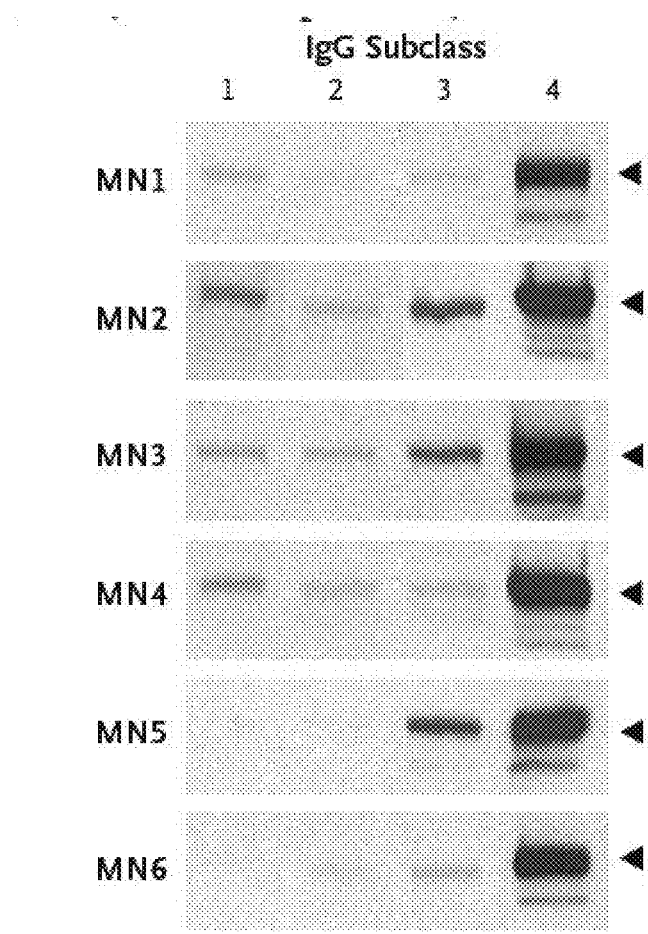

The IgG classes of the auto antibodies reactive against PLA2R, human glomerular proteins, recombinant PLA2R, and antigens from *E. coli* were blotted with a single reactive MN serum, followed by antibodies specific for the IgG subclasses. The predominant subclass that reacts with native or PLA2R is IgG4, whereas it is IgG2 for a 70 kDa *E. coli* protein included as a control. The relative amounts of IgG subclasses in this particular serum were assessed by WB of diluted total serum with the subclass-specific antibodies. The IgG2 form is not well-detected in its denatured form, but is clearly present as detected by its binding to the 70 kDa *E. coli* protein. It is well established that the IgG antibodies that are detected by immunofluorescence microscopy in the glomeruli of patients with idiopathic MN are of the IgG4 subclass. Here we found that the IgG antibodies in the serum of patients with idiopathic MN that reacted with PLA2R were also of the IgG4 subclass. We have further confirm this observations in additional serum from 6 patients diagnosed with idiopathic MN. Human glomerular extract (HE) was blotted initially with serum samples from six patients with idiopathic MN (MN1 through MN6), followed by sheep antibodies specific for each human IgG subclass (1 through 4), and was detected with peroxidase conjugated antisheep IgG antibody. The predominant IgG subclass that reacted with the native antigen was IgG4, with varying amounts of reactivity seen for IgG1, IgG2, and IgG3. Identical results were obtained with the use of recombinant PLA2R instead of HGE (data not shown). The immunoglobulin response in membranous nephropathy is typical of a Th2 response, with a predominance of IgG4 subclass (Kuroki, 2005, Kidney Int 68:302-310). When either human glomerular proteins or rPLA2R are immunoblotted with appropriately-reactive MN patient serum, the predominant subclass detected by WB is IgG4 (FIG. 3B), whereas it is IgG2 for an unrelated bacterial antigen.

Glomerular Location of the Phospholipase A2 Receptor

The proposed pathomechanism for human MN is that autoantibodies bind in situ to an antigen present on the podocyte. Because PLA2R has been described in a soluble form, we first discounted the possibility that circulating antibody-PLA2R complexes were being trapped in the GBM. Neither MN sera nor control sera had any detectable PLA2R, even after enrichment by means of lectin binding (data not shown). Nor could we detect circulating immune complexes of PLA2R-IgG through either precipitation with polyethylene glycol 6000 or protein G immunoprecipitation of IgG in serum samples from either group. Conversely, we were able to detect the presence of PLA2R on podocytes by immunofluorescence with the monospecific anti-PLA2R antibody. Frozen sections of normal human kidney cortex were co-stained with anti-agrin followed by a FITC-conjugated anti-rabbit secondary antibody, to label the glomerular basement membrane (GBM) and anti-PLA2R followed by CY3-conjugated anti-guinea pig secondary antibody (data not shown). We found that the PLA2R signal is clearly present external to the GBM, and localizes to both the cell body and processes of the podocyte. This staining is markedly reduced when the antibody is precleared with a recombinant fragment of PLA2R containing CRD domains 4-6 (data not shown). The staining pattern is granular, and extends from the cell body to the basal foot processes. When cryosections are stained by dual immunofluorescence with antibodies against PLA2R and agrin, a component of the glomerular basement membrane (GBM), the podocyte signal is clearly seen immediately adjacent and external to the GBM. The majority of glomerular and podocyte PLA2R staining can be blocked by preincubation of the antibodies with recombinant PLA2R fragments containing CTLDs 4, 5, and 6.

Next we studied the localization of the anti-PLA2R IgG4 in glomerulus. The PLA2R is present in a granular pattern in membranous nephropathy biopsy specimens, and colocalizes with IgG4. A frozen section of a biopsy specimen from a patient diagnosed with MN reveals PLA2R and IgG4 that colocalize well in the peripheral capillary walls and GBM (data not shown). A serial section of the same patient is stained in the same manner, although the anti-IgG4 antibody was omitted to exclude the possibility that the anti-sheep secondary antibody was detecting guinea pig or donkey IgG, or that bleed through from the Cy3 channel was causing the signal seen previously. In contrast to podocytes, mesangial cells in normal human kidney tissue did not show staining for PLA2R (data not shown).

Studies in the rat Heymann nephritis model have suggested that "capping and shedding" of receptor-antibody complexes are deposited subepithelially into the GBM, and we anticipated that the same is true in the case of PLA2R in human MN. PLA2R is present in a fine granular pattern lining the GBM upon immunofluorescence of cryosections from kidney biopsy specimens obtained from patients with MN. This could be blocked with the blocking fragment of recombinant PLA2R. Although the intensity of staining varied between the four patient samples we examined, all revealed the same granular pattern for PLA2R (data not shown). Of interest, PLA2R staining of the podocyte cell body, which had been strong in normal glomerular sections, was greatly attenuated in the MN biopsy samples. Moreover, the GBM staining pattern closely matched that of IgG4 on dual immunofluorescence.

Figure 4A:
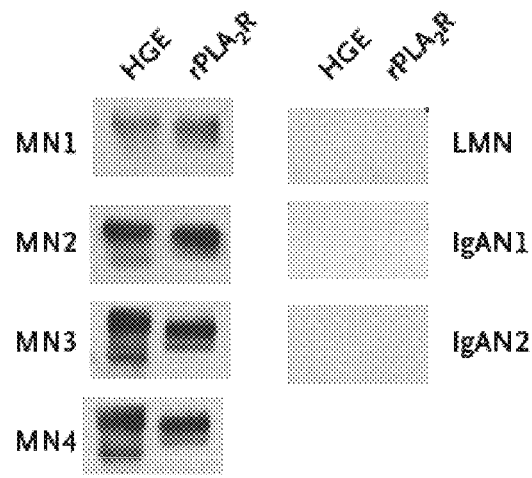
FIG. 4A shows that only IgG eluted from the MN samples identified the native and recombinant PLA2R.
Figure 4B:
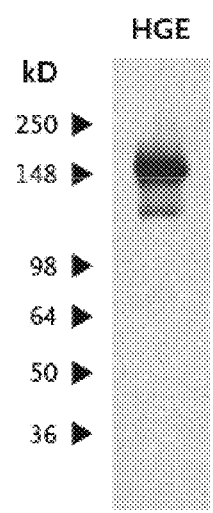
FIG. 4B shows that the IgG eluted from the MN3 biopsy sample recognized only those bands corresponding to PLA2R

Immunofluorescent microscopy showed that anti-PLA2R and IgG4 co-localize in the glomeruli of patients with idiopathic MN but not lupus-associated MN. To confirm that the IgG in the glomeruli from patients with membranous nephropathy was reactive with PLA2R, we eluted IgG from biopsy specimens and used it in Western blotting with native and recombinant PLA2R. IgG was successfully eluted from four biopsy samples from patients with idiopathic membranous nephropathy, one from patients with lupus membranous nephropathy, and two from patients with IgA nephropathy. The IgG eluted from the samples from patients with idiopathic membranous nephropathy specifically detected the appropriately sized PLA2R bands in human glomerular extract and cell lysates that were positive for recombinant PLA2R (FIGS. 4A and 4B), whereas the IgG eluted from the three other samples from patients with immune-complex glomerular disease did not. IgG was eluted from biopsy cores from patients with idiopathic MN (MN), lupus MN (LMN), or IgA nephropathy (IgAN). This eluted IgG was used to immunoblot human glomerular extract (HGE) or recombinant PLA2R (rPLA2R).

Association with Disease Activity

Figure 5A:
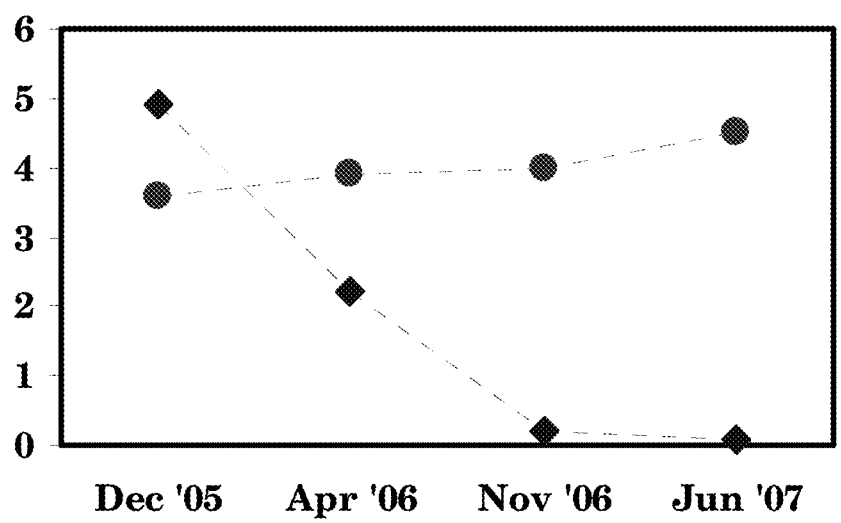
FIG. 5A shows the presence of anti-PLA2R antibody in patient serum correlates with disease activity. Serial sera were collected from a single patient with MN who entered remission. The top graph shows a decline in urinary protein levels (diamonds) and an increase in serum albumin (circles).
Figure 5B:
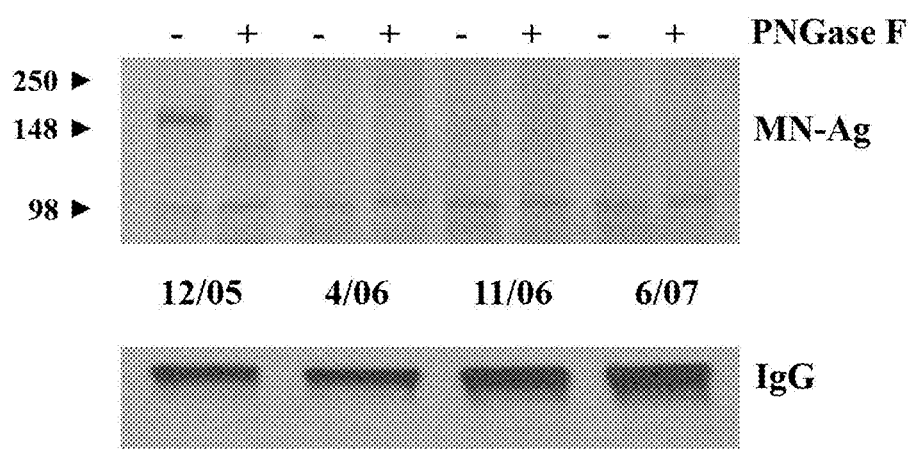
FIG. 5B shows the WB in the top panel shows that reactivity to the 200 and 150 kDa native and deglycosylated PLA2R is only present in the initial sample form the same patient of FIG. 5A. Equal loading is shown by the non-specific detection of a 98 kDa band. Total IgG in the serum samples is shown in the bottom panel, demonstrating a slight increase in IgG as the patient entered remission from MN.

We have obtained serial serum samples when possible, and have examined the change in reactivity in several individuals who have achieved treatment or spontaneous remission, or alternatively, relapse. The presence of autoantibodies to PLA2R, in general, parallels the clinical significant disease activity as measured by urinary protein and serum albumin (FIGS. 5 and 6). Importantly, a decline or disappearance of anti-PLA2R antibody can be seen prior to a disappearance of proteinuria. This is understandable given the time required for clearance of immune deposits and recovery of the podocyte architecture and functional slit diaphragms.

Figure 6A:
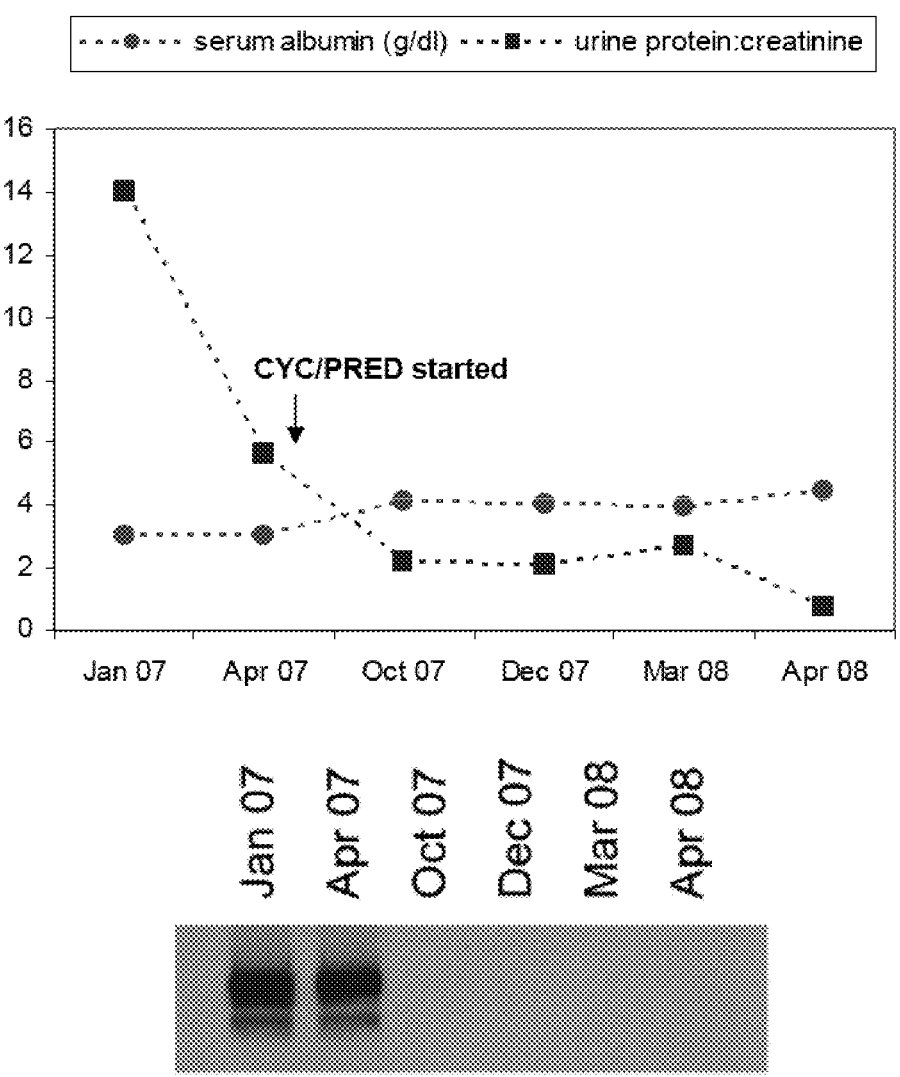
FIG. 6A shows that sera reactivity to PLA2R corresponds to disease activity in patient A with idiopathic MN. The graph shows the decline in protein in urine upon treatment and the concomitant disappearance of anti-PLA2 antibodies after treatment commencement in the Western Blot.

We have studied additional patients before and after treatment-induced remission. We found that patients that were positive for anti-PLA2R before treatment became negative after remission was induced with immunosuppressive treatment (FIGS. 6A and B). The filled squares in the graph represent urine protein excretion. After treatment was started with cyclophosphamide and prednisone, urine protein excretion declined and reactivity to PLA2R disappeared as shown in the western blot. Similar results have been found in patients treated with rituximab and synthetic ACTH.

These findings support the utility of using an immunoassay to PLA2R not only for diagnosis of MN, but also for monitoring disease activity during treatment or while awaiting a spontaneous remission.

In conclusion, we have identified the M-type phospholipase A2 receptor as the major target antigen in the autoimmune glomerular disease, idiopathic membranous nephropathy. The protein is present on normal human podocytes, and over fifty percent of patients with MN bear antibodies reactive with this protein. Furthermore, the protein is present within immune deposits in biopsy specimens of patients. Levels of antibody against PLA2R appear to correlate with disease activity, and may prove to be a useful method for initial diagnosis of MN and for following disease activity with treatment or while waiting for spontaneous remission.

All references, including any patents or patent applications cited in this specification, as well as the figures and table, are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in the United States of America or in any other country.

EXAMPLE 2

Figure 8A:
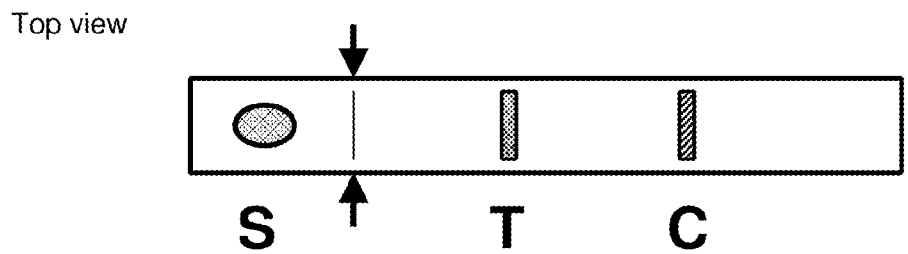
FIGS. 8A (top view) and 8B (side view) shows the schematic diagrams of a test strip for determining the presence and/or level of auto-antibodies reactive against PLA2R in a fluid sample.

The levels of anti-PLA2R auto-antibodies described herein can also be determined using test strips as illustrated in FIG. 8-9. In the test strip, the membrane is divided into three separate regions: a sample (S) position at one end of the membrane, a test (T) position located at the middle of the membrane, and a control (C) position found at the opposite end the membrane (FIG. 8A). Located at S is an excess quantity of dehydrated PLA2R. The PLA2R can be conjugated to colloidal gold beads or latex beads for visualization purposes. At T, there is an excess quantity of anti-IgG immobilized on the membrane. At C, there is another immobilized anti-PLA2R antibody (FIG. 8A).

The excess quantity of dehydrated PLA2R at S position is such that when a sample (e.g. serum) is applied at S, anti-PLA2R antibody and PLA2R complexes are formed and free PLA2R are still available to bind the immobilized anti-PLA2R at position C.

The S position is where a sample of serum is applied. The arrowheads delineate the boundary limit that the sample serum should not cross on the membrane when applying the serum to the membrane. The water in the serum rehydrates the PLA2R. An antibody-protein complex is produced when the auto-antibody reactive to PLA2R forms a complex with the rehydrated PLA2R. A mixture of the antibody-protein complexes and non-complexed PLA2R move by capillary action away from position S towards position T and C.

Upon arrival at the T position, the antibody-protein complex will bind the immobilized anti-IgG antibody and be immobilized at the T position. The localized concentration of antibody-protein complex that is colloidal gold or latex bead labeled will become visible as a colored line at the T position (FIG. 9, middle). The greater the amount of auto-antibodies in the sample, the broader the visible band at T. When the area remains clear at the T position, this means that there is are anti-PLA2R auto-antibodies (FIG. 9, left). At the C position the free and labeled PLA2R will be bound and captured by the immobilized anti-PLA2R antibody. This will in turn result in a concentration of a colloidal gold or latex bead labeled PLA2R at the C position and will become visible as colored line at the C position. The C position result serves as a test control that there is functional PLA2R in the test material and should always be present (FIG. 9, right).

Figure 8B:
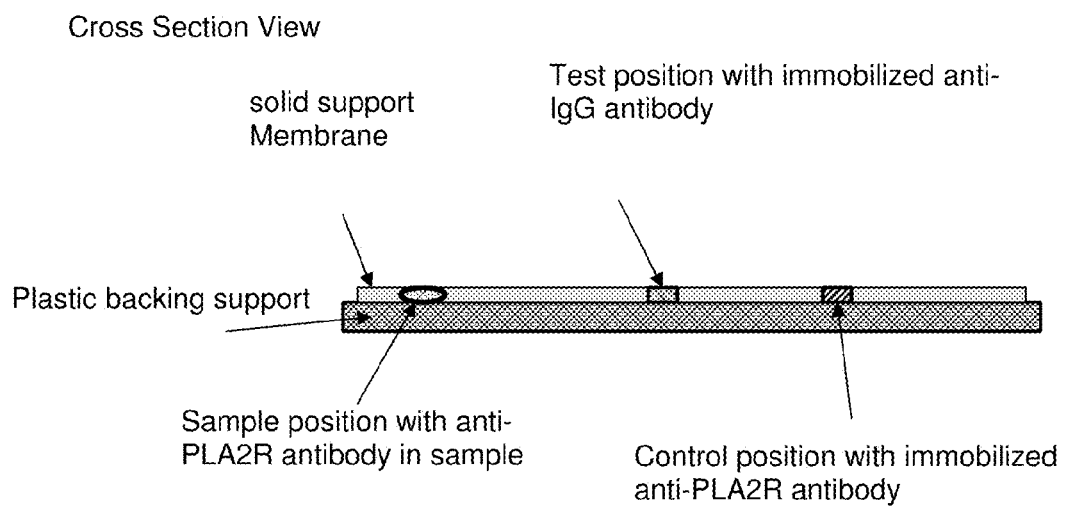

The test strip can be designed in a form of a dipstick test strip (FIG. 8B). As a dipstick test strip, the strip is dipped into a sample of serum at the S position end with sample level not to exceed the boundary limit. The strip is then laid horizontally with the membrane surface facing up on a flat surface. A fixed amount of time is given for the antibody re-hydration, capillary action, and antibody binding reaction to take place. At the end of the fixed time, there should be visible bands at the C position and depending on the level of auto-anti-PLA2R antibody, there may or may not be a visible band at the T position (FIG. 9).

EXAMPLE 3

Figure 10:
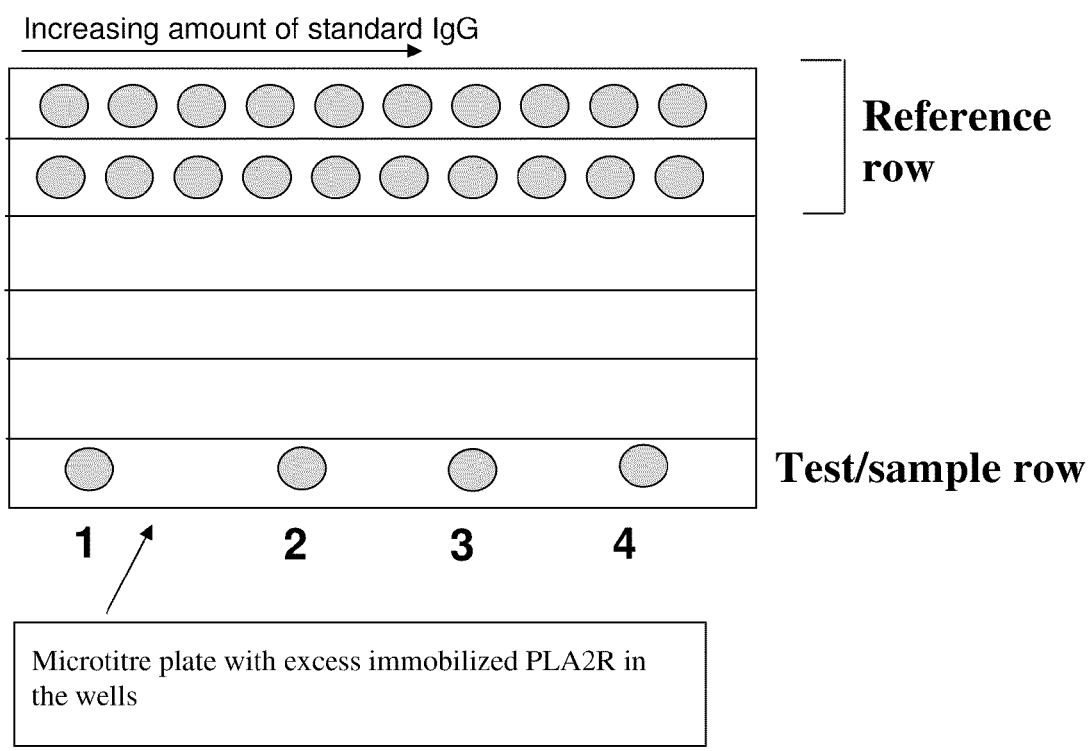
FIG. 10 shows a schematic diagram of an ELISA plate assay comprising standard PLA2R curves.

The levels of anti-PLA2R auto-antibodies described herein can be determined using an ELISA assay as illustrated in FIG. 10. An ELISA assay comprises performing a standard titration assay and a sample assay in order to determine the amount of anti-PLA2R auto-antibodies in a sample obtained from a subject. As shown, the ELISA assay microtiter plate consists of two duplicate reference rows for increasing amounts of IgG protein. Standard amounts of IgG protein ranging from 0-50 ng/ml or pg/ml are placed in the reference rows to create a standard curve for human IgG. Excess amounts of PLA2R are immobilized in the sample wells of plate. The serum sample is placed in the sample wells. Subsequently, a horse-radish peroxidase labeled anti-human IgG antibody is added to the wells. The mixtures in the wells are allowed to incubate at room temperature for 90 min and the liquid is decanted. The wells are washed five times with deionized water. Then an aliquot of 3,3',5,5' tetramethylbenzidine (TMB) reagent is added into each well. The mixture is gently mixed for 10 seconds and incubated at room temperature (18-25° C.) for 20 minutes. The enzymatic reaction is terminated by adding 1N HCl. Gentle agitation is carried out till all the blue color changes to yellow color completely. The amount of color by-product is determined by reading its absorbance at 450 nm with a microtiter well reader. The $A_{450}$ correspond to the amount of human IgG antibodies in the wells. The amount of the anti-PLA2R auto-antibodies in a test sample can be estimated from the $A_{450}$ obtained from the sample wells and the standard curve obtained from the reference wells.

In an alternate embodiment, the modified ELISA assay as shown in FIG. 11 can be used. As in FIG. 10, the reference rows and sample wells are labeled (FIG. 11). Excess amounts of PLA2R are immobilized in the wells of plate. A fixed amount of IgG is placed in duplicate reference wells. This fixed amount is the reference value corresponds to the average amount of the anti-PLA2R auto-antibodies found in the serum of non-MN healthy subjects. The sample, serum, is also placed in the duplicate sample wells. The assay plate is process as described herein. The $A_{450}$ obtained from the sample wells are compared with those obtained for the corresponding reference rows in order to determine whether there is an increase or decrease in the amount of anti-PLA2R auto-antibodies in the serum sample.

TABLE 1

| Protein | Accession number | Size (aa) |
|---|---|---|
| Chondroitin sulfate proteoglycan 4 | NP_001888.2 | 2322 |
| KIAA0960 | NP_056019 | 1657 |
| M-type phospholipase A2 receptor | NP_031392.3 | 1463 |
| CD109, Gov system platelet alloantigen | NP_598000.2 | 1445 |
| Crumbs homolog 2 | NP_775960.4 | 1285 |
| Nephrin | NP_004637.1 | 1241 |
| Integrin, alpha 1 subunit | NP_852478.1 | 1179 |
| Integrin, alpha 3 subunit | NP_002195.1 | 1051 |
| Membrane alanine aminopeptidase | NP_001141.2 | 967 |
| Aminopeptidase A | NP_001968.3 | 957 |
| Integrin, beta 1 isoform 1D | NP_391988.1 | 801 |
| Neutral endopeptidase | NP_009218.2 | 750 |
| Endoglin isoform 2 | NP_000109.1 | 625 |
| Podocalyxin-like isoform 2 | NP_005388.2 | 526 |

Partial list of human glomerular proteins identified by mass spectrometry based on spectra from peptides common to the approximately 200 kDa and 150 kDa regions of the gel. The proteins are arranged according to their predicted size, given in amino acids (aa). Proteins represent both podocyte proteins (nephrin, alpha 3 integrin, neutral endopeptidase) and endothelial proteins (endoglin).

What is claimed:

1. An assay comprising:
   a. measuring a level of antibodies that are reactive to a phospholipase A2 receptor (PLA2R) in a blood sample obtained from a patient who presents at least one symptom of idiopathic membranous nephropathy (MN) for determining the likelihood of idiopathic MN in the patient; and
   b. comparing the level of the antibodies in the blood sample with a control data, wherein a detectable increase of at least 10% increase in the antibodies that are reactive to PLA2 in the blood sample over that of the control data indicates the likelihood of MN in the patient.

2. The assay of claim 1, wherein the level of PLA2R antibodies is measured by the steps comprising:
   a. contacting the blood sample from the patient with a PLA2R or PLA2R fragment thereof;
   b. forming an antibody-protein complex between the antibody present in the blood sample with the PLA2R or PLA2R fragment thereof;
   c. washing to remove any unbound antibody;
   d. adding a detection antibody that is labeled and is reactive to the antibody from the blood sample;
   e. washing to remove any unbound labeled detection antibody; and
   f. converting the label to a detectable signal, wherein the detectable signal indicates the level of PLA2R antibodies in the blood sample of the patient.

3. The assay of claim 2, wherein the PLA2R or PLA2R protein fragment thereof is deposited or immobilized on a solid support.

4. The assay of claim 3, wherein the support is in the format of a dipstick, a test strip, a latex bead, a microsphere or a multi-well plate.

5. The assay of claim 4, wherein the detection antibody is labeled by covalently linking to an enzyme, label with a fluorescent compound or metal, or label with a chemiluminescent compound.

6. The assay of claim 1, wherein the level of PLA2R antibodies is obtained by measuring a light scattering intensity resulting from the formation of an antibody-protein complex formed by a reaction of the blood sample with a PLA2R or PLA2R protein fragment thereof, wherein the light scattering intensity of at least 10% above a control light scattering intensity indicates the likelihood of idiopathic MN or relapse of MN in the patient, and wherein the control light scattering intensity is that of PLA2R or PLA2R protein fragment in the absence of blood sample.

7. The assay of claim 1, wherein the patient previously has been successfully treated for idiopathic MN.

8. The assay of claim 7, wherein the level of PLA2R antibodies is obtained by measuring a light scattering intensity resulting from the formation of an antibody-protein complex formed by a reaction of the blood sample with a PLA2R or PLA2R protein fragment thereof, wherein the light scattering intensity of at least 10% above a control light scattering intensity indicates the likelihood of idiopathic MN recurring in the patient, and wherein the control light scattering intensity is that of PLA2R or PLA2R protein fragment in the absence of blood sample.

9. An assay comprising:
   a. measuring a level of antibodies that are reactive to a phospholipase A2 receptor (PLA2R) in a blood sample obtained from a patient who previously has been successfully treated for idiopathic membranous nephropathy (MN) for determining the likelihood of relapse of idiopathic MN in the patient,
      wherein the level of PLA2R antibodies is measured by the steps comprising:
         contacting the blood sample from the patient with a PLA2R or PLA2R fragment thereof;
         forming an antibody-protein complex between the antibody present in the blood sample with the PLA2R or PLA2R fragment thereof;
         washing to remove any unbound antibody;
         adding a detection antibody that is labeled and is reactive to the antibody from the blood sample;
         washing to remove any unbound labeled detection antibody; and
         converting the label to a detectable signal, wherein the detectable signal indicates the level of PLA2R antibodies in the blood sample; and
   b. comparing the level of the antibodies in the blood sample with a control data, wherein a detectable increase of at least 10% in the antibodies that are reactive to PLA2R in the blood sample over that of the control data indicates the likelihood of relapse of idiopathic MN.

10. The assay of claim 9, wherein the patient presents a symptom of idiopathic MN.

11. The assay of claim 9, wherein the PLA2R or PLA2R protein fragment thereof is deposited or immobilized on a solid support.

12. The assay of claim 11, wherein the support is in the format of a dipstick, a test strip, a latex bead, a microsphere or a multi-well plate.

13. The assay of claim 12, wherein the detection antibody is labeled by covalently linking to an enzyme, label with a fluorescent compound or metal, or label with a chemiluminescent compound.

14. An assay comprising:
   a. measuring a level of antibodies that are reactive to a phospholipase A2 receptor (PLA2R) in a blood sample obtained from a patient who previously has been successfully treated for idiopathic membranous nephropathy (MN) for determining the likelihood of relapse of idiopathic MN in the patient,
      wherein the level of PLA2R antibodies is obtained by measuring a light scattering intensity resulting from the formation of an antibody-protein complex formed by a reaction of the blood sample with a PLA2R or PLA2R protein fragment thereof, wherein the light scattering intensity indicates the level of PLA2R antibodies in the blood sample; and
comparing the light scattering intensity with a control light scattering intensity data, wherein the light scattering intensity of at least 10% above the control light scattering intensity indicates the likelihood of idiopathic MN relapse in the patient, and wherein the control light scattering intensity is that of PLA2R or PLA2R protein fragment in the absence of blood sample.

15. The assay of claim 10, wherein the symptom is nephrotic syndrome or proteinuria.

16. The assay of claim 1, wherein the symptom is nephrotic syndrome or proteinuria.

17. The assay of claim 1 further comprising selecting the patient for treatment for idiopathic MN without subjecting the patient to a kidney biopsy if there is a detectable increase of at least 10% in the antibodies that are reactive to PLA2R in the blood sample over that of the control data.

18. An assay comprising:
a. measuring a level of antibodies that are reactive to a phospholipase A2 receptor (PLA2R) in a blood sample obtained from a patient who presents at least one symptom of idiopathic membranous nephropathy (MN) for determining the likelihood of idiopathic MN in the patient;
b. comparing the level of the antibodies in the blood sample with a control data; and
c. if there is a detectable increase of at least 10% in the antibodies that are reactive to PLA2R in the blood sample over that of a control data, then selecting the patient for treatment for idiopathic MN without subjecting the patient to a kidney biopsy.

19. The assay of claim 18, wherein the symptom is nephrotic syndrome or proteinuria.

20. The assay of claim 19, wherein the level of PLA2R antibodies is by measured by light scattering or an immunoassay.

* * * * *

SEQUENCE LISTING

<160> NUMBER OF SEQ ID NOS: 7

<210> SEQ ID NO 1
<211> LENGTH: 1324
<212> TYPE: PRT
<213> ORGANISM: Homo sapiens

<400> SEQUENCE: 1

```
Met Leu Leu Ser Pro Ser Leu Leu Leu Leu Leu Gly Ala Pro
 1               5                  10                  15

Arg Gly Cys Ala Glu Gly Val Ala Ala Leu Thr Pro Glu Arg Leu
                20                  25                  30

Leu Glu Trp Gln Asp Lys Gly Ile Phe Val Ile Gln Ser Glu Ser Leu
                35                  40                      45

Lys Lys Cys Ile Gln Ala Gly Lys Ser Val Leu Thr Leu Glu Asn Cys
 50                      55                      60

Lys Gln Ala Asn Lys His Met Leu Trp Lys Trp Val Ser Asn His Gly
 65                      70                      75                      80

Leu Phe Asn Ile Gly Gly Ser Gly Cys Leu Gly Leu Asn Phe Ser Ala
                        85                      90                      95

Pro Glu Gln Pro Leu Ser Leu Tyr Glu Cys Asp Ser Thr Leu Val Ser
                    100                     105                     110

Leu Arg Trp Arg Cys Asn Arg Lys Met Ile Thr Gly Pro Leu Gln Tyr
                115                     120                     125

Ser Val Gln Val Ala His Asp Asn Thr Val Ala Ser Arg Lys Tyr
                130                     135                     140

Ile His Lys Trp Ile Ser Tyr Gly Ser Gly Gly Asp Ile Cys Glu
145                     150                     155                     160

Tyr Leu His Lys Asp Leu His Thr Ile Lys Gly Asn Thr His Gly Met
                        165                     170                     175

Pro Cys Met Phe Pro Phe Gln Tyr Asn His Gln Trp His His Glu Cys
                        180                     185                     190

Thr Arg Glu Gly Arg Glu Asp Asp Leu Leu Trp Cys Ala Thr Thr Ser
                    195                     200                     205

Arg Tyr Glu Arg Asp Glu Lys Trp Gly Phe Cys Pro Asp Pro Thr Ser
210                     215                     220

Ala Glu Val Gly Cys Asp Thr Ile Trp Glu Lys Asp Leu Asn Ser His
225                     230                     235                     240

Ile Cys Tyr Gln Phe Asn Leu Leu Ser Ser Leu Ser Trp Ser Glu Ala
                        245                     250                     255

His Ser Ser Cys Gln Met Gln Gly Gly Thr Leu Leu Ser Ile Thr Asp
                        260                     265                     270

Glu Thr Glu Glu Asn Phe Ile Arg Glu His Met Ser Ser Lys Thr Val
                    275                     280                     285

Glu Val Trp Met Gly Leu Asn Gln Leu Asp Glu His Ala Gly Trp Gln
                290                     295                     300

Trp Ser Asp Gly Thr Pro Leu Asn Tyr Leu Asn Trp Ser Pro Glu Val
305                     310                     315                     320

Asn Phe Glu Pro Phe Val Glu Asp His Cys Gly Thr Phe Ser Ser Phe
                        325                     330                     335

Met Pro Ser Ala Trp Arg Ser Arg Asp Cys Glu Ser Thr Leu Pro Tyr
                        340                     345                     350

Ile Cys Lys Lys Tyr Leu Asn His Ile Asp His Glu Ile Val Glu Lys
                    355                     360                     365
```

```
Asp Ala Trp Lys Tyr Tyr Ala Thr His Cys Glu Pro Gly Trp Asn Pro
    370                 375                 380

Tyr Asn Arg Asn Cys Tyr Lys Leu Gln Lys Glu Glu Lys Thr Trp His
385                 390                 395                 400

Glu Ala Leu Arg Ser Cys Gln Ala Asp Asn Ser Ala Leu Ile Asp Ile
            405                 410                 415

Thr Ser Leu Ala Glu Val Glu Phe Leu Val Thr Leu Leu Gly Asp Glu
        420                 425                 430

Asn Ala Ser Glu Thr Trp Ile Gly Leu Ser Ser Asn Lys Ile Pro Val
    435                 440                 445

Ser Phe Glu Trp Ser Asn Asp Ser Ser Val Ile Phe Thr Asn Trp His
    450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Arg
            485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
    515                 520                 525

Ile Asp Thr Val Leu Arg Ser Phe Asp Gln Ala Ser Ser Gly Tyr Tyr
530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
            565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
    595                 600                 605

His Gln Pro Arg Tyr Ser Gly Gly Cys Val Ala Met Arg Gly Arg His
    610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
            645                 650                 655

Glu Arg Trp Pro Phe His Pro Cys Tyr Leu Asp Trp Glu Ser Glu Pro
            660                 665                 670

Gly Leu Ala Ser Cys Phe Lys Val Phe His Ser Glu Lys Val Leu Met
    675                 680                 685

Lys Arg Thr Trp Arg Glu Ala Glu Ala Phe Cys Glu Glu Phe Gly Ala
    690                 695                 700

His Leu Ala Ser Phe Ala His Ile Glu Glu Asn Phe Val Asn Glu
705                 710                 715                 720

Leu Leu His Ser Lys Phe Asn Trp Thr Glu Glu Arg Gln Phe Trp Ile
            725                 730                 735

Gly Phe Asn Lys Arg Asn Pro Leu Asn Ala Gly Ser Trp Glu Trp Ser
            740                 745                 750

Asp Arg Thr Pro Val Val Ser Ser Phe Leu Asp Asn Thr Tyr Phe Gly
    755                 760                 765

Glu Asp Ala Arg Asn Cys Ala Val Tyr Lys Ala Asn Lys Thr Leu Leu
    770                 775                 780

Pro Leu His Cys Gly Ser Lys Arg Glu Trp Ile Cys Lys Ile Pro Arg
```

```
            785                 790                 795                 800
Asp Val Lys Pro Lys Ile Pro Phe Trp Tyr Gln Tyr Asp Val Pro Trp
                    805                 810                 815
Leu Phe Tyr Gln Asp Ala Glu Tyr Leu Phe His Thr Phe Ala Ser Glu
                    820                 825                 830
Trp Leu Asn Phe Glu Phe Val Cys Ser Trp Leu His Ser Asp Leu Leu
                    835                 840                 845
Thr Ile His Ser Ala His Glu Gln Glu Phe Ile His Ser Lys Ile Lys
                    850                 855                 860
Ala Leu Ser Lys Tyr Gly Ala Ser Trp Trp Ile Gly Leu Gln Glu Glu
865                 870                 875                 880
Arg Ala Asn Asp Glu Phe Arg Trp Arg Asp Gly Thr Pro Val Ile Tyr
                    885                 890                 895
Gln Asn Trp Asp Thr Gly Arg Glu Arg Thr Val Asn Asn Gln Ser Gln
                    900                 905                 910
Arg Cys Gly Phe Ile Ser Ser Ile Thr Gly Leu Trp Gly Ser Glu Glu
                    915                 920                 925
Cys Ser Val Ser Met Pro Ser Ile Cys Lys Arg Lys Lys Val Trp Leu
                    930                 935                 940
Ile Glu Lys Lys Lys Asp Thr Pro Lys Gln His Gly Thr Cys Pro Lys
945                 950                 955                 960
Gly Trp Leu Tyr Phe Asn Tyr Lys Cys Leu Leu Leu Asn Ile Pro Lys
                    965                 970                 975
Asp Pro Ser Ser Trp Lys Asn Trp Thr His Ala Gln His Phe Cys Ala
                    980                 985                 990
Glu Glu Gly Gly Thr Leu Val Ala Ile Glu Ser Glu Val Glu Gln Ala
                    995                 1000                1005
Phe Ile Thr Met Asn Leu Phe Gly Gln Thr Thr Ser Val Trp Ile
                    1010                1015                1020
Gly Leu Gln Asn Asp Asp Tyr Glu Thr Trp Leu Asn Gly Lys Pro
                    1025                1030                1035
Val Val Tyr Ser Asn Trp Ser Pro Phe Asp Ile Ile Asn Ile Pro
                    1040                1045                1050
Ser His Asn Thr Thr Glu Val Gln Lys His Ile Pro Leu Cys Ala
                    1055                1060                1065
Leu Leu Ser Ser Asn Pro Asn Phe His Phe Thr Gly Lys Trp Tyr
                    1070                1075                1080
Phe Glu Asp Cys Gly Lys Glu Gly Tyr Gly Phe Val Cys Glu Lys
                    1085                1090                1095
Met Gln Asp Thr Ser Gly His Gly Val Asn Thr Ser Asp Met Tyr
                    1100                1105                1110
Pro Met Pro Asn Thr Leu Glu Tyr Gly Asn Arg Thr Tyr Lys Ile
                    1115                1120                1125
Ile Asn Ala Asn Met Thr Trp Tyr Ala Ala Ile Lys Thr Cys Leu
                    1130                1135                1140
Met His Lys Ala Gln Leu Val Ser Ile Thr Asp Gln Tyr His Gln
                    1145                1150                1155
Ser Phe Leu Thr Val Val Leu Asn Arg Leu Gly Tyr Ala His Trp
                    1160                1165                1170
Ile Gly Leu Phe Thr Thr Asp Asn Gly Leu Asn Phe Asp Trp Ser
                    1175                1180                1185
Asp Gly Thr Lys Ser Ser Phe Thr Phe Trp Lys Asp Glu Glu Ser
                    1190                1195                1200
```

```
Ser Leu Leu Gly Asp Cys Val Phe Ala Asp Ser Asn Gly Arg Trp
1205                1210                1215

His Ser Thr Ala Cys Glu Ser Phe Leu Gln Gly Ala Ile Cys His
1220                1225                1230

Val Pro Pro Glu Thr Arg Gln Ser Glu His Pro Glu Leu Cys Ser
1235                1240                1245

Glu Thr Ser Ile Pro Trp Ile Lys Phe Lys Ser Asn Cys Tyr Ser
1250                1255                1260

Phe Ser Thr Val Leu Asp Ser Met Ser Phe Glu Ala Ala His Glu
1265                1270                1275

Phe Cys Lys Lys Glu Gly Ser Asn Leu Leu Thr Ile Lys Asp Glu
1280                1285                1290

Ala Glu Asn Ala Phe Leu Leu Glu Glu Leu Phe Ala Phe Gly Ser
1295                1300                1305

Ser Val Gln Met Val Trp Leu Asn Ala Gln Phe Asp Gly Asn Ser
1310                1315                1320

Lys

<210> SEQ ID NO 2
<211> LENGTH: 1463
<212> TYPE: PRT
<213> ORGANISM: Homo sapiens

<400> SEQUENCE: 2

Met Leu Leu Ser Pro Ser Leu Leu Leu Leu Leu Leu Gly Ala Pro
1               5                   10                  15

Arg Gly Cys Ala Glu Gly Val Ala Ala Leu Thr Pro Glu Arg Leu
                20                  25                  30

Leu Glu Trp Gln Asp Lys Gly Ile Phe Val Ile Gln Ser Glu Ser Leu
                35                  40                  45

Lys Lys Cys Ile Gln Ala Gly Lys Ser Val Leu Thr Leu Glu Asn Cys
50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
                100                 105                 110

Leu Arg Trp Arg Cys Asn Arg Lys Met Ile Thr Gly Pro Leu Gln Tyr
                115                 120                 125

Ser Val Gln Val Ala His Asp Asn Thr Val Val Ala Ser Arg Lys Tyr
130                 135                 140

Ile His Lys Trp Ile Ser Tyr Gly Ser Gly Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
                180                 185                 190

Thr Arg Glu Gly Arg Glu Asp Asp Leu Leu Trp Cys Ala Thr Thr Ser
                195                 200                 205

Arg Tyr Glu Arg Asp Glu Lys Trp Gly Phe Cys Pro Asp Pro Thr Ser
210                 215                 220

Ala Glu Val Gly Cys Asp Thr Ile Trp Glu Lys Asp Leu Asn Ser His
225                 230                 235                 240

Ile Cys Tyr Gln Phe Asn Leu Leu Ser Ser Leu Ser Trp Ser Glu Ala
```

```
                    245                 250                 255
His Ser Ser Cys Gln Met Gln Gly Gly Thr Leu Leu Ser Ile Thr Asp
            260                 265                 270

Glu Thr Glu Glu Asn Phe Ile Arg Glu His Met Ser Ser Lys Thr Val
            275                 280                 285

Glu Val Trp Met Gly Leu Asn Gln Leu Asp Glu His Ala Gly Trp Gln
            290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu Ile Val Glu Lys
                355                 360                 365

Asp Ala Trp Lys Tyr Tyr Ala Thr His Cys Glu Pro Gly Trp Asn Pro
370                 375                 380

Tyr Asn Arg Asn Cys Tyr Lys Leu Gln Lys Glu Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
            435                 440                 445

Ser Phe Glu Trp Ser Asn Asp Ser Ser Val Ile Phe Thr Asn Trp His
        450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Glu Arg
                485                 490                 495

Leu Phe Tyr Ile Cys Lys Lys Ala Gly His Val Leu Ser Asp Ala Glu
                500                 505                 510

Ser Gly Cys Gln Glu Gly Trp Glu Arg His Gly Gly Phe Cys Tyr Lys
            515                 520                 525

Ile Asp Thr Val Leu Arg Ser Phe Asp Gln Ala Ser Ser Gly Tyr Tyr
            530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
            595                 600                 605

His Gln Pro Arg Tyr Ser Gly Gly Cys Val Ala Met Arg Gly Arg His
            610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg Trp Pro Phe His Pro Cys Tyr Leu Asp Trp Glu Ser Glu Pro
                660                 665                 670
```

```
Gly Leu Ala Ser Cys Phe Lys Val Phe His Ser Glu Lys Val Leu Met
        675                 680                 685
Lys Arg Thr Trp Arg Glu Ala Glu Ala Phe Cys Glu Glu Phe Gly Ala
        690                 695                 700
His Leu Ala Ser Phe Ala His Ile Glu Glu Asn Phe Val Asn Glu
705                 710                 715                 720
Leu Leu His Ser Lys Phe Asn Trp Thr Glu Glu Arg Gln Phe Trp Ile
                725                 730                 735
Gly Phe Asn Lys Arg Asn Pro Leu Asn Ala Gly Ser Trp Glu Trp Ser
                740                 745                 750
Asp Arg Thr Pro Val Val Ser Ser Phe Leu Asp Asn Thr Tyr Phe Gly
        755                 760                 765
Glu Asp Ala Arg Asn Cys Ala Val Tyr Lys Ala Asn Lys Thr Leu Leu
770                 775                 780
Pro Leu His Cys Gly Ser Lys Arg Glu Trp Ile Cys Lys Ile Pro Arg
785                 790                 795                 800
Asp Val Lys Pro Lys Ile Pro Phe Trp Tyr Gln Tyr Asp Val Pro Trp
                805                 810                 815
Leu Phe Tyr Gln Asp Ala Glu Tyr Leu Phe His Thr Phe Ala Ser Glu
        820                 825                 830
Trp Leu Asn Phe Glu Phe Val Cys Ser Trp Leu His Ser Asp Leu Leu
        835                 840                 845
Thr Ile His Ser Ala His Glu Gln Glu Phe Ile His Ser Lys Ile Lys
        850                 855                 860
Ala Leu Ser Lys Tyr Gly Ala Ser Trp Trp Ile Gly Leu Gln Glu Glu
865                 870                 875                 880
Arg Ala Asn Asp Glu Phe Arg Trp Arg Asp Gly Thr Pro Val Ile Tyr
                885                 890                 895
Gln Asn Trp Asp Thr Gly Arg Glu Arg Thr Val Asn Asn Gln Ser Gln
                900                 905                 910
Arg Cys Gly Phe Ile Ser Ser Ile Thr Gly Leu Trp Gly Ser Glu Glu
        915                 920                 925
Cys Ser Val Ser Met Pro Ser Ile Cys Lys Arg Lys Lys Val Trp Leu
930                 935                 940
Ile Glu Lys Lys Lys Asp Thr Pro Lys Gln His Gly Thr Cys Pro Lys
945                 950                 955                 960
Gly Trp Leu Tyr Phe Asn Tyr Lys Cys Leu Leu Leu Asn Ile Pro Lys
                965                 970                 975
Asp Pro Ser Ser Trp Lys Asn Trp Thr His Ala Gln His Phe Cys Ala
                980                 985                 990
Glu Glu Gly Gly Thr Leu Val Ala Ile Glu Ser Glu Val Glu Gln Ala
        995                 1000                1005
Phe Ile Thr Met Asn Leu Phe Gly Gln Thr Thr Ser Val Trp Ile
        1010                1015                1020
Gly Leu Gln Asn Asp Asp Tyr Glu Thr Trp Leu Asn Gly Lys Pro
        1025                1030                1035
Val Val Tyr Ser Asn Trp Ser Pro Phe Asp Ile Ile Asn Ile Pro
        1040                1045                1050
Ser His Asn Thr Thr Glu Val Gln Lys His Ile Pro Leu Cys Ala
        1055                1060                1065
Leu Leu Ser Ser Asn Pro Asn Phe His Phe Thr Gly Lys Trp Tyr
        1070                1075                1080
Phe Glu Asp Cys Gly Lys Glu Gly Tyr Gly Phe Val Cys Glu Lys
        1085                1090                1095
```

Met Gln Asp Thr Ser Gly His Gly Val Asn Thr Ser Asp Met Tyr
1100                1105                1110

Pro Met Pro Asn Thr Leu Glu Tyr Gly Asn Arg Thr Tyr Lys Ile
1115                1120                1125

Ile Asn Ala Asn Met Thr Trp Tyr Ala Ala Ile Lys Thr Cys Leu
1130                1135                1140

Met His Lys Ala Gln Leu Val Ser Ile Thr Asp Gln Tyr His Gln
1145                1150                1155

Ser Phe Leu Thr Val Val Leu Asn Arg Leu Gly Tyr Ala His Trp
1160                1165                1170

Ile Gly Leu Phe Thr Thr Asp Asn Gly Leu Asn Phe Asp Trp Ser
1175                1180                1185

Asp Gly Thr Lys Ser Ser Phe Thr Phe Trp Lys Asp Glu Glu Ser
1190                1195                1200

Ser Leu Leu Gly Asp Cys Val Phe Ala Asp Ser Asn Gly Arg Trp
1205                1210                1215

His Ser Thr Ala Cys Glu Ser Phe Leu Gln Gly Ala Ile Cys His
1220                1225                1230

Val Pro Pro Glu Thr Arg Gln Ser Glu His Pro Glu Leu Cys Ser
1235                1240                1245

Glu Thr Ser Ile Pro Trp Ile Lys Phe Lys Ser Asn Cys Tyr Ser
1250                1255                1260

Phe Ser Thr Val Leu Asp Ser Met Ser Phe Glu Ala Ala His Glu
1265                1270                1275

Phe Cys Lys Lys Glu Gly Ser Asn Leu Leu Thr Ile Lys Asp Glu
1280                1285                1290

Ala Glu Asn Ala Phe Leu Leu Glu Glu Leu Phe Ala Phe Gly Ser
1295                1300                1305

Ser Val Gln Met Val Trp Leu Asn Ala Gln Phe Asp Gly Asn Asn
1310                1315                1320

Glu Thr Ile Lys Trp Phe Asp Gly Thr Pro Thr Asp Gln Ser Asn
1325                1330                1335

Trp Gly Ile Arg Lys Pro Asp Thr Asp Tyr Phe Lys Pro His His
1340                1345                1350

Cys Val Ala Leu Arg Ile Pro Glu Gly Leu Trp Gln Leu Ser Pro
1355                1360                1365

Cys Gln Glu Lys Lys Gly Phe Ile Cys Lys Met Glu Ala Asp Ile
1370                1375                1380

His Thr Ala Glu Ala Leu Pro Glu Lys Gly Pro Ser His Ser Ile
1385                1390                1395

Ile Pro Leu Ala Val Val Leu Thr Leu Ile Val Ile Val Ala Ile
1400                1405                1410

Cys Thr Leu Ser Phe Cys Ile Tyr Lys His Asn Gly Gly Phe Phe
1415                1420                1425

Arg Arg Leu Ala Gly Phe Arg Asn Pro Tyr Tyr Pro Ala Thr Asn
1430                1435                1440

Phe Ser Thr Val Tyr Leu Glu Glu Asn Ile Leu Ile Ser Asp Leu
1445                1450                1455

Glu Lys Ser Asp Gln
1460

<210> SEQ ID NO 3
<211> LENGTH: 5160
<212> TYPE: DNA

<213> ORGANISM: Homo sapiens

<400> SEQUENCE: 3

```
cccgagtgtc ggttcactgt ggagacagcg gtggcggagt gggtctccag ggctctgggc      60
tggcaaggcc cccggagggg gtggggcgcg gaggaggcta cggatccgct tccgcgcggc     120
ggggccgggt gcttgggacg cggctctggg ctcccgggat aaggggctcc cgggacaagg     180
ggctcccgga gagcccagtg gttagcgatg ctgctgtcgc cgtcgctgct gctgctgctg     240
ctgctggggg cgccgcgggg ctgcgccgag ggtgtggcgg cggcgcttac ccccgagcgg     300
ctcctggagt ggcaggataa aggaatattt gttatccaaa gtgagagtct caagaaatgc     360
attcaagcag gtaaatcggt tctgaccctg gagaactgca agcaagcaaa caagcacatg     420
ctgtggaaat gggtttcaaa ccatggcctc tttaacatag gaggcagtgg ttgcctgggc     480
ctgaatttct ccgccccaga gcagccatta agcttatatg aatgtgactc caccctcgtt     540
tccttacggt ggcgctgtaa caggaagatg atcacaggcc cgctgcagta ctctgtccag     600
gtggcgcatg acaacacagt ggtggcctca cggaagtata ttcataagtg gatttcttat     660
gggtcaggtg gtgtgagaca ttgtgaatat ctacacaaag atttgcatac aatcaaaggg     720
aacacccacg ggatgccgtg tatgtttccc ttccagtata accatcagtg gcatcatgaa     780
tgtacccgtg aaggtcggga agatgactta ctgtggtgtg ccacgacaag ccgttatgaa     840
agagatgaaa agtgggggatt ttgccctgat cccacctctg cagaagtagg ttgtgatact     900
atttgggaga aggacctcaa ttcacacatt tgctaccagt tcaacctgct ttcatctctc     960
tcttggagtg aggcacattc ttcatgccag atgcaaggag gtacgctgtt aagtattaca    1020
gatgaaactg aagaaaattt cataagggag cacatgagca gtaaaacagt ggaggtgtgg    1080
atgggcctca atcagctgga tgaacacgct ggctggcagt ggtctgatgg aacgccgctc    1140
aactatctga attggagccc agaggtaaat tttgagccat tgttgaaga tcactgtgga    1200
acatttagtt catttatgcc aagtgcctgg aggagtcggg attgtgagtc caccttgcca    1260
tatatatgta aaaatatct aaaccacatt gatcatgaaa tagttgaaaa agatgcgtgg    1320
aaatattatg ctacccactg tgagcctggc tggaatccct acaatcgtaa ttgctacaaa    1380
cttcagaaag aagaaaagac ctggcatgag gctctgcgtt cttgtcaggc tgataacagt    1440
gcattaatag acataacctc attagcagag gtggagtttc ttgtaaccct ccttggagat    1500
gaaaatgcat cagaaacatg gattggtttg agcagcaata aaattccagt ttcctttgaa    1560
tggtctaatg actcttcagt catcttact aattggcaca cacttgagcc ccacattttt    1620
ccaaatagaa gccagctgtg tgtctcagca gagcagtctg agggacactg gaaagtcaaa    1680
aattgtgaag aaagactttt ttacatttgt aaaaaagcag gccatgtcct ctctgatgct    1740
gaatcaggat gtcaagaggg atgggagaga catggtggat tctgttacaa aattgacaca    1800
gtccttcgaa gctttgacca agcttccagc ggttattact gtcctcctgc acttgtaacc    1860
attacaaaca ggtttgaaca ggcttttatt accagtttga tcagtagtgt ggtaaaaatg    1920
aaggacagtt atttttggat agctcttcag gaccaaaatg atacgggaga atacacttgg    1980
aagccagtag ggcagaaacc cgagccggtg cagtacacac actggaacac acaccagccg    2040
cgctacagtg gtgctgtgt tgccatgcga ggaaggcatc cacttggtcg ctgggaagtg    2100
aagcactgtc ggcactttaa ggcaatgtcc ttgtgcaagc agccagttga aaatcaggaa    2160
aaagcagagt atgaagagag atggcccttt caccctgct atttggactg ggagtcagag    2220
cctggtctgg ccagttgctt caaggtattt catagtgaaa aagttctgat gaaaagaaca    2280
```

```
tggagagaag ctgaagcatt ttgcgaagaa tttggagctc atcttgcaag ctttgcccat    2340
attgaggaag agaattttgt gaatgagctc ttacattcaa aatttaattg gacagaagaa    2400
aggcagttct ggattggatt taataaaaga aacccactga atgccggctc atgggagtgg    2460
tctgatagaa ctcctgttgt ctcttcgttt ttagacaaca cttatttggg agaagatgca    2520
agaaactgtg ctgtttataa ggcaaacaaa acattgctgc ccttacactg tggttccaaa    2580
cgtgaatgga tatgcaaaat cccaagagat gtgaaaccca agattccgtt ctggtaccag    2640
tacgatgtac cctggctctt ttatcaggat gcagaatacc tttttcatac ctttgcctca    2700
gaatggttga actttgagtt tgtctgtagc tggctgcaca gtgatcttct cacaattcat    2760
tctgcacatg agcaagaatt catccacagc aaaataaaag cgctatcaaa gtatggtgca    2820
agttggtgga ttggacttca agaagaaaga gccaatgatg aatttcgctg gagagatgga    2880
acaccagtga tataccagaa ctgggacaca ggaagagaaa gaactgtgaa taatcagagc    2940
cagagatgtg gctttatttc ttctataaca ggactctggg gtagtgaaga gtgttcagtt    3000
tctatgccta gtatctgtaa gcgaaaaaag gtttggctca tagagaaaaa gaaagataca    3060
ccaaaacaac atggaacgtg tcccaaagga tggctatatt ttaactataa gtgccttctg    3120
ctgaatatcc ccaaagaccc aagcagttgg aagaactgga cgcatgctca acatttctgt    3180
gctgaagaag gggggaccct ggtcgccatt gaaagtgagg tggagcaagc tttcattact    3240
atgaatcttt ttggccagac caccagtgtg tggataggtt tacaaaatga tgattatgaa    3300
acatggctaa atgaaagcc tgtggtatat tctaactggt ctccatttga tataataaat    3360
attccaagtc acaataccac tgaagttcag aaacacattc ctctctgtgc cttactctca    3420
agtaatccta tttttcattt cactggaaaa tggtattttg aagactgtgg aaaggaaggc    3480
tatgggtttg tttgtgaaaa aatgcaagat acttctggac acggtgtaaa tacatctgat    3540
atgtatccaa tgcccaatac cttagaatat ggaaacagaa cttacaaaat aattaatgca    3600
aatatgactt ggtatgcagc aataaaaacc tgcctgatgc acaaagcaca actggtcagc    3660
atcacagacc agtatcacca gtccttcctc actgttgtcc tcaaccggct aggatatgcc    3720
cactggattg gactgttcac cacagataat ggtcttaatt ttgactggtc tgatggcacc    3780
aaatcttctt tcactttttg gaaagatgag gagtcctccc tccttggtga ctgcgttttt    3840
gccgacagca acggacgctg gcatagcaca gcctgcgagt catttctgca aggtgccatt    3900
tgtcatgtgc cacctgaaac aagacaatct gaacacccag agttgtgctc agaaacatct    3960
attccctgga taaaatttaa aagtaattgc tacagttttt ctacagtcct agacagtatg    4020
agttttgagg ctgctcatga attttgcaaa aaggaaggtt ctaatctttt aacaatcaag    4080
gatgaggctg aaaatgcatt tctcctagaa gagctgtttg cttttggttc ttctgtccag    4140
atggtttggt tgaatgctca atttgatggt aacagtaagt gatttgggta gaggagagga    4200
cataaataaa tacatggttg ttaaagctga tgataatggc atctgtgagc cagaaaactc    4260
tccttggata cgttttctga gaaaaaatag catgaagcct aaagccattt cttccaaaaa    4320
caacattgca acccttttct ttaccctttt gtcttttaaa ataatcccag aacaccaaaa    4380
ataaaaacaa acaataacat gtttatcttt acccttagca ggaagatgct ggctggaac    4440 tttgtgttca cagacttagt cattgcatac caaaaccata tttactggaa atatccccag    4500
gtttctaaat gttataaaag cacaatagag ttatggaaat gtttccatga tgaactgtgc    4560
tgttaggatt cttatttgct actcataaaa accagagttt gtaataaaat ggaagcatgg    4620 tattctttc tttatgtaat tgatggttat tgaaaggtac ttgtgaagaa aattatttta    4680
```

-continued

| | |
|---|---|
| attggtatgg agagcttgtt acagtggtgt accaaggttg ggggtgagcc tacccttcg | 4740 |
| aggaggagta ttttaatcac caacattgtt tagaatttca agcagatggt gataataaaa | 4800 |
| agcagaccaa cttttagtta gctgtattgt tagtttaaa ttatttcag acaatacact | 4860 |
| attgcccaca catgggatgg actctcctac cgcccctacc cccttggtac atggctggct | 4920 |
| tggtattaaa gaaattcact gtaaaatctt tttagaaagt gagccatttt gtaatgatga | 4980 |
| agatgttagg acttcaaagg attttcttt actcgattag ttttgtttat caatgatttt | 5040 |
| ctttaaatcg attatatata tatatggaat atttcaaaat tcaaactgtc acattaagaa | 5100 |
| acatgataac ctaaatgacc taaataagaa cactgtacct aaaataaaga ggcaacttta | 5160 |

<210> SEQ ID NO 4
<211> LENGTH: 4876
<212> TYPE: DNA
<213> ORGANISM: Homo sapiens

<400> SEQUENCE: 4

| | |
|---|---|
| cccgagtgtc ggttcactgt ggagacagcg gtggcggagt gggtctccag ggctctgggc | 60 |
| tggcaaggcc cccggagggg gtggggcgcg gaggaggcta cggatccgct tccgcgcggc | 120 |
| ggggccgggt gcttgggacg cggctctggg ctcccgggat aaggggctcc cgggacaagg | 180 |
| ggctcccgga gagcccagtg gttagcgatg ctgctgtcgc cgtcgctgct gctgctgctg | 240 |
| ctgctggggg cgccgcgggg ctgcgccgag ggtgtggcgg cggcgcttac ccccgagcgg | 300 |
| ctcctggagt ggcaggataa aggaatattt gttatccaaa gtgagagtct caagaaatgc | 360 |
| attcaagcag gtaaatcggt tctgaccctg gagaactgca agcaagcaaa caagcacatg | 420 |
| ctgtggaaat gggtttcaaa ccatggcctc tttaacatag gaggcagtgg ttgcctgggc | 480 |
| ctgaatttct ccgccccaga gcagccatta agcttatatg aatgtgactc caccctcgtt | 540 |
| tccttacggt ggcgctgtaa caggaagatg atcacaggcc cgctgcagta ctctgtccag | 600 |
| gtggcgcatg acaacacagt ggtggcctca cggaagtata ttcataagtg gattctctat | 660 |
| gggtcaggtg gtgtgagacat ttgtgaatat ctacacaaag attttgcatac aatcaaaggg | 720 |
| aacacccacg ggatgccgtg tatgtttccc ttccagtata accatcagtg gcatcatgaa | 780 |
| tgtacccgtg aaggtcggga agatgactta ctgtggtgtg ccacgacaag ccgttatgaa | 840 |
| agagatgaaa agtggggatt tgccctgat cccacctctg cagaagtagg ttgtgatact | 900 |
| atttgggaga aggacctcaa ttcacacatt tgctaccagt tcaacctgct ttcatctctc | 960 |
| tcttggagtg aggcacattc ttcatgccag atgcaaggag gtacgctgtt aagtattaca | 1020 |
| gatgaaactg aagaaaattt cataagggag cacatgagca gtaaaacagt ggaggtgtgg | 1080 |
| atgggcctca atcagctgga tgaacacgct ggctggcagt ggtctgatgg aacgccgctc | 1140 |
| aactatctga attggagccc agaggtaaat tttgagccat tgttgaaga tcactgtgga | 1200 |
| acatttagtt catttatgcc aagtgcctgg aggagtcggg attgtgagtc caccttgcca | 1260 |
| tatatatgta aaaaatatct aaaccacatt gatcatgaaa tagttgaaaa agatgcgtgg | 1320 |
| aaatattatg ctacccactg tgagcctggc tggaatccct acaatcgtaa ttgctacaaa | 1380 |
| cttcagaaag aagaaagac ctggcatgag gctctgcgtt cttgtcaggc tgataacagt | 1440 |
| gcattaatag acataacctc attagcagag gtggagtttc ttgtaaccct ccttggagat | 1500 |
| gaaaatgcat cagaaacatg gattggtttg agcagcaata aaattccagt ttcctttgaa | 1560 |
| tggtctaatg actcttcagt catctttact aattggcaca cacttgagcc ccacattttt | 1620 |
| ccaaatagaa gccagctgtg tgtctcagca gagcagtctg agggacactg gaaagtcaaa | 1680 |

```
aattgtgaag aaagactttt ttacatttgt aaaaaagcag gccatgtcct ctctgatgct   1740
gaatcaggat gtcaagaggg atgggagaga catggtggat tctgttacaa aattgacaca   1800
gtccttcgaa gctttgacca agcttccagc ggttattact gtcctcctgc acttgtaacc   1860
attacaaaca ggtttgaaca ggcttttatt accagtttga tcagtagtgt ggtaaaaatg   1920
aaggacagtt attttggat agctcttcag gaccaaaatg atacgggaga atacacttgg    1980
aagccagtag ggcagaaacc cgagccggtg cagtacacac actggaacac acaccagccg   2040
cgctacagtg gtggctgtgt tgccatgcga ggaaggcatc cacttggtcg ctgggaagtg   2100
aagcactgtc ggcactttaa ggcaatgtcc ttgtgcaagc agccagttga aaatcaggaa   2160
aaagcagagt atgaagagag atggcccttt caccccctgct atttggactg ggagtcagag   2220
cctggtctgg ccagttgctt caaggtattt catagtgaaa aagttctgat gaaaagaaca   2280
tggagagaag ctgaagcatt ttgcgaagaa tttggagctc atcttgcaag ctttgcccat   2340
attgaggaag agaattttgt gaatgagctc ttacattcaa aatttaattg gacagaagaa   2400
aggcagttct ggattggatt taataaaaga aacccactga atgccggctc atgggagtgg   2460
tctgatagaa ctcctgttgt ctcttcgttt ttagacaaca cttatttttgg agaagatgca   2520
agaaactgtg ctgtttataa ggcaaacaaa acattgctgc ccttacactg tggttccaaa   2580
cgtgaatgga tatgcaaaat cccaagagat gtgaaaccca agattccgtt ctggtaccag   2640
tacgatgtac cctggctctt ttatcaggat gcagaatacc ttttttcatac ctttgcctca   2700
gaatggttga ctttgagtt tgtctgtagc tggctgcaca gtgatcttct cacaattcat    2760
tctgcacatg agcaagaatt catccacagc aaaataaaag cgctatcaaa gtatggtgca   2820
agttggtgga ttggacttca agaagaaga gccaatgatg aatttcgctg gagagatgga    2880
acaccagtga ataccagaa ctgggacaca ggaagagaaa gaactgtgaa taatcagagc    2940
cagagatgtg gctttatttc ttctataaca ggactctggg gtagtgaaga gtgttcagtt   3000
tctatgccta gtatctgtaa gcgaaaaaag gtttggctca tagagaaaaa gaaagataca   3060
ccaaaacaac atggaacgtg tcccaaagga tggctatatt ttaactataa gtgccttctg   3120
ctgaatatcc ccaaagaccc aagcagttgg aagaactgga cgcatgctca acatttctgt   3180
gctgaagaag gggggacccct ggtcgccatt gaaagtgagg tggagcaagc tttcattact   3240
atgaatcttt ttggccagac caccagtgtg tggataggtt tacaaaatga tgattatgaa   3300
acatggctaa atgaaagcc tgtggtatat tctaactggt ctccatttga tataataaat   3360
attccaagtc acaataccac tgaagttcag aaacacattc ctctctgtgc cttactctca   3420
agtaatccta attttcattt cactggaaaa tggtattttg aagactgtgg aaaggaaggc   3480
tatgggtttg tttgtgaaaa aatgcaagat acttctggac acggtgtaaa tacatctgat   3540
atgtatccaa tgcccaatac cttagaatat ggaaacagaa cttacaaaat aattaatgca   3600
aatatgactt ggtatgcagc aataaaaacc tgcctgatgc acaaagcaca actggtcagc   3660
atcacagacc agtatcacca gtccttcctc actgttgtcc tcaaccggct aggatatgcc   3720
cactggattg gactgttcac cacagataat ggtcttaatt ttgactggtc tgatggcacc   3780
aaatcttctt tcactttttg gaaagatgag gagtcctccc tccttggtga ctgcgttttt   3840
gccgacagca acggacgctg gcatagcaca ggctgcgagt catttctgca aggtgccatt   3900
tgtcatgtgc caccctgaaac aagacaatct gaacacccag agttgtgctc agaaacatct   3960
attccctgga taaaatttaa aagtaattgc tacagttttt ctacagtcct agacagtatg   4020
agttttgagg ctgctcatga attttgcaaa aaggaaggtt ctaatctttt aacaatcaag   4080
```

```
gatgaggctg aaaatgcatt tctcctagaa gagctgtttg cttttggttc ttctgtccag    4140
atggtttggt tgaatgctca atttgatggt aacaatgaaa ccataaagtg gtttgatgga    4200
actcccacag accagtcaaa ctggggcatt cggaagccag acacagacta cttcaagccc    4260
catcattgtg ttgccttgag gatccctgaa ggattatggc agctatcccc gtgtcaagaa    4320
aaaaaaggct ttatatgtaa aatggaggca gatattcaca ctgcagaggc gctgccagaa    4380
aaaggaccaa gtcacagcat cattcctctt gcggttgtac tgacactgat agtcattgtg    4440
gccatttgca cactttcctt ctgcatatac aagcataacg gtggcttctt caggagactt    4500
gcagggtttc ggaatcctta ctatcctgca accaacttta gtacagtata tttagaagaa    4560
aatattctca tttctgatct tgagaagagt gaccaataat aatgaggtca gagaatgcca    4620
cagacaccag ggtaagtaaa gaagactaaa caggagtctc atctgtcttt ccctttacag    4680
cacagatgcc attagaatgt gaattgggtc actattttaa ttattcttga agtgattact    4740
ggttttgaat cttaaccaaa tcagatgggt tttgatttat tcatttccct aaactgtgat    4800
ccattcttaa aaggggtaaa ttatgcattg gttattttc agaaagacaa gaactattaa    4860
aagaaactcc ctattg                                                    4876
```

<210> SEQ ID NO 5
<211> LENGTH: 1395
<212> TYPE: PRT
<213> ORGANISM: Homo sapiens

<400> SEQUENCE: 5

```
Met Leu Leu Ser Pro Ser Leu Leu Leu Leu Leu Leu Gly Ala Pro
1               5                   10                  15

Arg Gly Cys Ala Glu Gly Val Ala Ala Ala Leu Thr Pro Glu Arg Leu
            20                  25                  30

Leu Glu Trp Gln Asp Lys Gly Ile Phe Val Ile Gln Ser Glu Ser Leu
        35                  40                  45

Lys Lys Cys Ile Gln Ala Gly Lys Ser Val Leu Thr Leu Glu Asn Cys
    50                  55                  60

Lys Gln Ala Asn Lys His Met Leu Trp Lys Trp Val Ser Asn His Gly
65                  70                  75                  80

Leu Phe Asn Ile Gly Gly Ser Gly Cys Leu Gly Leu Asn Phe Ser Ala
                85                  90                  95

Pro Glu Gln Pro Leu Ser Leu Tyr Glu Cys Asp Ser Thr Leu Val Ser
            100                 105                 110

Leu Arg Trp Arg Cys Asn Arg Lys Met Ile Thr Gly Pro Leu Gln Tyr
        115                 120                 125

Ser Val Gln Val Ala His Asp Asn Thr Val Val Ala Ser Arg Lys Tyr
    130                 135                 140

Ile His Lys Trp Ile Ser Tyr Gly Ser Gly Gly Gly Asp Ile Cys Glu
145                 150                 155                 160

Tyr Leu His Lys Asp Leu His Thr Ile Lys Gly Asn Thr His Gly Met
                165                 170                 175

Pro Cys Met Phe Pro Phe Gln Tyr Asn His Gln Trp His His Glu Cys
            180                 185                 190

Thr Arg Glu Gly Arg Glu Asp Asp Leu Leu Trp Cys Ala Thr Thr Ser
        195                 200                 205

Arg Tyr Glu Arg Asp Glu Lys Trp Gly Phe Cys Pro Asp Pro Thr Ser
    210                 215                 220

Ala Glu Val Gly Cys Asp Thr Ile Trp Glu Lys Asp Leu Asn Ser His
225                 230                 235                 240
```

```
Ile Cys Tyr Gln Phe Asn Leu Leu Ser Ser Leu Ser Trp Ser Glu Ala
            245                 250                 255

His Ser Ser Cys Gln Met Gln Gly Gly Thr Leu Leu Ser Ile Thr Asp
        260                 265                 270

Glu Thr Glu Glu Asn Phe Ile Arg Glu His Met Ser Ser Lys Thr Val
    275                 280                 285

Glu Val Trp Met Gly Leu Asn Gln Leu Asp Glu His Ala Gly Trp Gln
290                 295                 300

Trp Ser Asp Gly Thr Pro Leu Asn Tyr Leu Asn Trp Ser Pro Glu Val
305                 310                 315                 320

Asn Phe Glu Pro Phe Val Glu Asp His Cys Gly Thr Phe Ser Ser Phe
                325                 330                 335

Met Pro Ser Ala Trp Arg Ser Arg Asp Cys Glu Ser Thr Leu Pro Tyr
            340                 345                 350

Ile Cys Lys Lys Tyr Leu Asn His Ile Asp His Glu Ile Val Glu Lys
        355                 360                 365

Asp Ala Trp Lys Tyr Tyr Ala Thr His Cys Glu Pro Gly Trp Asn Pro
    370                 375                 380

Tyr Asn Arg Asn Cys Tyr Lys Leu Gln Lys Glu Lys Thr Trp His
385                 390                 395                 400

Glu Ala Leu Arg Ser Cys Gln Ala Asp Asn Ser Ala Leu Ile Asp Ile
                405                 410                 415

Thr Ser Leu Ala Glu Val Glu Phe Leu Val Thr Leu Leu Gly Asp Glu
            420                 425                 430

Asn Ala Ser Glu Thr Trp Ile Gly Leu Ser Ser Asn Lys Ile Pro Val
        435                 440                 445

Ser Phe Glu Trp Ser Asn Asp Ser Ser Val Ile Phe Thr Asn Trp His
    450                 455                 460

Thr Leu Glu Pro His Ile Phe Pro Asn Arg Ser Gln Leu Cys Val Ser
465                 470                 475                 480

Ala Glu Gln Ser Glu Gly His Trp Lys Val Lys Asn Cys Glu Glu Arg
                485                 490                 495

Leu Phe Tyr Ile Cys Lys Lys Ala Gly His Val Leu Ser Asp Ala Glu
            500                 505                 510

Ser Gly Cys Gln Glu Gly Trp Glu Arg His Gly Gly Phe Cys Tyr Lys
        515                 520                 525

Ile Asp Thr Val Leu Arg Ser Phe Asp Gln Ala Ser Ser Gly Tyr Tyr
    530                 535                 540

Cys Pro Pro Ala Leu Val Thr Ile Thr Asn Arg Phe Glu Gln Ala Phe
545                 550                 555                 560

Ile Thr Ser Leu Ile Ser Ser Val Val Lys Met Lys Asp Ser Tyr Phe
                565                 570                 575

Trp Ile Ala Leu Gln Asp Gln Asn Asp Thr Gly Glu Tyr Thr Trp Lys
            580                 585                 590

Pro Val Gly Gln Lys Pro Glu Pro Val Gln Tyr Thr His Trp Asn Thr
        595                 600                 605

His Gln Pro Arg Tyr Ser Gly Gly Cys Val Ala Met Arg Gly Arg His
    610                 615                 620

Pro Leu Gly Arg Trp Glu Val Lys His Cys Arg His Phe Lys Ala Met
625                 630                 635                 640

Ser Leu Cys Lys Gln Pro Val Glu Asn Gln Glu Lys Ala Glu Tyr Glu
                645                 650                 655

Glu Arg Trp Pro Phe His Pro Cys Tyr Leu Asp Trp Glu Ser Glu Pro
```

-continued

```
                660                 665                 670
Gly Leu Ala Ser Cys Phe Lys Val Phe His Ser Glu Lys Val Leu Met
            675                 680                 685
Lys Arg Thr Trp Arg Glu Ala Glu Ala Phe Cys Glu Glu Phe Gly Ala
            690                 695                 700
His Leu Ala Ser Phe Ala His Ile Glu Glu Glu Asn Phe Val Asn Glu
705                 710                 715                 720
Leu Leu His Ser Lys Phe Asn Trp Thr Glu Glu Arg Gln Phe Trp Ile
                725                 730                 735
Gly Phe Asn Lys Arg Asn Pro Leu Asn Ala Gly Ser Trp Glu Trp Ser
            740                 745                 750
Asp Arg Thr Pro Val Val Ser Ser Phe Leu Asp Asn Thr Tyr Phe Gly
            755                 760                 765
Glu Asp Ala Arg Asn Cys Ala Val Tyr Lys Ala Asn Lys Thr Leu Leu
770                 775                 780
Pro Leu His Cys Gly Ser Lys Arg Glu Trp Ile Cys Lys Ile Pro Arg
785                 790                 795                 800
Asp Val Lys Pro Lys Ile Pro Phe Trp Tyr Gln Tyr Asp Val Pro Trp
            805                 810                 815
Leu Phe Tyr Gln Asp Ala Glu Tyr Leu Phe His Thr Phe Ala Ser Glu
            820                 825                 830
Trp Leu Asn Phe Glu Phe Val Cys Ser Trp Leu His Ser Asp Leu Leu
            835                 840                 845
Thr Ile His Ser Ala His Glu Gln Glu Phe Ile His Ser Lys Ile Lys
            850                 855                 860
Ala Leu Ser Lys Tyr Gly Ala Ser Trp Trp Ile Gly Leu Gln Glu Glu
865                 870                 875                 880
Arg Ala Asn Asp Glu Phe Arg Trp Arg Asp Gly Thr Pro Val Ile Tyr
                885                 890                 895
Gln Asn Trp Asp Thr Gly Arg Glu Arg Thr Val Asn Asn Gln Ser Gln
                900                 905                 910
Arg Cys Gly Phe Ile Ser Ser Ile Thr Gly Leu Trp Gly Ser Glu Glu
            915                 920                 925
Cys Ser Val Ser Met Pro Ser Ile Cys Lys Arg Lys Lys Val Trp Leu
930                 935                 940
Ile Glu Lys Lys Lys Asp Thr Pro Lys Gln His Gly Thr Cys Pro Lys
945                 950                 955                 960
Gly Trp Leu Tyr Phe Asn Tyr Lys Cys Leu Leu Leu Asn Ile Pro Lys
                965                 970                 975
Asp Pro Ser Ser Trp Lys Asn Trp Thr His Ala Gln His Phe Cys Ala
            980                 985                 990
Glu Glu Gly Gly Thr Leu Val Ala  Ile Glu Ser Glu Val  Glu Gln Ala
            995                 1000                1005
Phe Ile  Thr Met Asn Leu Phe  Gly Gln Thr Thr Ser  Val Trp Ile
            1010                1015                1020
Gly Leu  Gln Asn Asp Asp Tyr  Glu Thr Trp Leu Asn  Gly Lys Pro
            1025                1030                1035
Val Val  Tyr Ser Asn Trp Ser  Pro Phe Asp Ile Ile  Asn Ile Pro
            1040                1045                1050
Ser His  Asn Thr Thr Glu Val  Gln Lys His Ile Pro  Leu Cys Ala
            1055                1060                1065
Leu Leu  Ser Ser Asn Pro Asn  Phe His Phe Thr Gly  Lys Trp Tyr
            1070                1075                1080
```

-continued

Phe Glu Asp Cys Gly Lys Glu Gly Tyr Gly Phe Val Cys Glu Lys
1085                1090                1095

Met Gln Asp Thr Ser Gly His Gly Val Asn Thr Ser Asp Met Tyr
1100                1105                1110

Pro Met Pro Asn Thr Leu Glu Tyr Gly Asn Arg Thr Tyr Lys Ile
1115                1120                1125

Ile Asn Ala Asn Met Thr Trp Tyr Ala Ala Ile Lys Thr Cys Leu
1130                1135                1140

Met His Lys Ala Gln Leu Val Ser Ile Thr Asp Gln Tyr His Gln
1145                1150                1155

Ser Phe Leu Thr Val Val Leu Asn Arg Leu Gly Tyr Ala His Trp
1160                1165                1170

Ile Gly Leu Phe Thr Thr Asp Asn Gly Leu Asn Phe Asp Trp Ser
1175                1180                1185

Asp Gly Thr Lys Ser Ser Phe Thr Phe Trp Lys Asp Glu Glu Ser
1190                1195                1200

Ser Leu Leu Gly Asp Cys Val Phe Ala Asp Ser Asn Gly Arg Trp
1205                1210                1215

His Ser Thr Ala Cys Glu Ser Phe Leu Gln Gly Ala Ile Cys His
1220                1225                1230

Val Pro Pro Glu Thr Arg Gln Ser Glu His Pro Glu Leu Cys Ser
1235                1240                1245

Glu Thr Ser Ile Pro Trp Ile Lys Phe Lys Ser Asn Cys Tyr Ser
1250                1255                1260

Phe Ser Thr Val Leu Asp Ser Met Ser Phe Glu Ala Ala His Glu
1265                1270                1275

Phe Cys Lys Lys Glu Gly Ser Asn Leu Leu Thr Ile Lys Asp Glu
1280                1285                1290

Ala Glu Asn Ala Phe Leu Leu Glu Glu Leu Phe Ala Phe Gly Ser
1295                1300                1305

Ser Val Gln Met Val Trp Leu Asn Ala Gln Phe Asp Asp Glu Thr
1310                1315                1320

Ile Lys Trp Phe Asp Gly Thr Pro Thr Asp Gln Ser Asn Trp Gly
1325                1330                1335

Ile Arg Lys Pro Asp Thr Asp Tyr Phe Lys Pro His His Cys Val
1340                1345                1350

Ala Leu Arg Ile Pro Glu Gly Leu Trp Gln Leu Ser Pro Cys Gln
1355                1360                1365

Glu Lys Lys Gly Phe Ile Cys Lys Met Glu Ala Asp Ile His Thr
1370                1375                1380

Ala Glu Ala Leu Pro Glu Lys Gly Pro Ser His Ser
1385                1390                1395

<210> SEQ ID NO 6
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6 aauaaa                                                                    6

<210> SEQ ID NO 7
<211> LENGTH: 6

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 7

His His His His His His
1               5
```